United States Patent
Abeygunawardana et al.

(10) Patent No.: US 12,016,914 B2
(45) Date of Patent: Jun. 25, 2024

(54) **COMPOSITIONS COMPRISING *STREPTOCOCCUS PNEUMONIAE* POLYSACCHARIDE-PROTEIN CONJUGATES AND METHODS OF USE THEREOF**

(71) Applicant: Merck Sharp & Dohme LLC, Rahway, NJ (US)

(72) Inventors: Chitrananda Abeygunawardana, Ambler, PA (US); Yadong Adam Cui, Norristown, PA (US); Romulo Ferrero, Westfield, NJ (US); Jian He, Blue Bell, PA (US); Luwy Musey, Blue Bell, PA (US); Tanaz Petigara, Philadelphia, PA (US); Julie M. Skinner, Phoenixville, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 18/188,969

(22) Filed: Mar. 23, 2023

(65) Prior Publication Data
US 2023/0338498 A1    Oct. 26, 2023

Related U.S. Application Data

(62) Division of application No. 16/717,509, filed on Dec. 17, 2019, now Pat. No. 11,642,406.

(60) Provisional application No. 62/853,331, filed on May 28, 2019, provisional application No. 62/781,835, filed on Dec. 19, 2018.

(51) Int. Cl.
| | |
|---|---|
| *A61K 39/02* | (2006.01) |
| *A61K 39/09* | (2006.01) |
| *A61K 47/20* | (2006.01) |
| *A61K 47/61* | (2017.01) |
| *A61K 47/62* | (2017.01) |
| *A61P 31/04* | (2006.01) |
| *A61P 37/04* | (2006.01) |
| *A61K 39/00* | (2006.01) |

(52) U.S. Cl.
CPC ............ *A61K 39/092* (2013.01); *A61K 47/20* (2013.01); *A61K 47/61* (2017.08); *A61K 47/62* (2017.08); *A61P 31/04* (2018.01); *A61P 37/04* (2018.01); *A61K 2039/55588* (2013.01); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 3,740,421 A | 6/1973 | Schmolka |
| 4,365,170 A | 12/1982 | Okuhara |
| 4,673,574 A | 6/1987 | Anderson |
| 4,709,017 A | 11/1987 | Collier et al. |
| 4,902,506 A | 2/1990 | Anderson et al. |
| 4,912,094 A | 3/1990 | Myers et al. |
| 4,950,740 A | 8/1990 | Greenfield et al. |
| 5,057,540 A | 10/1991 | Kensil et al. |
| 5,623,057 A | 4/1997 | Marburg et al. |
| 5,843,711 A | 12/1998 | Collier et al. |
| 5,847,112 A | 12/1998 | Kniskern et al. |
| 5,917,017 A | 6/1999 | Collier et al. |
| 6,113,918 A | 9/2000 | Johnson et al. |
| 6,146,902 A | 11/2000 | McMaster |
| 6,207,646 B1 | 3/2001 | Krieg et al. |
| 6,455,673 B1 | 9/2002 | Collier |
| 7,348,006 B2 | 3/2008 | Contorni |
| 7,812,006 B2 | 10/2010 | Mistretta |
| 7,935,787 B2 | 5/2011 | Khandke et al. |
| 8,192,746 B2 | 6/2012 | Caulfield et al. |
| 8,481,054 B2 | 7/2013 | Nahm |
| 8,562,999 B2 | 10/2013 | Khandke |
| 8,753,645 B2 | 6/2014 | Biemans |
| 8,808,707 B1 | 8/2014 | Siber |
| 8,808,708 B2 | 8/2014 | Hausdorff et al. |
| 8,895,024 B2 | 11/2014 | Hausdorff |
| 9,265,839 B2 | 2/2016 | Biemans |
| 9,265,840 B2 | 2/2016 | Biemans |

(Continued)

FOREIGN PATENT DOCUMENTS

| | | |
|---|---|---|
| CN | 101590224 A | 12/2009 |
| CN | 102068690 A | 5/2011 |

(Continued)

OTHER PUBLICATIONS

Ada et al., Carbohydrate-Protein Conjugate Vaccines, Clin. Microbiology Infect., 2003, 79-85, 9.

(Continued)

*Primary Examiner* — Jennifer E Graser
(74) *Attorney, Agent, or Firm* — Matthew A. Leff; Alysia A. Finnegan

(57) ABSTRACT

The invention is related to multivalent immunogenic compositions comprising more than one *S. pneumoniae* polysaccharide protein conjugates, wherein each of the conjugates comprises a polysaccharide from an *S. pneumoniae* serotype conjugated to a carrier protein, wherein the serotypes of *S. pneumoniae* are as defined herein. Also provided are methods for inducing a protective immune response in a human patient comprising administering the multivalent immunogenic compositions of the invention to the patient. The multivalent immunogenic compositions are useful for providing protection against *S. pneumoniae* infection and/or pneumococcal diseases caused by *S. pneumoniae*.

11 Claims, 27 Drawing Sheets

Specification includes a Sequence Listing.

(56) References Cited

U.S. PATENT DOCUMENTS

| | | |
|---|---|---|
| 9,399,060 B2 | 7/2016 | Hausdorff |
| 9,422,345 B2 | 8/2016 | Blais |
| 9,492,559 B2 | 11/2016 | Emini |
| 9,669,084 B2 | 6/2017 | Siber |
| 9,778,266 B2 | 10/2017 | Nahm |
| 9,981,029 B2 | 5/2018 | Park et al. |
| 10,034,949 B2 | 7/2018 | Shin et al. |
| 10,058,607 B2 | 8/2018 | Shin et al. |
| 10,124,050 B2 | 11/2018 | Watson et al. |
| 10,406,220 B2 | 9/2019 | Siber et al. |
| 2003/0147922 A1 | 8/2003 | Capiau et al. |
| 2003/0180316 A1 | 9/2003 | Boutriau et al. |
| 2006/0228380 A1 | 10/2006 | Hausdorff |
| 2007/0002063 A1 | 1/2007 | Kumagai et al. |
| 2007/0020631 A1 | 1/2007 | Kong |
| 2007/0184071 A1 | 8/2007 | Hausdorff et al. |
| 2007/0184072 A1 | 8/2007 | Wyeth |
| 2007/0231340 A1 | 10/2007 | Hausdorff et al. |
| 2008/0286838 A1 | 11/2008 | Yuan et al. |
| 2011/0195086 A1 | 8/2011 | Caulfield et al. |
| 2012/0321660 A1 | 12/2012 | Biemans et al. |
| 2013/0344103 A1 | 12/2013 | Biemans et al. |
| 2015/0231270 A1 | 8/2015 | Prasad |
| 2015/0343076 A1 | 12/2015 | Park |
| 2018/0035359 A1 | 2/2018 | Ishii |
| 2018/0161445 A1 | 6/2018 | Dhere et al. |
| 2018/0207262 A1 | 7/2018 | Biemans et al. |
| 2018/0250389 A9 | 9/2018 | Biemans et al. |
| 2019/0224295 A1 | 7/2019 | Matur |
| 2019/0240308 A1 | 8/2019 | Matur et al. |
| 2020/0197503 A1 | 6/2020 | Abeygunawardana et al. |
| 2020/0282040 A1 | 9/2020 | Porambo et al. |
| 2020/0282070 A1 | 9/2020 | Porambo et al. |
| 2020/0324701 A1 | 10/2020 | Usui |
| 2020/0360502 A1 | 11/2020 | An et al. |

FOREIGN PATENT DOCUMENTS

| | | |
|---|---|---|
| CN | 103623401 A | 3/2014 |
| CN | 104069488 A | 10/2014 |
| CN | 103656632 B | 1/2016 |
| CN | 105999254 A | 10/2016 |
| CN | 107929728 A | 4/2018 |
| CN | 108144056 A | 6/2018 |
| CN | 108159408 A | 6/2018 |
| CN | 108245674 A | 7/2018 |
| CN | 108339115 A | 7/2018 |
| CN | 108524926 A | 9/2018 |
| CN | 108543066 A | 9/2018 |
| CN | 109091668 A | 12/2018 |
| CN | 109336989 A | 2/2019 |
| CN | 109771640 A | 5/2019 |
| CN | 110302375 A | 10/2019 |
| CN | 108079286 B | 7/2020 |
| CN | 111821432 A | 10/2020 |
| EP | 0378881 A1 | 7/1990 |
| EP | 0427347 A1 | 5/1991 |
| EP | 0471177 A2 | 2/1992 |
| EP | 0497524 A2 | 8/1992 |
| EP | 497525 B1 | 8/1992 |
| EP | 0594610 B1 | 5/1994 |
| EP | 471177 B1 | 10/1995 |
| EP | 497524 B1 | 7/1998 |
| EP | 2950815 B1 | 4/2018 |
| IN | 20140034913 A | 9/2015 |
| IN | 20140288913 A | 3/2016 |
| IN | 201623002962 A | 7/2017 |
| IN | 108524926 A | 9/2018 |
| JP | 2017504661 A | 2/2017 |
| KR | 2018043122 A | 4/2018 |
| KR | 20180043122 A | 4/2018 |
| WO | 1990014837 A1 | 12/1990 |
| WO | 1991001146 A1 | 2/1991 |
| WO | 9315760 A1 | 8/1993 |
| WO | 1993017712 A2 | 9/1993 |
| WO | 1994003208 A1 | 2/1994 |
| WO | 9508348 A1 | 3/1995 |
| WO | 1996029094 A1 | 9/1996 |
| WO | 1996039182 A1 | 12/1996 |
| WO | 9842721 A1 | 3/1998 |
| WO | 1998018930 A2 | 5/1998 |
| WO | 1998018931 A2 | 5/1998 |
| WO | 1998/033521 A1 | 8/1998 |
| WO | 1998058668 A2 | 12/1998 |
| WO | 2000061761 A2 | 10/2000 |
| WO | 2001072337 A1 | 10/2001 |
| WO | 2001098334 A2 | 12/2001 |
| WO | 2002053761 A2 | 7/2002 |
| WO | 2002083855 A2 | 10/2002 |
| WO | 2002091998 A2 | 11/2002 |
| WO | 2003009869 A1 | 2/2003 |
| WO | 2003054007 A2 | 7/2003 |
| WO | 2004071439 A2 | 8/2004 |
| WO | 2004081515 A2 | 9/2004 |
| WO | 2004083251 A2 | 9/2004 |
| WO | 2005120563 A2 | 12/2005 |
| WO | 2006065137 A2 | 6/2006 |
| WO | 2006110352 A2 | 10/2006 |
| WO | 2006110381 A1 | 10/2006 |
| WO | 2007071710 A2 | 6/2007 |
| WO | 2007071711 A2 | 6/2007 |
| WO | 2007127665 A2 | 11/2007 |
| WO | 2008021076 A2 | 2/2008 |
| WO | 2008045852 A2 | 4/2008 |
| WO | 2008079653 A1 | 7/2008 |
| WO | 2008079732 A2 | 7/2008 |
| WO | 2008118752 A2 | 10/2008 |
| WO | 2008143709 A2 | 11/2008 |
| WO | 2009000824 A2 | 12/2008 |
| WO | 2009000825 A2 | 12/2008 |
| WO | 2009009629 A1 | 1/2009 |
| WO | 2010080484 A1 | 7/2010 |
| WO | 2010080486 A2 | 7/2010 |
| WO | 2011031893 A1 | 3/2011 |
| WO | 2011100151 A1 | 8/2011 |
| WO | 2011110241 A1 | 9/2011 |
| WO | 2011151760 A2 | 12/2011 |
| WO | 2012078482 A1 | 6/2012 |
| WO | 2012158701 A1 | 11/2012 |
| WO | 2012173876 A1 | 12/2012 |
| WO | 2013191459 A1 | 12/2013 |
| WO | 2014092378 A1 | 6/2014 |
| WO | 2014097099 A2 | 6/2014 |
| WO | 2015110940 A2 | 7/2015 |
| WO | 2015110941 A2 | 7/2015 |
| WO | 2015110942 A2 | 7/2015 |
| WO | 2016113644 A1 | 7/2016 |
| WO | 2016178123 A1 | 11/2016 |
| WO | 2016199003 A1 | 12/2016 |
| WO | 2016207905 A2 | 12/2016 |
| WO | 2017011338 A1 | 1/2017 |
| WO | 2017013548 A1 | 1/2017 |
| WO | 2017067962 A1 | 4/2017 |
| WO | 2017085586 A1 | 5/2017 |
| WO | 2017085602 A1 | 5/2017 |
| WO | 2017173415 A2 | 10/2017 |
| WO | 2017220753 A1 | 12/2017 |
| WO | 2018009906 A1 | 1/2018 |
| WO | 2018027123 A1 | 2/2018 |
| WO | 2018027126 A1 | 2/2018 |
| WO | 2018048141 A1 | 3/2018 |
| WO | 2018064444 A1 | 4/2018 |
| WO | 2018080213 A1 | 5/2018 |
| WO | 2018126229 A2 | 7/2018 |
| WO | 2018134693 A1 | 7/2018 |
| WO | 2018144438 A1 | 8/2018 |
| WO | 2018144439 A1 | 8/2018 |
| WO | 2018156465 A1 | 8/2018 |
| WO | 2018156467 A1 | 8/2018 |
| WO | 2018156468 A1 | 8/2018 |
| WO | 2018156491 A1 | 8/2018 |
| WO | 2018169303 A1 | 9/2018 |
| WO | 2018227177 A1 | 12/2018 |
| WO | 2019036313 A1 | 2/2019 |

(56) References Cited

FOREIGN PATENT DOCUMENTS

| | | | |
|---|---|---|---|
| WO | 2019050813 A1 | 3/2019 | |
| WO | 2019050814 A1 | 3/2019 | |
| WO | 2019050815 A1 | 3/2019 | |
| WO | 2019050816 A1 | 3/2019 | |
| WO | 2019050818 A1 | 3/2019 | |
| WO | 2019070994 A1 | 4/2019 | |
| WO | 2019083865 A1 | 5/2019 | |
| WO | 2019131763 A1 | 7/2019 | |
| WO | 2019139692 A2 | 7/2019 | |
| WO | 2019152921 A1 | 8/2019 | |
| WO | 2019152925 A1 | 8/2019 | |
| WO | 2019170068 A1 | 9/2019 | |
| WO | 2019203599 A1 | 10/2019 | |
| WO | 2019212842 A1 | 11/2019 | |
| WO | 2019212844 A1 | 11/2019 | |
| WO | 2019212846 A1 | 11/2019 | |
| WO | 2019217183 A1 | 11/2019 | |
| WO | 2019220304 A1 | 11/2019 | |
| WO | 2019236435 A1 | 12/2019 | |
| WO | 2020009462 A1 | 1/2020 | |
| WO | 2020021416 A1 | 1/2020 | |
| WO | 2020058963 A1 | 3/2020 | |
| WO | 2020075201 A1 | 4/2020 | |
| WO | 2020121159 A1 | 6/2020 | |
| WO | 2020152706 A1 | 7/2020 | |
| WO | 2020157772 A1 | 8/2020 | |
| WO | 2020208502 A1 | 10/2020 | |
| WO | 2020247299 A1 | 12/2020 | |
| WO | 2020247301 A1 | 12/2020 | |
| WO | 2021010798 A1 | 1/2021 | |
| WO | 2021021729 A1 | 2/2021 | |

OTHER PUBLICATIONS

Andrews et al., Effectiveness of the 13-Valent Pneumococcal Conjugate Vaccine Against IPD in England and Wales, ISPPD-8, 2012, 179, Poster No. 148.

Andrews et al., Safety and immunogenicity of 15-valent pneumococcal conjugate vaccine (PCV15) compared to PCV13 in healthy older adults, Scientific Programme—Late Breakers, 2014, Abstract O-010, TP13 Special Session.

Andrews, Nick J. et al., Serotype-specific effectiveness and correlates of protection for the 13-valent pneumococcal conjugate vaccine: a postlicensure indirect cohort study, Lancet Infect. Dis., 2014, 839-846, 14.

Beall et al., Pre- and Postvaccination clonal Compositions of Invasive Pneumococcal Serotypes for Isolates Collected in the United States in 1999, 2001, and 2002, Journal of Clinical Microbiology, 2006, 999-1017, 44(3).

Bentley, S et al, Genetic Analysis of the Capsular Biosynthetic Locus from All 90 Pneumoccocal Serotypes, PLoS Genetics, 2006, 1-8, vol. 2, No. 3: e31.

Bentley, S. et al., Capsule Biosynthesis Genes and Repeat-Unit Polysaccharide Structure for All 90 Serotypes of Genetic analysis of the capsular biosynthetic locus from all 90 pneumococcal serotypes, PloS Genetics, 2006, 1, Fig. S1.

Bernatoniene, J. et al., Advances in Pneumococcal Vaccines Advantages for Infants and Children, Drugs, 2005, 229-255, 65(2).

Berry, David S. et al., Effect of O Acetylation of Neisseria meningitidis Serogroup A Capsular Polysaccharide on Development of Functional Immune Responses, Infection and Immunity, 2002, 3707-3713, 70(7).

Block et al., Pneumococcal Serotypes from Acute Otitis Mediate in Rural Kentucky, Pediatr. Infect. Dis. J., 2002, 859-865, 21.

Bo-Hyun Cho et al., Cost-effectiveness of administering 13-valent pneumococcal conjugate vaccine in addition to 23-valent pneumococcal polysaccharide vaccine to adults with immunocompromising conditions, Vaccine, 2013, 6011-6021, 31.

Bogaert, D. et al., Streptococcus pneumoniae colonisation: the key to pneumococcal disease, Lancet Infec. Dis., 2004, 144-154, 4.

Brady L. Spencer, The Pneumococcal Serotype 15C Capsule Is Partially O-Acetylated and Allows for Limited Evasion of 23-Valent Pneumococcal Polysaccharide Vaccine-Elicited Anti-Serotype 15B Antibodies, Clinical and Vaccine Immunology, Aug. 2017, 1-13, 24-8.

Brown, Paul W. et al., Characterization of Complex Prophylactic Vaccines with Protein and Glycoconjugate Components, Mass Spectrometry and Biophysical Characterization Group Analytical Research and Development, 2012, 1-34, 9th CASSS Symposium.

Burton, Robert L. et al., Development and Validation of a Fourfold Multiplexed Opsonization Assay (MOPA4) for Pneumococcal Antibodies, Clinical and Vaccine Immunology, 2006, 1004-1009, 13(9).

Bystricky, Slavomir et al., O-acetylation affects the binding properties of the carboxyl groups on the Vi bacterial polysaccharide, Biophysical Chemistry, 1994, 1-7, 51.

Caro-Aguilar, Ivette et al., Immunogenicity differences of a 15-valent pneumococcal polysaccharide conjugate vaccine (PCV15) based on vaccine dose, route of immunization and mouse strain, Vaccine, 2017, 865-872, 35(6).

Chiayung Chu et al., Further Studies on the Immunogenicity of Haemophilus influenzae Type b and Pneumococcal Type 6A Polysaccharide-Protein Conjugates, Infection and Immunity, Apr. 1983, 245-256, vol. 40(1).

Choi, Eun Hwa et al., Capsular Polysaccharide (CPS) Release by Serotype 3 Pneumococcal Strains Reduces the Protective Effect of Anti-Type 3 CPS Antibodies, Clinical and Vaccine Immunology, 2016, 162-167, 23(2).

Cooper et al., The 13-valent pneumococcal conjugate vaccine (PCV13) elicts cross-functional opsoophagocytic killing responses in humans to Streptococcus pneumoniae serotypes 6C and 7A, Vaccine, 2011, 7207-7211, 29.

Dagan et al., Glycoconjugate Vaccines and Immune Interference: A Review, Vaccine, 2010, 5513-5523, 28.

Daniela Verthelyi, Adjuvant Properties of CpG Oligonucleotides in Primates, Methods Mol Med, 2006, 139-58, 127.

De La Pena, C. et al., Present and future of the pneumonia vaccination, Pediatrics, 2004, 47-55, 24(4).

Eskola, J. et al., Cross-Reactivity of Antibodies to Type 6B and 6A Polysaccharides of Streptococcus pneumoniae, Evoked by Pneumococcal Conjugate Vaccines, in Infants, Journal of Infectious Diseases, 2001, 789-793, 184.

Excerpt (Ex B) Summary of Product Characteristics for Prevenar 2005, 15 pages.

Fabiana Falugi et al., Rationally designed strings of promiscuous CD4 T cell epitopes provide help to Haemophilus influenzae type b oligosaccharide: a model for new conjugate vaccines, Eur. J. Immunol., 2001, 3816-3824, 31.

Fikri Y. Avci et al., A mechanism for glycoconjugate vaccine activation of the adaptive immune system and its implications for vaccine design, Nature Medicine, Dec. 2011, 1602-1610, 17-12.

Finn, Adam, Bacterial polysaccharide-protein conjugate vaccines, British Medical Bulletin, 2004, 1-14, 70.

Frasch, Carl E., Preparation of bacterial polysaccharide-protein conjugates: Analytical and manufacturing challenges, Vaccine, 2009, 6468-6470, 27.

Ganaie, Feroze et al., A New Pneumococcal Capsule Type, 10D, is the 100th Serotype and Has a Large cps Fragment from an Oral Streptococcus, mBio, 2020, 1-15, 11:e00937-20.

Geoffry S. Bethell et al., A Novel Method of Activation of Crosslinked Agaroses with 1,1'-Carbonyldiimidazole Which Gives a Matrix for Affinity Chromatography Devoid of Additional Charged Groups, The Journal of Biological Chemistry, 1979, 2572-2574, 254-8.

Ginsburg, A.S. et al., New Conjugate Vaccines for the Prevention of Pneumococcal Disease in Developing Countries, Drugs of Today, 2011, 207-214, 47(3).

Gowrisankar Rajam et al., Functional Antibodies to the O-Acetylated Pneumococcal Serotype 15B Capsular Polysaccharide Have Low Cross-Reactivities with Serotype 15C, Clinical and Vaccine Immunology, Sep. 2007, 1223-1227, 14-9.

Grabenstein, J.D. et al., A century of pneumococcal vaccination research in humans, Clinical Microbiology and Infection, 2012, 15-24, 18 (Suppl. 5).

(56) References Cited

OTHER PUBLICATIONS

Greene, Carolyn M. et al., Preventability of Invasive Pneumococcal Disease and Assessment of Current Polysaccharide Vaccine Recommendations for Adults: United States, 2001-2003, Clinical Infectious Diseases, 2006, 141-150, 43.

Hausdorff et al., Multinational Study of Pneumococcal Serotypes Causing Acute Otilitis Media in Children, Pediatr. Infect. Dis. J., 2002, 1008-1016, 21(11).

Hausdorff et al., The epidemiology of invasive pneumococcal disease: implications for conjugate vaccine development, The First International Symposium on Pneumococci and Pneumococcal Diseases (ISPPD-1), 1998, 27, 2-13:30, US.

Hausdorff et al., Which Pneumococcal Serogroups Cause the Most Invasive Disease Implications for Conjugate Vaccine Formation and Use, Part 1, Clinical Infectious Diseases, 2000, 100-121, 30.

Hausdorff, W.P. et al., Characteristics of Individual Pneumococcal Serotypes, The Fourth International Symposium on Pneumococci and Pneumococcal Diseases (ISPPD-4), 2004, 50, EPI-35.

Hausdorff, W.P. et al., Epidemiological differences among pneumococcal serotypes, Lancet Infectious Diseases, 2005, 83-93, 5.

Hausdorff, W.P. et al., Geographical differences in invasive pneumococcal disease rates and serotype frequency in young children, Lancet, 2001, 950-952, 357(9260).

Hausdorff, W.P. et al., Predicting the impact of new pneumococcal conjugate vaccines: serotype composition is not enough, Expert Review Vaccines, 2015, 413-428, 14(3).

Hausdorff, W.P. et al., The Contribution of Specific Pneumococcal Serogroups to Different Disease Manifestations: Implications for Conjugate Vaccine Formulation and Use, Part II, Clinical Infectious Diseases, 2000, 122-140, 30(1).

Hausdorff, W.P., Invasive pneumococcal disease in children: geographic and temporal variations in incidence and serotype distribution, European Journal of Pediatrics, 2002, S135-S139, 161 (Suppl. 2).

Henrichsen, Jorgen, Six Newly Recognized Types of *Streptococcus pneumoniae*, Journal of Clinical Microbiology, 1995, 2759-2762, 10.

Hevey, R. et al., Conjugation Strategies Used for the Preparation of Carbohydrate-Conjugate Vaccines, Chemistry of Bioconjugates: Synthesis, Characterization, and Biomedical Applications, First Edition, 2014, 387-413, Chapter 16.

Hicks et al., Incidence of Pneumococcal Disease Due to Non-Pneumococcal Conjugate Vaccine (PCV7) Serotypes in the US During the Era of Widespread PCV7 Vaccination, Journal of Infectious Diseases, 2007, 1346-1354, 196.

Ho, Mei M. et al., Physico-chemical and immunological examination of the thermal stability of tetanus toxoid conjugate vaccines, Vaccine, 2002, 3509-3522, 20.

Hsieh CL, Characterization of saccharide-CRM197 conjugate vaccines, Dev. Biol. (Basel), 2000, 93-104, 103.

Huebner, Robin E. et al., Long-term antibody levels and booster responses in South African children immunized with nonavalent pneumococcal conjugate vaccine, Vaccine, 2004, 2696-2700, 22.

International Search Report—Written Opinion of the International Search Authority for PCT/US2018/063709, 14 pages, dated Jul. 26, 2019.

Jakobsen et al., Pneumococcal serotype 19F conjugate vaccine induces cross-protective immunity to serotype 19A in a murine pneumococcal pneumoniae model, Infection and Immunity, 2003, 2956-2959, 71.

Joseph Kuo et al., Characterization of a Recombinant Pneumolysin and Its Use as a Protein Carrier for Pneumococcal Type 18C, Infection and Immunity, Jul. 1995, 2706-2713, 63-7.

Juan J. Calix et al., Biochemical, Genetic and Serological Characterization of Two Capsule Subtypes Among *Streptococcus pneumoniae* Serotype 20 Strains: Discovery of a New Pneumococcal Serotype, J. Biol. Chem., 2012, 27885-27894, 287-33.

K. Aaron Geno, Pneumococcal Capsules and Their Types: Past, Present, and Future, Clinical Microbiology Reviews, 2015, 871-899, 28.

Karin Baraldo et al., N19 Polyepitope as a Carrier for Enhanced Immunogenicity and Protective Efficacy of Meningococcal Conjugate Vaccines, Infection and Immunity, Aug. 2004, 4884-4887, 72-8.

Kei Yasuda et al., Role of Immunostimulatory DNA and TLR9 in Gene Therapy, Crit Rev Ther Drug Carrier Systems, 2006, 89-109, 23-2.

Kieninger, D.M., 48th Annual ICAAC/ISDA 46th Annual Meeting, Oct. 25-28, 2008.

Klugman, K.P. et al., Pneumococcal conjugate vaccine and pneumococcal common protein vaccines, Vaccines, 2013, 504-541, Chapter 25, 6th Edition.

Kyaw et al., Effect of Introduction of the Pneumococcal Conjugate Vaccine on Drug-Resistant *Streptococcus pneumoniae*, New England Journal of Medicine, 2006, 1455-1463, 354(14).

Lambrecht et al., Mechanism of action of clinically approved adjuvants, Current Opinion Immunology, 2009, pp. 23-29, vol. 21(1).

Lexau, C.A. et al., Changing Epidemiology of Invasive Pneumococcal Disease Among Older Adults in the Era of Pediatric Pneumococcal Conjugate Vaccine, The Journal of the American Medical Association, 2005, 2043-2051, 294 (16).

MacNair, J.E. et al., Alignment of absolute and relative molecular size specifications for a polyvalent pneumococcal polysaccharide vaccine (PNEUMOVAX 23), Biologicals, 2005, 49-58, 33.

Marchese, Rocio D. et al., Optimization and Validation of a Multiplex, Electrochemiluminescence-Based Detection Assay for the Quantitation of Immunoglobulin G Serotype-Specific Antipneumococcal Antibodies in Human Serum, Clinical and Vaccine Immunology, 2009, 387-396, 16(3).

McFetridge, R. et al., Safety, tolerability, and immunogenicity of 15-valent pneumococcal conjugate vaccine in healthy adults, Vaccine, 2015, 2793-2799, 33.

McIntosh, E.D. et al., Global prevailing and emerging pediatric pneumococcal serotypes, Expert Review Vaccines, 2011, 109-129, 10(1).

Merck Sharp & Dohme Corp. (Petitioner), Pfizer Inc. (Patent Owner), Petition for Inter Partes Review, (AIA Review # IPR2017-02136), Case IPR2017-___, U.S. Pat. No. 9,492,559, dated Sep. 20, 2017, 81 pages.

Merck Sharp & Dohme Corp. (Petitioner), Pfizer Inc. (Patent Owner), Petition for Inter Partes Review, (AIA Review # IPR2017-02131), Case IPR2017-___, U.S. Pat. No. 9,492,559, dated Sep. 19, 2017, 82 pages.

Merck Sharp & Dohme Corp. (Petitioner), Pfizer Inc. (Patent Owner), Petition for Inter Partes Review, (AIA Review # IPR2017-02132), Case IPR2017-___, U.S. Pat. No. 9,492,559, dated Sep. 19, 2017, 85 pages.

Merck Sharp & Dohme Corp. (Petitioner), Pfizer Inc. (Patent Owner), Petition for Inter Partes Review, (AIA Review # IPR2017-02138), Case IPR2017-___, U.S. Pat. No. 9,492,559, dated Sep. 20, 2017, 82 pages.

Merck Sharp & Dohme Corp. (Petitioner), Wyeth LLC (Patent Owner), Petition for Inter Partes Review, (AIA Review # IPR2017-00378), Case IPR2016-___, U.S. Pat. No. 8,562,999, dated Dec. 1, 2016, 85 pages.

Merck Sharp & Dohme Corp. (Petitioner), Wyeth LLC (Patent Owner), Petition for Inter Partes Review, (AIA Review # IPR2017-00390), Case IPR2016-___, U.S. Pat. No. 8,562,999, dated Dec. 2, 2016, 83 pages.

Merck Sharp & Dohme Corp. (Petitioner), Wyeth LLC (Patent Owner), Petition for Inter Partes Review, (AIA Review # IPR2017-01194), Case IPR2017-___, U.S. Pat. No. 8,895,024, dated Mar. 29, 2017, 83 pages.

Merck Sharp & Dohme Corp. (Petitioner), Wyeth LLC (Patent Owner), Petition for Inter Partes Review, (AIA Review # IPR2017-01211), Case IPR2017-___, U.S. Pat. No. 9,399,060, dated Mar. 30, 2017, 71 pages.

Merck Sharp & Dohme Corp. (Petitioner), Wyeth LLC (Patent Owner), Petition for Inter Partes Review, (AIA Review # IPR2017-01215), Case IPR2017-___, U.S. Pat. No. 9,399,060, dated Mar. 30, 2017, 81 pages.

(56) References Cited

OTHER PUBLICATIONS

Merck Sharp & Dohme Corp. (Petitioner), Wyeth LLC (Patent Owner), Petition for Inter Partes Review, (AIA Review # IPR2017-01223), Case IPR2017-___, U.S. Pat. No. 9,399,060, dated Mar. 31, 2017, 60 pages.

Merck Sharp & Dohme Corp. (Petitioner), Wyeth LLC (Patent Owner), Petition for Post Grant Review, (AIA Review # PGR2017-00016), Case PGR2017-___, U.S. Pat. No. 9,399,060, dated Mar. 22, 2017, 105 pages.

Merck Sharp & Dohme Corp. (Petitioner), Wyeth LLC (Patent Owner), Petition for Post Grant Review, (AIA Review # PGR2017-00017), Case PGR2017-___, U.S. Pat. No. 9,399,060, dated Mar. 24, 2017, 98 pages.

Michael J. Gidley et al., Reductive methylation of proteins with sodium cyanoborohydride, Biochem, 1982, 331-334, 203.

Milton T. W. Hearn et al., Application of 1,1'-Carbonyldiimidazole-activated Matrices for the purification of proteins, Journal of Chromatography, 1981, 509-518, 218.

MMWR, Direct and Indirect Effects of Routine Vaccination of Children with 7-Valent Pneumococcal Conjugate Vaccine on Incidence of Invasive Pneumococcal Disease, Centers for Disease Control and Prevention, 2005, 893-897, 54(36).

Morbidity and Mortality Weekly Report, Geographic Differences in HIV Infection Among Hispanics or Latinos—46 States and Puerto Rico, 2010, Centers for Disease Control and Prevention, 2012, 1-20, 61(40).

Neil Jentoft et al., Protein Labeling by Reductive Methylation with Sodium Cyanoborohydride: Effect of Cyanide and Metal Ions on the Reaction, Analytical Biochemistry, 1980, 186-190, 106.

O'Brien et al., Potential Impact of Conjugate Pneumococcal Vaccines of Pediatric Pneumococcal Diseases, Am. J. Epidemiol., 2004, 634-644, 159(7).

Obaro et al., Safety and Immunogenicity of Pneumococcal Conjugate Vaccine in Combination with Diphtheria, Tetanus Toxoid, Pertussis and Haemophilus Influenzae Type B Conjugate Vaccine, Pediatr. Infect. Dis. J., 2002, 940-946, 21(10).

Overturf et al., Pneumococcal Vaccination of Children, Seminars in Pediatric Infectious Diseases, 2002, 155-164, 13(3).

Paradiso, P., Essential criteria for evaluation of pneumococcal conjugate vaccine candidates, Vaccine, 2009, C15-C18, 27 (Suppl. 3).

Park et al., Differential Effects of pneumococcal vaccines against serotypes 6A and 6C, J Infect Dis, 2008, 1818-1822, 198.

Park, I.H. et al., Discovery of a New Capsular Serotype (6C) within Serogroup 6 of *Streptococcus pneumoniae*, Journal of Clinical Microbiology, 2007, 1225-1233, 45.

PDR, Prevnar, Physicians' Desk Reference, 2001, 1-9, 55 Edition.

Petitioner: *Merck Sharp & Dohme Corp.* v. Patent Owner: *GlaxoSmithKline Biologicals S.A.*, dated Jun. 11, 2018, 83 pages.

Petitioner: *Merck Sharp & Dohme Corp.* v. Patent Owner: *GlaxoSmithKline Biologicals S.A.*, dated Jun. 11, 2018, 84 pages.

Petitioner: *Merck Sharp & Dohme Corp.* v. Patent Owner: *GlaxoSmithKline Biologicals S.A.*, dated Jun. 11, 2018, 86 pages.

Petitioner: *Merck Sharp & Dohme Corp.* v. Patent Owner: *GlaxoSmithKline Biologicals S.A.*, dated Nov. 7, 2018, 83 pages.

Petitioner: *Merck Sharp & Dohme Corp.* v. Patent Owner: *GlaxoSmithKline Biologicals S.A.*, dated Nov. 7, 2018, 84 pages.

Pneumococcal Vaccine Polyvalent (Product Information), 2013, 6 pages.

Pollabauer, E.M. et al., The influence of carrier protein on the immunogenicity of simultaneously administered conjugate vaccines in infants, Vaccine, 2009, 1674-1679, 27.

Prymula et al., A Randomized Double-blind Efficacy Study, The Lancet, 2006, 740-748, 367.

Sanjiv Sur et al., Long Term Prevention of Allergic Lung Inflammation in a Mouse Model of Asthma by CpG Oligodeoxynucleotides, Journal of Immunology, 1999, 6284-6293, 162.

Sigurdardottir, Sigurveig T. et al., Immune response to octavalent diphtheria- and tetanus-conjugated pneumococcal vaccines is serotype- and carrier-specific: the choice for a mixed carrier vaccine, Pediatr Infect Dis J, 2002, 548-554, 21(6).

Sigurdardottir, Sigurveig TH. et al., Safety and immunogenicity of CRM197-conjugated pneumococcal-meningococcal C combination vaccine (9vPnC-MnCC) whether given in two or three primary doses, Vaccine, 2008, 4178-4186, 26.

Skinner et al., Pre-clinical Evaluation of a 15-Valent Pneumococcal Conjugate Vaccine (PCV15-CRM197) In an Infant-Rhesus Monkey Immunogenicity Model, Vaccine, 2011, 8870-8876, 29.

Smith, Edward J., Technical Report 12, Siliconization of Parenteral Drug Packaging Components, Journal of Parenteral Science and Technology, The Parenteral Drug Association, 1988, S4-S13, 42 (Suppl. 4).

Stacey, H.L. et al., Safety and immunogenicity of 15-valent pneumococcal conjugate vaccine (PCV-15) compared to PCV-13 in healthy older adults, Human Vaccines & Immunotherapeutics, 2019, 530-539, 15(3).

Su Wang et al., Adjuvant synergy in the response to hepatitis B vaccines, Science Direct, 2003, 4297-4306, 21.

T. Ben-Yedidia et al., Effect of pre-existing carrier immunity on the efficacy of synthetic influenza vaccine, Immunology Letters, 1998, 9-15, 64.

Traore et al., Incidence, Seasonality, Age Distribution, and Morality of Pneumococcal Meningitis in Burkina Faso and Togo, Clinical Infectious Disease, 2009, S181-S189, 48.

Tsuyoshi Uchida et al., Diphtheria Toxin and Related Proteins, J Biol Chem, 1973, 3838-3844, 218.

W. Nicklas, Aluminum salts, Research in Immunology, 1992, 489-493, 143.

Whitney et al., Decline in Invasive Pneumococcal Disease After the Introduction of Protein-Poloysacchairde Conjugate Vaccine, New England Journal of Medicine, 2003, 1737-1746, 348(18).

FIG.4

COMPOSITIONS COMPRISING *STREPTOCOCCUS PNEUMONIAE* POLYSACCHARIDE-PROTEIN CONJUGATES AND METHODS OF USE THEREOF

CROSS REFERENCE TO RELATED APPLICATIONS

The present application is a divisional application of Ser. No. 16/717,509, filed Dec. 17, 2019, which is a U.S. Non-Provisional Application, which claims the benefit of U.S. Provisional Application No. 62/853,331, filed May 28, 2019, and U.S. Provisional Application No. 62/781,835, filed Dec. 19, 2018, hereby incorporated by reference in its entirety.

FIELD OF THE INVENTION

The present invention provides multivalent immunogenic compositions having distinct polysaccharide-protein conjugates. Each conjugate consists of a capsular polysaccharide prepared from a different serotype of *Streptococcus pneumoniae* conjugated to a carrier protein, preferably CRM197. The immunogenic compositions provide broad coverage against pneumococcal disease.

REFERENCE TO SEQUENCE LISTING SUBMITTED ELECTRONICALLY

The instant application contains a Sequence Listing which has been submitted electronically in XML format and is hereby incorporated by reference in its entirety. The XML file, created on Mar. 21, 2023, is named 24683USDIV2-SEQLIST-21MAR2023.xml and is 2.62 KB (2,693 bytes) in size.

BACKGROUND OF THE INVENTION

*Streptococcus pneumoniae* is a Gram-positive bacterium and the most common cause of invasive bacterial disease (such as pneumonia, bacteraemia, meningitis and Otitis media) in infants and young children. Pneumococcus is encapsulated with a chemically linked polysaccharide which confers serotype specificity. There are over 90 known serotypes of pneumococci, and the capsule is the principle virulence determinant for pneumococci, as the capsule not only protects the inner surface of the bacteria from complement, but is itself poorly immunogenic. Polysaccharides are T-cell independent antigens, and, in most cases, can not be processed or presented on MHC molecules to interact with T-cells. They can however, stimulate the immune system through an alternate mechanism which involves cross-linking of surface receptors on B cells.

The multivalent pneumococcal polysaccharide vaccines that have been licensed for many years have proved valuable in preventing pneumococcal disease in adults, particularly, the elderly and those at high-risk. However, infants and young children respond poorly to unconjugated pneumococcal polysaccharides. The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36): 893-7. However, there are limitations in serotype coverage with Prevnar® in certain regions of the world and some evidence of certain emerging serotypes in the United States (for example, 19A and others). See O'Brien et al., 2004, *Am J Epidemiol* 159:634-44; Whitney et al., 2003, *N Engl J Med* 348:1737-46; Kyaw et al., 2006, *N Engl J Med* 354:1455-63; Hicks et al., 2007, *J Infect Dis* 196:1346-54; Traore et al., 2009, *Clin Infect Dis* 48:S181-S189.

U.S. Patent Application Publication No. US 2006/0228380 describes a 13-valent pneumococcal polysaccharide-protein conjugate vaccine including serotypes 1, 3, 4, 5, 6A, 6B, 7F, 9V, 14, 18C, 19A, 19F and 23F. Chinese Patent Application Publication No. CN 101590224 A describes a 14-valent pneumococcal polysaccharide-protein conjugate vaccine including serotypes 1, 2, 4, 5, 6A, 6B, 7F, 9N, 9V, 14, 18C, 19A, 19F and 23F.

Other PCVs have covered 7, 10, 11, or 13 of the serotypes contained in PCV-15 (U.S. Pub. No. 2011/0195086), but immune interference has been observed for some serotypes (e.g. lower protection for serotype 3 in GSK's PCV-11) and lower response rates to serotype 6B in Pfizer's PCV-13 (PREVNAR® 13). See Prymula et al., 2006, Lancet 367: 740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48th Annual ICAAC/ISDA 46th Annual Meeting, Washington DC, Oct. 25-28, 2008.

The current multivalent pneumococcal vaccines have been effective in reducing the incidence of pneumococcal disease associated with those serotypes present in the vaccines. However, the prevalence of the pneumococci expressing serotypes not present in the currently available vaccines has been increasing. Accordingly, there is a need for additional pneumococcal vaccine compositions which can provide protection against pneumococcal serotypes not present in currently available vaccines.

SUMMARY OF THE INVENTION

The invention provides multivalent immunogenic compositions comprising *S. pneumoniae* polysaccharide protein conjugates, wherein each of the conjugates comprises a polysaccharide from a *S. pneumoniae* serotype conjugated to a carrier protein, and wherein the polysaccharide protein conjugates include polysaccharides of a group of *S. pneumoniae* serotypes selected from the group consisting of:
 a) 1, 3, 4, 5, 6A, 6B, 7F, 9V, 10A, 12F, 14, 15A, DeOAc15B, 18C, 19A, 19F, 22F, 23B, 23F, 24F, 33F and 35B;
 b) 1, 3, 4, 5, 6A, 6B, 7F, 9V, 10A, 12F, 14, 15A, 15C, 18C, 19A, 19F, 22F, 23B, 23F, 24F, 33F and 35B;
 c) 1, 3, 4, 5, 6A, 6B, 7F, 8, 9V, 10A, 12F, 14, 15A, DeOAc15B, 18C, 19A, 19F, 22F, 23B, 23F, 24F, 33F and 35B;
 d) 1, 3, 4, 5, 6A, 6B, 7F, 8, 9V, 10A, 12F, 14, 15A, 15C, 18C, 19A, 19F, 22F, 23B, 23F, 24F, 33F and 35B;
 e) 1, 3, 4, 5, 6A, 6B, 7F, 8, 9V, 10A, 12F, 14, 15B, 18C, 19A, 19F, 22F, 23B, 23F, 24F, 33F and 35B;
 f) 1, 3, 4, 5, 6A, 6B, 7F, 8, 9V, 10A, 11A, 12F, 14, 15A, DeOAc15B, 18C, 19A, 19F, 22F, 23B, 23F, 24F, 33F and 35B;
 g) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B;

h) 1, 3, 4, 5, 6A, 6B, 7F, 8, 9V, 10A, 11A, 12F, 14, 15A, 15B, 18C, 19A, 19F, 22F, 23B, 23F, 24F, 33F and 35B;
i) 1, 3, 4, 5, 6A, 6B, 7F, 8, 9V, 10A, 11A, 12F, 14, 15B, 18C, 19A, 19F, 22F, 23B, 23F, 24F, 33F and 35B;
j) 1, 3, 4, 5, 6A, 7F, 9V, 10A, 12F, 14, 15A, 15C, 18C, 19A, 19F, 22F, 23B, 23F, 24F, 33F and 35B;
k) 1, 3, 4, 5, 6B, 7F, 9V, 10A, 12F, 14, 15A, 15C, 18C, 19A, 19F, 22F, 23B, 23F, 24F, 33F and 35B;
l) 1, 3, 4, 5, 6C, 7F, 9V, 10A, 12F, 14, 15A, 15C, 18C, 19A, 19F, 22F, 23B, 23F, 24F, 33F and 35B;
m) 1, 3, 4, 5, 6A, 7F, 8, 9V, 10A, 12F, 14, 15A, 15C, 18C, 19A, 19F, 22F, 23B, 23F, 24F, 33F and 35B;
n) 1, 3, 4, 5, 6B, 7F, 8, 9V, 10A, 12F, 14, 15A, 15C, 18C, 19A, 19F, 22F, 23B, 23F, 24F, 33F and 35B;
o) 1, 3, 4, 5, 6C, 7F, 8, 9V, 10A, 12F, 14, 15A, 15C, 18C, 19A, 19F, 22F, 23B, 23F, 24F, 33F and 35B;
p) 1, 3, 4, 5, 6A, 7F, 8, 9V, 10A, 11A, 12F, 14, 15A, 15C, 18C, 19A, 19F, 22F, 23B, 23F, 24F, 33F and 35B;
q) 1, 3, 4, 5, 6B, 7F, 8, 9V, 10A, 11A, 12F, 14, 15A, 15C, 18C, 19A, 19F, 22F, 23B, 23F, 24F, 33F and 35B;
r) 1, 3, 4, 5, 6C, 7F, 8, 9V, 10A, 11A, 12F, 14, 15A, 15C, 18C, 19A, 19F, 22F, 23B, 23F, 24F, 33F and 35B;
s) 1, 3, 4, 5, 6A, 7F, 9V, 10A, 12F, 14, 15A, 15B, 18C, 19A, 19F, 22F, 23B, 23F, 24F, 33F and 35B;
t) 1, 3, 4, 5, 6B, 7F, 9V, 10A, 12F, 14, 15A, 15B, 18C, 19A, 19F, 22F, 23B, 23F, 24F, 33F and 35B;
u) 1, 3, 4, 5, 6C, 7F, 9V, 10A, 12F, 14, 15A, 15B, 18C, 19A, 19F, 22F, 23B, 23F, 24F, 33F and 35B;
v) 1, 3, 4, 5, 6A, 7F, 8, 9V, 10A, 12F, 14, 15A, 15B, 18C, 19A, 19F, 22F, 23B, 23F, 24F, 33F and 35B;
w) 1, 3, 4, 5, 6B, 7F, 8, 9V, 10A, 12F, 14, 15A, 15B, 18C, 19A, 19F, 22F, 23B, 23F, 24F, 33F and 35B;
x) 1, 3, 4, 5, 6C, 7F, 8, 9V, 10A, 12F, 14, 15A, 15B, 18C, 19A, 19F, 22F, 23B, 23F, 24F, 33F and 35B;
y) 1, 3, 4, 5, 6A, 7F, 8, 9V, 10A, 11A, 12F, 14, 15A, 15B, 18C, 19A, 19F, 22F, 23B, 23F, 24F, 33F and 35B;
z) 1, 3, 4, 5, 6B, 7F, 8, 9V, 10A, 11A, 12F, 14, 15A, 15B, 18C, 19A, 19F, 22F, 23B, 23F, 24F, 33F and 35B; and
aa) 1, 3, 4, 5, 6C, 7F, 8, 9V, 10A, 11A, 12F, 14, 15A, 15B, 18C, 19A, 19F, 22F, 23B, 23F, 24F, 33F and 35B.

The invention provides a multivalent immunogenic composition comprising 22 distinct polysaccharide protein conjugates, wherein each of the conjugates comprises a capsular polysaccharide from a *S. pneumoniae* serotype conjugated to a carrier protein, wherein the polysaccharide are prepared from *S. pneumoniae* serotypes 1, 3, 4, 5, 6A, 6B, 7F, 9V, 10A, 12F, 14, 15A, 15C, 18C, 19A, 19F, 22F, 23B, 23F, 24F, 33F and 35B.

The invention provides a multivalent immunogenic composition comprising 22 distinct polysaccharide protein conjugates, wherein each of the conjugates comprises a polysaccharide from a *S. pneumoniae* serotype conjugated to a carrier protein, and wherein the polysaccharide protein conjugates include polysaccharides of a group of *S. pneumoniae* serotypes selected from the group consisting of: 1, 3, 4, 5, 6A, 6B, 7F, 9V, 10A, 12F, 14, 15A, 15C, 18C, 19A, 19F, 22F, 23B, 23F, 24F, 33F and 35B.

The invention provides a multivalent immunogenic composition comprising 23 distinct polysaccharide protein conjugates, wherein each of the conjugates comprises a capsular polysaccharide from a *S. pneumoniae* serotype conjugated to a carrier protein, wherein the polysaccharide are prepared from *S. pneumoniae* serotypes 1, 3, 4, 5, 6A, 6B, 7F, 8, 9V, 10A, 12F, 14, 15A, 15C, 18C, 19A, 19F, 22F, 23B, 23F, 24F, 33F and 35B.

The invention provides a multivalent immunogenic composition comprising 23 distinct *S. pneumoniae* polysaccharide protein conjugates, wherein each of the conjugates comprises a capsular polysaccharide from a *S. pneumoniae* serotype conjugated to a carrier protein, wherein each distinct polysaccharide protein conjugate comprises a polysaccharide from *S. pneumoniae* serotypes 1, 3, 4, 5, 6A, 6B, 7F, 8, 9V, 10A, 12F, 14, 15A, 15C, 18C, 19A, 19F, 22F, 23B, 23F, 24F, 33F and 35B, respectively, and wherein the carrier protein is CRM197.

The invention provides a multivalent immunogenic composition comprising 24 distinct polysaccharide protein conjugates, wherein each of the conjugates comprises a capsular polysaccharide from a *S. pneumoniae* serotype conjugated to a carrier protein, wherein the polysaccharide are prepared from *S. pneumoniae* serotypes 1, 3, 4, 5, 6A, 6B, 7F, 8, 9V, 10A, 11A, 12F, 14, 15A, 15C, 18C, 19A, 19F, 22F, 23B, 23F, 24F, 33F and 35B.

The invention provides a multivalent immunogenic composition comprising 24 distinct *S. pneumoniae* polysaccharide protein conjugates, wherein each of the conjugates comprises a capsular polysaccharide from a *S. pneumoniae* serotype conjugated to a carrier protein, wherein each distinct polysaccharide protein conjugate comprises a polysaccharide from *S. pneumoniae* serotypes 1, 3, 4, 5, 6A, 6B, 7F, 8, 9V, 10A, 11A, 12F, 14, 15A, 15C, 18C, 19A, 19F, 22F, 23B, 23F, 24F, 33F and 35B, respectively, and wherein the carrier protein is CRM197.

The invention provides a multivalent immunogenic composition comprising 24 distinct polysaccharide protein conjugates, wherein each of the conjugates comprises a capsular polysaccharide from a *S. pneumoniae* serotype conjugated to a carrier protein, wherein the polysaccharide are prepared from *S. pneumoniae* serotypes 1, 3, 4, 5, 6A, 6B, 7F, 8, 9V, 10A, 11A, 12F, 14, 15A, 15B, 18C, 19A, 19F, 22F, 23B, 23F, 24F, 33F and 35B.

The invention provides a multivalent immunogenic composition comprising 24 distinct *S. pneumoniae* polysaccharide protein conjugates, wherein each of the conjugates comprises a capsular polysaccharide from a *S. pneumoniae* serotype conjugated to a carrier protein, wherein each distinct polysaccharide protein conjugate comprises a polysaccharide from *S. pneumoniae* serotypes 1, 3, 4, 5, 6A, 6B, 7F, 8, 9V, 10A, 11A, 12F, 14, 15A, 15B, 18C, 19A, 19F, 22F, 23B, 23F, 24F, 33F and 35B, respectively, and wherein the carrier protein is CRM197.

The invention provides a multivalent immunogenic composition comprising up to 33 distinct polysaccharide protein conjugates, wherein each of the conjugates comprises a polysaccharide from a *S. pneumoniae* serotype conjugated to a carrier protein, and wherein the polysaccharide protein conjugates include polysaccharides of a group of *S. pneumoniae* serotypes selected from the group consisting of: 1, 3, 4, 5, 6A, 6B, 7F, 8, 9V, 10A, 11A, 12F, 14, 15A, 15C, 18C, 19A, 19F, 22F, 23B, 23F, 24F, 33F and 35B, further including one, two, three, four, five, six, seven, eight or nine additional *S. pneumoniae* serotypes selected from 7C, 9N, 16F, 21, 23A, 31, 34, 35F and 38.

The invention provides a multivalent immunogenic composition comprising up to 30 distinct polysaccharide protein conjugates, wherein each of the conjugates comprises a polysaccharide from a *S. pneumoniae* serotype conjugated to a carrier protein, and wherein the polysaccharide protein conjugates include polysaccharides of a group of *S. pneumoniae* serotypes selected from the group consisting of: 1, 3, 4, 5, 6A, 6B, 7F, 8, 9V, 10A, 11A, 12F, 14, 15A, 15C, 18C, 19A, 19F, 22F, 23B, 23F, 24F, 33F and 35B, further including one, two, three, four, five or six additional *S. pneumoniae* serotypes selected from 7C, 9N, 16F, 23A, 35F and 38.

The invention provides a multivalent immunogenic composition comprising up to 33 distinct polysaccharide protein conjugates, wherein each of the conjugates comprises a polysaccharide from a S. pneumoniae serotype conjugated to a carrier protein, and wherein the polysaccharide protein conjugates include polysaccharides of a group of S. pneumoniae serotypes selected from the group consisting of: 1, 3, 4, 5, 6A, 6B, 7F, 8, 9V, 10A, 11A, 12F, 14, 15A, 15B, 18C, 19A, 19F, 22F, 23B, 23F, 24F, 33F and 35B, further including one, two, three, four, five, six, seven, eight or nine additional S. pneumoniae serotypes selected from 7C, 9N, 16F, 21, 23A, 31, 34, 35F and 38.

The invention provides a multivalent immunogenic composition comprising up to 30 distinct polysaccharide protein conjugates, wherein each of the conjugates comprises a polysaccharide from a S. pneumoniae serotype conjugated to a carrier protein, and wherein the polysaccharide protein conjugates include polysaccharides of a group of S. pneumoniae serotypes selected from the group consisting of: 1, 3, 4, 5, 6A, 6B, 7F, 8, 9V, 10A, 11A, 12F, 14, 15A, 15B, 18C, 19A, 19F, 22F, 23B, 23F, 24F, 33F and 35B, further including one, two, three, four, five or six additional S. pneumoniae serotypes selected from 7C, 9N, 16F, 23A, 35F and 38.

In some embodiments, at least one of the polysaccharide protein conjugates is formed by a conjugation reaction comprising an aprotic solvent, e.g. dimethylsulfoxide (DMSO). In specific embodiments, each of the polysaccharide protein conjugates is formed by a conjugation reaction comprising an aprotic solvent, e.g. (DMSO).

Also provided are methods for inducing a protective immune response in a human patient comprising administering the multivalent immunogenic compositions of the invention to the patient. In some embodiments of the methods of the invention, the patient was previously treated with a multivalent pneumococcal vaccine.

A multivalent immunogenic composition of the invention may be used as part of a treatment regimen with a different, complementary pneumococcal vaccine. Accordingly, the invention provides a method of inducing a protective immune response in a human patient comprising administering a multivalent immunogenic composition of the invention to the patient, further comprising administering a multivalent pneumococcal vaccine to the patient in any order. In particular embodiments, the multivalent pneumococcal vaccine is comprised of multiple S. pneumoniae polysaccharide protein conjugates wherein each of the conjugates comprises polysaccharide from an S. pneumoniae serotype conjugated to a carrier protein. In other embodiments, the multivalent pneumococcal vaccine is comprised of unconjugated capsular polysaccharides.

The invention also provides multivalent immunogenic compositions comprising S. pneumoniae polysaccharide protein conjugates wherein each of the conjugates comprises a polysaccharide from a S. pneumoniae serotype conjugated to a carrier protein, wherein select serotypes of S. pneumoniae provide cross-reactivity to other select serotypes.

BRIEF DESCRIPTION OF THE DRAWINGS

FIG. 4. OPA dilution titer ratio of PCV22/APA compared to PCV22 unadjuvanted (PCV22 unadj) at PD3.

DETAILED DESCRIPTION OF THE INVENTION

Figure 1:
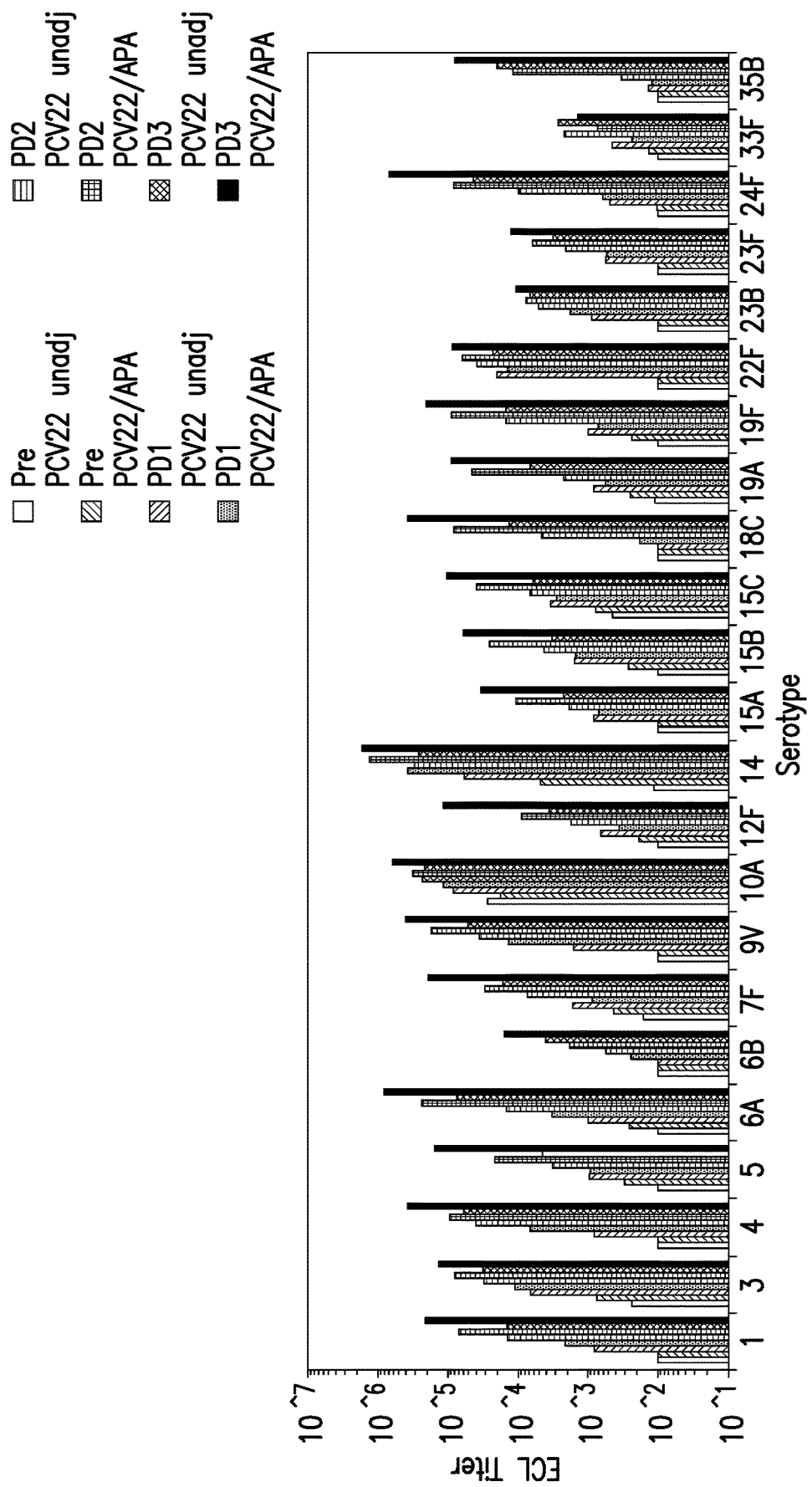
FIG. 1. Pre-immune (Pre), post-dose 1 (PD1), 2 (PD2) and 3 (PD3) IgG antibody dilution titers as determined by ECL for mice immunized with PCV22 unadjuvanted (PCV22 unadj) or formulated with aluminum phosphate adjuvant (PCV22/APA). Reading from left to right; Pre PCV22 unadj, Pre PCV22/APA, PD1 PCV22 unadj, PD1 PCV22/APA, PD2 PCV22 unadj, PD2 PCV22/APA, PD3 PCV22 unadj, and PD3 PCV22/APA.

The present invention provides multivalent immunogenic compositions comprising pneumococcal polysaccharide-protein conjugates, wherein each of the conjugates comprises a polysaccharide from an *S. pneumoniae* serotype conjugated to a carrier protein, wherein the serotypes of *S. pneumoniae* are as defined herein.

In some embodiments the invention provides multivalent immunogenic compositions comprising *S. pneumoniae* polysaccharide protein conjugates, wherein each of the conjugates comprises a polysaccharide from a *S. pneumoniae* serotype conjugated to a carrier protein, and wherein the polysaccharide protein conjugates include polysaccharides of a group of *S. pneumoniae* serotypes selected from the group consisting of:

a) 1, 3, 4, 5, 6A, 6B, 7F, 9V, 10A, 12F, 14, 15A, DeOAc15B, 18C, 19A, 19F, 22F, 23B, 23F, 24F, 33F and 35B;
b) 1, 3, 4, 5, 6A, 6B, 7F, 9V, 10A, 12F, 14, 15A, 15C, 18C, 19A, 19F, 22F, 23B, 23F, 24F, 33F and 35B;
c) 1, 3, 4, 5, 6A, 6B, 7F, 8, 9V, 10A, 12F, 14, 15A, DeOAc15B, 18C, 19A, 19F, 22F, 23B, 23F, 24F, 33F and 35B;
d) 1, 3, 4, 5, 6A, 6B, 7F, 8, 9V, 10A, 12F, 14, 15A, 15C, 18C, 19A, 19F, 22F, 23B, 23F, 24F, 33F and 35B;
e) 1, 3, 4, 5, 6A, 6B, 7F, 8, 9V, 10A, 12F, 14, 15B, 18C, 19A, 19F, 22F, 23B, 23F, 24F, 33F and 35B;
f) 1, 3, 4, 5, 6A, 6B, 7F, 8, 9V, 10A, 11A, 12F, 14, 15A, DeOAc15B, 18C, 19A, 19F, 22F, 23B, 23F, 24F, 33F and 35B;
g) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B;
h) 1, 3, 4, 5, 6A, 6B, 7F, 8, 9V, 10A, 11A, 12F, 14, 15A, 15B, 18C, 19A, 19F, 22F, 23B, 23F, 24F, 33F and 35B;
i) 1, 3, 4, 5, 6A, 6B, 7F, 8, 9V, 10A, 11A, 12F, 14, 15B, 18C, 19A, 19F, 22F, 23B, 23F, 24F, 33F and 35B;
j) 1, 3, 4, 5, 6A, 7F, 9V, 10A, 12F, 14, 15A, 15C, 18C, 19A, 19F, 22F, 23B, 23F, 24F, 33F and 35B;
k) 1, 3, 4, 5, 6B, 7F, 9V, 10A, 12F, 14, 15A, 15C, 18C, 19A, 19F, 22F, 23B, 23F, 24F, 33F and 35B;
l) 1, 3, 4, 5, 6C, 7F, 9V, 10A, 12F, 14, 15A, 15C, 18C, 19A, 19F, 22F, 23B, 23F, 24F, 33F and 35B;
m) 1, 3, 4, 5, 6A, 7F, 8, 9V, 10A, 12F, 14, 15A, 15C, 18C, 19A, 19F, 22F, 23B, 23F, 24F, 33F and 35B;
n) 1, 3, 4, 5, 6B, 7F, 8, 9V, 10A, 12F, 14, 15A, 15C, 18C, 19A, 19F, 22F, 23B, 23F, 24F, 33F and 35B;
o) 1, 3, 4, 5, 6C, 7F, 8, 9V, 10A, 12F, 14, 15A, 15C, 18C, 19A, 19F, 22F, 23B, 23F, 24F, 33F and 35B;
p) 1, 3, 4, 5, 6A, 7F, 8, 9V, 10A, 11A, 12F, 14, 15A, 15C, 18C, 19A, 19F, 22F, 23B, 23F, 24F, 33F and 35B;
q) 1, 3, 4, 5, 6B, 7F, 8, 9V, 10A, 11A, 12F, 14, 15A, 15C, 18C, 19A, 19F, 22F, 23B, 23F, 24F, 33F and 35B;
r) 1, 3, 4, 5, 6C, 7F, 8, 9V, 10A, 11A, 12F, 14, 15A, 15C, 18C, 19A, 19F, 22F, 23B, 23F, 24F, 33F and 35B;
s) 1, 3, 4, 5, 6A, 7F, 9V, 10A, 12F, 14, 15A, 15B, 18C, 19A, 19F, 22F, 23B, 23F, 24F, 33F and 35B;
t) 1, 3, 4, 5, 6B, 7F, 9V, 10A, 12F, 14, 15A, 15B, 18C, 19A, 19F, 22F, 23B, 23F, 24F, 33F and 35B;
u) 1, 3, 4, 5, 6C, 7F, 9V, 10A, 12F, 14, 15A, 15B, 18C, 19A, 19F, 22F, 23B, 23F, 24F, 33F and 35B;
v) 1, 3, 4, 5, 6A, 7F, 8, 9V, 10A, 12F, 14, 15A, 15B, 18C, 19A, 19F, 22F, 23B, 23F, 24F, 33F and 35B;
w) 1, 3, 4, 5, 6B, 7F, 8, 9V, 10A, 12F, 14, 15A, 15B, 18C, 19A, 19F, 22F, 23B, 23F, 24F, 33F and 35B;
x) 1, 3, 4, 5, 6C, 7F, 8, 9V, 10A, 12F, 14, 15A, 15B, 18C, 19A, 19F, 22F, 23B, 23F, 24F, 33F and 35B;
y) 1, 3, 4, 5, 6A, 7F, 8, 9V, 10A, 11A, 12F, 14, 15A, 15B, 18C, 19A, 19F, 22F, 23B, 23F, 24F, 33F and 35B;
z) 1, 3, 4, 5, 6B, 7F, 8, 9V, 10A, 11A, 12F, 14, 15A, 15B, 18C, 19A, 19F, 22F, 23B, 23F, 24F, 33F and 35B;
aa) 1, 3, 4, 5, 6C, 7F, 8, 9V, 10A, 11A, 12F, 14, 15A, 15B, 18C, 19A, 19F, 22F, 23B, 23F, 24F, 33F and 35B;
bb) 1, 3, 4, 5, 6A, 6B, 7F, 9V, 12F, 14, 15A, DeOAc15B, 18C, 19A, 19F, 22F, 23B, 23F, 24F, 33F, 35B and 39;
cc) 1, 3, 4, 5, 6A, 6B, 7F, 9V, 12F, 14, 15A, 15C, 18C, 19A, 19F, 22F, 23B, 23F, 24F, 33F, 35B and 39;
dd) 1, 3, 4, 5, 6A, 6B, 7F, 8, 9V, 12F, 14, 15A, DeOAc15B, 18C, 19A, 19F, 22F, 23B, 23F, 24F, 33F, 35B and 39;
ee) 1, 3, 4, 5, 6A, 6B, 7F, 8, 9V, 12F, 14, 15A, 15C, 18C, 19A, 19F, 22F, 23B, 23F, 24F, 33F, 35B and 39;
ff) 1, 3, 4, 5, 6A, 6B, 7F, 8, 9V, 12F, 14, 15B, 18C, 19A, 19F, 22F, 23B, 23F, 24F, 33F, 35B and 39;
gg) 1, 3, 4, 5, 6A, 6B, 7F, 8, 9V, 11A, 12F, 14, 15A, DeOAc15B, 18C, 19A, 19F, 22F, 23B, 23F, 24F, 33F, 35B and 39;
hh) 1, 3, 4, 5, 6A, 6B, 7F, 8, 9V, 11A, 12F, 14, 15A, 15C, 18C, 19A, 19F, 22F, 23B, 23F, 24F, 33F, 35B and 39;
ii) 1, 3, 4, 5, 6A, 6B, 7F, 8, 9V, 11A, 12F, 14, 15A, 15B, 18C, 19A, 19F, 22F, 23B, 23F, 24F, 33F, 35B and 39;
jj) 1, 3, 4, 5, 6A, 6B, 7F, 8, 9V, 11A, 12F, 14, 15B, 18C, 19A, 19F, 22F, 23B, 23F, 24F, 33F, 35B and 39;
kk) 1, 3, 4, 5, 6A, 7F, 9V, 12F, 14, 15A, 15C, 18C, 19A, 19F, 22F, 23B, 23F, 24F, 33F, 35B and 39;
ll) 1, 3, 4, 5, 6B, 7F, 9V, 12F, 14, 15A, 15C, 18C, 19A, 19F, 22F, 23B, 23F, 24F, 33F, 35B and 39;
mm) 1, 3, 4, 5, 6C, 7F, 9V, 12F, 14, 15A, 15C, 18C, 19A, 19F, 22F, 23B, 23F, 24F, 33F, 35B and 39;
nn) 1, 3, 4, 5, 6A, 7F, 8, 9V, 12F, 14, 15A, 15C, 18C, 19A, 19F, 22F, 23B, 23F, 24F, 33F, 35B and 39;
oo) 1, 3, 4, 5, 6B, 7F, 8, 9V, 12F, 14, 15A, 15C, 18C, 19A, 19F, 22F, 23B, 23F, 24F, 33F, 35B and 39;
pp) 1, 3, 4, 5, 6C, 7F, 8, 9V, 12F, 14, 15A, 15C, 18C, 19A, 19F, 22F, 23B, 23F, 24F, 33F, 35B and 39;
qq) 1, 3, 4, 5, 6A, 7F, 8, 9V, 11A, 12F, 14, 15A, 15C, 18C, 19A, 19F, 22F, 23B, 23F, 24F, 33F, 35B and 39;
rr) 1, 3, 4, 5, 6B, 7F, 8, 9V, 11A, 12F, 14, 15A, 15C, 18C, 19A, 19F, 22F, 23B, 23F, 24F, 33F, 35B and 39;
ss) 1, 3, 4, 5, 6C, 7F, 8, 9V, 11A, 12F, 14, 15A, 15C, 18C, 19A, 19F, 22F, 23B, 23F, 24F, 33F, 35B and 39;
tt) 1, 3, 4, 5, 6A, 7F, 9V, 12F, 14, 15A, 15B, 18C, 19A, 19F, 22F, 23B, 23F, 24F, 33F, 35B and 39;
uu) 1, 3, 4, 5, 6B, 7F, 9V, 12F, 14, 15A, 15B, 18C, 19A, 19F, 22F, 23B, 23F, 24F, 33F, 35B and 39;
vv) 1, 3, 4, 5, 6C, 7F, 9V, 12F, 14, 15A, 15B, 18C, 19A, 19F, 22F, 23B, 23F, 24F, 33F, 35B and 39;
ww) 1, 3, 4, 5, 6A, 7F, 8, 9V, 12F, 14, 15A, 15B, 18C, 19A, 19F, 22F, 23B, 23F, 24F, 33F, 35B and 39;
xx) 1, 3, 4, 5, 6B, 7F, 8, 9V, 12F, 14, 15A, 15B, 18C, 19A, 19F, 22F, 23B, 23F, 24F, 33F, 35B and 39;
yy) 1, 3, 4, 5, 6C, 7F, 8, 9V, 12F, 14, 15A, 15B, 18C, 19A, 19F, 22F, 23B, 23F, 24F, 33F, 35B and 39;
zz) 1, 3, 4, 5, 6A, 7F, 8, 9V, 11A, 12F, 14, 15A, 15B, 18C, 19A, 19F, 22F, 23B, 23F, 24F, 33F, 35B and 39;
aaa) 1, 3, 4, 5, 6B, 7F, 8, 9V, 11A, 12F, 14, 15A, 15B, 18C, 19A, 19F, 22F, 23B, 23F, 24F, 33F, 35B and 39; and bbb) 1, 3, 4, 5, 6C, 7F, 8, 9V, 11A, 12F, 14, 15A, 15B, 18C, 19A, 19F, 22F, 23B, 23F, 24F, 33F, 35B and 39.

In some embodiments, the multivalent immunogenic composition comprises pneumococcal serotypes selected from the group consisting of: i) 1, 3, 4, 5, 6A, 6B, 7F, 9V, 10A, 12F, 14, 15A, 15C, 18C, 19A, 19F, 22F, 23B, 23F, 24F, 33F and 35B; or ii) 1, 3, 4, 5, 6A, 6B, 7F, 8, 9V, 10A, 12F, 14, 15A, 15C, 18C, 19A, 19F, 22F, 23B, 23F, 24F, 33F and 35B; or iii) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B; or iv) 1, 3, 4, 5, 6A, 6B, 7F, 8, 9V, 10A, 11A, 12F, 14, 15A, 15B, 18C, 19A, 19F, 22F, 23B, 23F, 24F, 33F and 35B. In a particular embodiment, a multivalent immunogenic composition of the invention comprises multiple pneumococcal S. pneumoniae polysaccharide protein conjugates wherein each of the conjugates comprises a polysaccharide from an S. pneumoniae serotype conjugated to a carrier protein, wherein the serotypes of S. pneumoniae comprise serotypes: i) 1, 3, 4, 5, 6A, 6B, 7F, 9V, 10A, 12F, 14, 15A, 15C, 18C, 19A, 19F, 22F, 23B, 23F, 24F, 33F and 35B; or ii) 1, 3, 4, 5, 6A, 6B, 7F, 8, 9V, 10A, 12F, 14, 15A, 15C, 18C, 19A, 19F, 22F, 23B, 23F, 24F, 33F and 35B; or iii) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B. Said compositions were found to be immunogenic in mice, rabbits and/or monkeys and generate functional antibody which killed vaccine-type bacterial strains at all doses tested.

The multivalent immunogenic compositions of the invention are useful for immunizing a patient against vaccine-type S. pneumoniae serotypes and/or as part of a treatment regimen with different, complementary pneumococcal vaccine(s). Accordingly, the invention provides a method of inducing a protective immune response in a human patient comprising administering a multivalent immunogenic composition of the invention to the patient, and further comprising administering a multivalent pneumococcal vaccine to the patient, in any order. In other embodiments, the multivalent immunogenic compositions of the invention are administered to a patient who had been previously immunized with a different multivalent pneumococcal vaccine.

In embodiments of the invention, conjugates from at least one pneumococcal serotype are prepared using reductive amination in an aprotic solvent such as DMSO. In further embodiments, the multivalent immunogenic composition comprises pneumococcal conjugates that are each prepared using reductive amination in an aprotic solvent. The use of DMSO solvent enhances the covalent associations of polysaccharide to protein through direct consumption of lysine residues on the surface of the carrier protein. The increased covalent association has a direct benefit to increasing the stability of the polysaccharide protein conjugate of multivalent immunogenic compositions comprising polysaccharide antigens conjugated in DMSO.

I. Definitions and Abbreviations

As used throughout the specification and appended claims, the following abbreviations apply:
APA aluminum phosphate adjuvant
APC antigen presenting cell
CI confidence interval
DMSO dimethylsulfoxide
DS polysaccharide-protein Drug Substance
GMC geometric mean concentration
GMT geometric mean titer
HPSEC high performance size exclusion chromatography
IM intra-muscular or intra-muscularly
IRM infant rhesus macaque
LOS lipo-oligosaccharide
LPS lipopolysaccharide
MALS multi-angle light scattering
MBC monovalent bulk conjugate
Mn number averaged molecular weight
MOPA multiplexed opsonophagocytic assays
MW molecular weight
NMWCO nominal molecular weight cut off
NZWR New Zealand White rabbit
OPA opsonophagocytosis assay
PCV pneumococcal conjugate vaccine
PD1 post-dose 1
PD2 post-dose 2
PD3 post-dose 3
PnPs Pneumococcal Polysaccharide
Ps polysaccharide
PS-20 polysorbate-20
RI refractive index
UV ultraviolet
w/v weight per volume So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

The terms "aqueous solvent" or "aqueous conditions" when used with conjugation, such as reductive amination, refers to use of water as the solvent for the conjugation reaction. The water may contain buffers and other components except that no organic solvent is present.

The terms "aprotic solvent", "DMSO solvent" or "DMSO conditions" when used with conjugation, such as reductive amination, refers to use of an aprotic solvent, or a combination of aprotic solvents, (or DMSO, as applicable) as the solvent for the conjugation reaction. The aprotic solvent may have some water present, for example, up to 1%, 2%, 5%, 10% or 20%.

The term "comprises" when used with the immunogenic composition of the invention refers to the inclusion of any other components, such as adjuvants and excipients, or the addition of one or more polysaccharide-protein conjugates that are not specifically enumerated. The term "consisting of" when used with the multivalent polysaccharide-protein conjugate mixture refers to a mixture having those particular S. pneumoniae polysaccharide protein conjugates and no other S. pneumoniae polysaccharide protein conjugates from a different serotype. "Consists essentially of" and variations such as "consist essentially of" or "consisting essentially of," indicate the inclusion of any recited elements or group of elements, and the optional inclusion of other elements, of similar or different nature than the recited elements, which do not materially change the basic or novel properties of the specified dosage regimen, method, or composition.

"Effective amount" of a composition of the invention refers to a dose required to elicit antibodies that significantly reduce the likelihood or severity of infectivity of a microbe, e.g., S. pneumoniae, during a subsequent challenge.

As used herein, the phrase "indicated for the prevention of pneumococcal disease" means that a vaccine or immunogenic composition is approved by one or more regulatory authorities, such as the US Food and Drug Administration, for the prophylaxis of one or more diseases caused by any serotype of S. pneumoniae, including, but not limited to: pneumococcal disease generally, pneumococcal pneumonia, pneumococcal meningitis, pneumococcal bacteremia, invasive disease caused by S. pneumoniae, and otitis media caused by S. pneumoniae.

A "multivalent pneumococcal vaccine" is a pharmaceutical preparation comprising more than one active agent (e.g., pneumococcal capsular polysaccharide or pneumococcal polysaccharide protein conjugate) that provides active immunity to disease or pathological condition caused by more than one serotype of S. pneumoniae.

The term "polysaccharide" is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like.

The term "unadjuvanted", in the context of a vaccine or immunogenic composition of the instant invention, means a pneumococcal polysaccharide composition, including but not limited to PCV8, PCV15, PCV22, PCV23 and PCV24, wherein the composition contains no adjuvant.

"PCV8" refers to an immunogenic composition containing S. pneumoniae polysaccharide (PnPs) serotypes-8, -10A, -12F, -15A, -15C, -23B, -24F and -35B.

"PCV15" refers to an immunogenic composition containing S. pneumoniae polysaccharide (PnPs) serotypes-1, -3, -4, -5, -6A, -6B, -7F, -9V, -14, -18C, -19A, -19F, -22F, -23F, and -33F.

"PCV22" refers to an immunogenic composition containing S. pneumoniae polysaccharide (PnPs) serotypes-1, -3, -4, -5, -6A, -6B, -7F, -9V, -10A, -12F, -14, -15A, -15C, -18C, -19A, -19F, -22F, -23B, -23F, -24F, -33F, and -35B.

"PCV23" refers to an immunogenic composition containing S. pneumoniae polysaccharide (PnPs) serotypes-1, -3, -4, -5, -6A, -6B, -7F, -8, -9V, -10A, -12F, -14, -15A, -15C, -18C, -19A, -19F, -22F, -23B, -23F, -24F, -33F, and -35B.

"PCV24" refers to an immunogenic composition containing S. pneumoniae polysaccharide (PnPs) serotypes-1, -3, -4, -5, -6A, -6B, -7F, -8, -9V, -10A, -11A, -12F, -14, 15A, -15C, -18C, -19A, -19F, -22F, -23B, -23F, -24F, -33F, and -35B.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. CpG-containing oligonucleotides include modified oligonucleotides using any synthetic internucleoside linkages, modified base and/or modified sugar.

An "adjuvant," as defined herein, is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan.

A "patient" (alternatively referred to herein as a "subject") refers to a mammal capable of being infected with a S. pneumoniae. In preferred embodiments, the patient is a human. A patient can be treated prophylactically or therapeutically. Prophylactic treatment provides sufficient protective immunity to reduce the likelihood or severity of a pneumococcal infection or the effects thereof, e.g., pneumococcal pneumonia. Therapeutic treatment can be performed to reduce the severity or prevent recurrence of a S. pneumoniae infection or the clinical effects thereof. Prophylactic treatment can be performed using a multivalent immunogenic composition of the invention, as described herein. The composition of the invention can be administered to the general population or to those persons at an increased risk of pneumococcal infection, e.g. the elderly, or those who live with or care for the elderly.

Those "in need of treatment" include those previously exposed to or infected with S. pneumoniae, those who were previously vaccinated against S. pneumoniae, as well as those prone to have an infection or any person in which a reduction in the likelihood of infection is desired, e.g., the immunocompromised, the elderly, children, adults, or healthy individuals.

A "stable" multivalent immunogenic composition is a composition which has no significant changes observed at a refrigerated temperature (e.g., 2-8° C. or 4° C.) for at least 1 month, 2 months, 3 months, 6 months, 12 months and/or 24 months. Additionally, a "stable" composition includes one that exhibits desired features at temperatures including at 25° C. and 37° C. for periods including 1 month, 3 months, 6 months, 12 months, and/or 24 months. Typical acceptable criteria for stability are as follows: no more than about 5%, about 10%, about 15%, or about 20% variability in one or more of the following: (a) the number average molecular weight (Mn) of the S. pneumoniae polysaccharide protein conjugates in the composition, (b) weight average molecular weight (Mw) of the S. pneumoniae polysaccharide protein conjugates in the composition, (c) total polysaccharide concentration in the composition, (d) emission maximum of the composition measured using intrinsic protein fluorescence spectroscopy at a particular excitation wavelength, e.g. 280 nanometers, and (e) the fluorescence intensity of the composition measured using intrinsic protein fluorescence spectroscopy at a particular excitation wavelength. The term "stable" may also be used to refer to a particular pneumococcal conjugate within a multivalent immunogenic composition. In such use, the term refers to a conjugate that exhibits the desired properties over time, at a particular temperature, and such properties vary no more that about 5%, about 10%, about 15%, or about 20% over the time and temperature noted.

II. Multivalent Immunogenic Compositions

The invention provides multivalent immunogenic compositions comprising multiple S. pneumoniae polysaccharide protein conjugates wherein each of the conjugates comprises a polysaccharide from an S. pneumoniae serotype conjugated to a carrier protein. Different aspects and embodiments of the multivalent immunogenic compositions of the invention are described, infra.

In one embodiment (Embodiment E1), the invention provides a multivalent immunogenic composition comprising multiple S. pneumoniae polysaccharide protein conjugates, each comprising capsular polysaccharide from an S. pneumoniae serotype conjugated to a carrier protein, wherein the serotypes of S. pneumoniae comprise, consist, or consist essentially of: i) 1, 3, 4, 5, 6A, 6B, 7F, 9V, 10A, 12F, 14, 15A, 15C, 18C, 19A, 19F, 22F, 23B, 23F, 24F, 33F and 35B or ii) 1, 3, 4, 5, 6A, 6B, 7F, 8, 9V, 10A, 12F, 14, 15A, 15C, 18C, 19A, 19F, 22F, 23B, 23F, 24F, 33F and 35B or iii) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B. In sub-embodiments of Embodiment E1, the immunogenic composition does not comprise any further *S. pneumoniae* polysaccharide protein conjugates.

As used herein, de-O-acetylated serotype 15B (DeOAc15B) pneumococcal polysaccharide is substantially equivalent to serotype 15C pneumococcal polysaccharide and has a substantially identical NMR spectra (data not shown). As used herein, de-O-acetylated serotype 15B pneumococcal polysaccharide and serotype 15C pneumococcal polysaccharide may each have an O-Acetyl content per repeating unit in the range of 0-5%, or in the range of 0-4%, or in the range of 0-3%, or in the range of 0-2%, or in the range of 0-1%, or in the range of 0-0.5%, or in the range of 0-0.1%, or no O-acetyl content. In a report by Spencer B. L., et al., pneumococcal polysaccharide 15C may be slightly O-acetylated (Spencer, B. L. et al., Clin. Vac. Immuno. (2017) 24(8): 1-13). Thus, in any of the embodiments of the multivalent immunogenic compositions herein, de-O-acetylated serotype 15B (DeOAc15B) can be used in place of serotype 15C. Processes for de-O-acetylation are known in the art, for example as described in Rajam et al., *Clinical and Vaccine Immunology*, 2007, 14(9):1223-1227.

In certain embodiments of any of the multivalent immunogenic compositions of the invention, including Embodiment E1 and any sub-embodiment thereof, the composition further comprises a pharmaceutically acceptable carrier.

Cross-Reactivity

In an embodiment the invention provides multivalent immunogenic compositions comprising *S. pneumoniae* polysaccharide protein conjugates wherein each of the conjugates comprises a polysaccharide from a *S. pneumoniae* serotype, including serotype 6C, conjugated to a carrier protein, wherein serotype 6C of *S. pneumoniae* provides cross-reactivity against serotypes 6A and 6B of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 6A, conjugated to a carrier protein, wherein serotype 6A of *S. pneumoniae* provides cross-protection against serotypes 6B and/or 6C of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 6B, conjugated to a carrier protein, wherein serotype 6B of *S. pneumoniae* provides cross-protection against serotypes 6A and/or 6C of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 15C, conjugated to a carrier protein, wherein serotype 15C of *S. pneumoniae* provides cross-protection against serotype 15B of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 15B, conjugated to a carrier protein, wherein serotype 15B of *S. pneumoniae* provides cross-protection against serotype 15C of *S. pneumoniae*.

Carrier Protein

In particular embodiments of the present invention, CRM197 is used as the carrier protein. CRM197 is a non-toxic variant (i.e., toxoid) of diphtheria toxin having the following sequence of amino acids:

```
                                             (SEQ ID NO: 1)
GADDVVDSSK SFVMENFSSY HGTKPGYVDS

IQKGIQKPKS GTQGNYDDDW

KEFYSTDNKY DAAGYSVDNE NPLSGKAGGV

VKVTYPGLTK VLALKVDNAE

TIKKELGLSL TEPLMEQVGT EEFIKRFGDG

ASRVVLSLPF AEGSSSVEYI

NNWEQAKALS VELEINFETR GKRGQDAMYE

YMAQACAGNR VRRSVGSSLS

CINLDWDVIR DKTKTKIESL KEHGPIKNKM

SESPNKTVSE EKAKQYLEEF

HQTALEHPEL SELKTVTGTN PVFAGANYAA

WAVNVAQVID SETADNLEKT

TAALSILPGI GSVMGIADGA VHHNTEEIVA

QSIALSSLMV AQAIPLVGEL

VDIGFAAYNF VESIINLFQV VHNSYNRPAY

SPGHKTQPFL HDGYAVSWNT

VEDSIIRTGF QGESGHDIKI TAENTPLPIA

GVLLPTIPGK LDVNKSKTHI

SVNGRKIRMR CRAIDGDVTF CRPKSPVYVG

NGVHANLHVA FHRSSSEKIH

SNEISSDSIG VLGYQKTVDH TKVNSKLSLF FEIKS
```

In one embodiment, CRM197 is isolated from cultures of *Corynebacterium diphtheria* strain C7 ((3197) grown in casamino acids and yeast extract-based medium. In another embodiment, CRM197 is prepared recombinantly in accordance with the methods described in U.S. Pat. No. 5,614,382. Typically, CRM197 is purified through a combination of ultra-filtration, ammonium sulfate precipitation, and ion-exchange chromatography. In some embodiments, CRM197 is prepared in *Pseudomonas fluorescens* using Pfenex Expression Technology™ (Pfenex Inc., San Diego, CA).

Other suitable carrier proteins include additional inactivated bacterial toxins such as DT (Diphtheria toxoid) or fragment B of DT (DTFB), TT (tetanus toxid) or fragment C of TT, pertussis toxoid, cholera toxoid (e.g., as described in WO 2004/083251), *E. coli* LT, *E. coli* ST, and exotoxin A from *Pseudomonas aeruginosa*. Bacterial outer membrane proteins such as outer membrane protein complex (OMPC), porins, transferrin binding proteins, pneumococcal surface protein A (PspA; See WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, *Infect Immun* 63; 2706-13) including ply detoxified in some fashion for example dPLY-GMBS (See WO 04/081515) or dPLY-formol, PhtX, including PhtA, PhtB, PhtD, PhtE and fusions of Pht proteins for example PhtDE fusions, PhtBE fusions (See WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., EP 0 594 610 B), or immunologically functional equivalents thereof, synthetic peptides (See EP0378881 and EP0427347), heat shock proteins (See WO 93/17712 and WO 94/03208), pertussis proteins (See WO 98/58668 and EP0471177), cytokines, lymphokines, growth factors or hormones (See WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See WO 01/72337), toxin A or B of *C. difficile* (See WO 00/61761), and flagellin (See Ben-Yedidia et al., 1998, *Immunol Lett* 64:9) can also be used as carrier proteins.

Other DT mutants can be used as the carrier protein, such as CRM176, CRM228, CRM45 (Uchida et al., 1973, *J Biol Chem* 218:3838-3844); CRM9, CRM45, CRM102, CRM103 and CRM107 and other mutations described by Nicholls and Youle in *Genetically Engineered* Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711. Such DT mutants can also be used to make DTFB variants where the variants comprise the B fragment contain the epitope regions.

In certain embodiments, the carrier protein is selected from the group consisting of: Outer Membrane Protein Complex (OMPC), tetanus toxoid, diphtheria toxoid, protein D and CRM197.

In some embodiments of the invention, a second carrier can be used for one or more of the polysaccharide protein conjugates in the multivalent immunogenic composition. The second carrier protein is preferably a protein that is non-toxic and non-reactogenic and obtainable in sufficient amount and purity. The second carrier protein is also conjugated or joined with the *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

In embodiments of the invention, including Embodiment E1 and any sub-embodiment thereof, one or more (including 2, 3, 4, 5, 6, 7, 8, 9, 10, 11, 12, 13, 14, 15, 16, 17, 18, 19, 20, 21, 22, 23, 24, 25, 26, 27, 28, 29, 30 or more, where applicable) of the polysaccharide serotypes is conjugated to CRM197. In further embodiments of the invention, including Embodiment E1 and any sub-embodiment thereof, each of the polysaccharide serotypes is conjugated to CRM197.

Formulation of the polysaccharide-protein conjugates of the present invention can be accomplished using art-recognized methods. For instance, individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

In some embodiments of the invention, the multivalent immunogenic composition comprises multiple *S. pneumoniae* polysaccharide protein conjugates comprising capsular polysaccharide from an *S. pneumoniae* serotype conjugated to a carrier protein and an adjuvant, wherein the *S. pneumoniae* serotypes are as described herein. Suitable adjuvants to enhance effectiveness of the composition include, but are not limited to:

(1) aluminum salts (alum), such as aluminum hydroxide, aluminum phosphate, aluminum sulfate, etc.;
(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, MT) containing 2% Squalene, 0.2% Tween 80, and one or more bacterial cell wall components from the group consisting of 3-O-deacylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;
(3) saponin adjuvants, such as Quil A or STIMULON™ QS-21 (Antigenics, Framingham, MA) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);
(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-β-D-glucopyranoside, which is also known as 529 (formerly known as RC529), which is formulated as an aqueous form or as a stable emulsion
(5) synthetic polynucleotides such as oligonucleotides containing CpG motif(s) (U.S. Pat. No. 6,207,646);
(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetylmuramyl-L-threonyl-D-isoglutamine (thr-MDP), N-acetyl-normuramyl-L-alanine-2-(1', 2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, Superfos, Amphogel, aluminum (III) hydroxide, aluminum hydroxyphosphate sulfate, Aluminum Phosphate Adjuvant (APA), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized. In one embodiment, the dose of the aluminum salt is 10, 15, 20, 25, 30, 50, 70, 100, 125, 150, 200, 300, 500, or 700 µg, or 1, 1.2, 1.5, 2, 3, 5 mg or more. In yet another embodiment, the dose of alum salt described above is per µg of recombinant protein.

In certain embodiments, a commercially available Al(OH)$_3$ (e.g. Alhydrogel or Superfos of Denmark/Accurate Chemical and Scientific Co., Westbury, NY) is used to adsorb proteins in a ratio of 50-200 µg protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of antigen that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted to target 4 µg/mL for all serotypes except 6B, which may be diluted to target 8 µg/mL. Once diluted, the batch will be filter sterilized, and an equal volume of aluminum phosphate adjuvant added aseptically to target a final aluminum concentration of 250 µg/mL. The adjuvanted, formulated batch will be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

In alternative embodiments, the immunogenic composition comprises multiple S. pneumoniae polysaccharide protein conjugates as described herein, for example in Embodiment E1 or any sub-embodiment thereof, and does not comprise an adjuvant.

Formulations

The multivalent immunogenic compositions of the invention can be formulated as single dose vials, multi-dose vials or as pre-filled glass or plastic syringes.

In another embodiment, the multivalent immunogenic compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The multivalent immunogenic compositions of the instant invention may be isotonic, hypotonic or hypertonic. However, it is often preferred that a composition for infusion or injection be essentially isotonic, when administrated. Hence, for storage, a composition may preferably be isotonic or hypertonic. If the composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, CaCl$_2$), KCl and MgCl$_2$. Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may, for example, be selected from the group consisting of TRIS, acetate, glutamate, lactate, maleate, tartrate, phosphate, citrate, carbonate, glycinate, histidine, glycine, succinate and triethanolamine buffer.

The buffer may be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the invention may also contain a surfactant. Preferred surfactants include, but are not limited to: Poloxamer-188 (P188; Pluronic; F68 NF), the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as PS-80) of from 0.01 to 1%, in particular about 0.1%; octyl- or nonylphenoxy polyoxyethanols (such as Triton X-100, or other detergents in the Triton series) of from 0.001 to 0.1%, in particular 0.005 to 0.02%; polyoxyethylene ethers (such as laureth 9) of from 0.1 to 20%, preferably 0.1 to 10% and in particular 0.1 to 1% or about 0.5%.

In certain embodiments, the composition consists essentially of histidine (20 mM), saline (150 mM) and 0.2% PS-20 at a pH of 5.8 with 250 µg/mL of APA (Aluminum Phosphate Adjuvant). PS-20 can range from 0.005% to 0.3% (w/v). In another embodiment, PS-20 can range from 0.025% to 0.8% (w/v). In another embodiment, PS-20 can range from 0.05% to 0.8% (w/v). In another embodiment, PS-20 can range from 0.05% to 0.2% (w/v). The process consists of combining a blend of up to 24 serotypes in histidine, saline, and PS-20, then combining this blended material with APA and saline with or without antimicrobial preservatives.

In particular embodiments, the multivalent immunogenic composition comprises S. pneumoniae polysaccharide protein conjugates wherein each of the conjugates comprises a polysaccharide from an S. pneumoniae serotype conjugated to a carrier protein, wherein the serotypes of S. pneumoniae in the polysaccharide protein conjugates comprise any of the sets of serotypes set forth herein, and further comprises 20-80 mM histidine pH 5.8 and 150 mM NaCl. In some embodiments, the multivalent immunogenic composition further comprises from 0.2% to 0.8% w/v polysorbate 20.

The multivalent immunogenic composition PCV24 is prepared by individually conjugating the CRM197 protein to S. pneumoniae polysaccharide (PnPs) serotypes-1, -3, -4, -5, -6A, -6B, -7F, -8, -9V, -10A, -11A, -12F, -14, -15A, -15C, -18C, -19A, -19F, -22F, -23B, -23F, -24F, -33F, and -35B using reductive amination in an aprotic solvent (also referred to as DMSO chemistry) and formulated in 20 mM L-Histidine pH 5.8, 150 mM NaCl and 0.1% w/v Polysorbate-20 (PS-20) at 4 µg/mL or 8 µg/mL of each polysacchardide serotype for a total polysaccharide concentration of 96 µg/mL or 192 µg/mL, respectively, and referred to as "PCV24 unadj". In another specific embodiment, the multivalent immunogenic composition PCV24 is prepared in 20 mM L-Histidine pH 5.8, 150 mM NaCl and 0.2% w/v Polysorbate-20 (PS-20) at 4 µg/mL of each polysaccharide serotype for a total polysaccharide concentration of 96 µg/mL further comprising 250 µg [Al]/mL in the form of Aluminum Phosphate Adjuvant. This is referred to as "PCV24/APA".

The choice of surfactant may need to be optimized for different drug products and drug substances. For multivalent vaccines having 15 or more serotypes, PS-20 and P188 are preferred. The choice of chemistry used to make conjugates can also play an important role in the stabilization of the formulation. In particular, when the conjugation reactions used to prepare different polysaccharide protein conjugates in a multivalent composition include both aqueous solvent and DMSO solvent, particular surfactant systems provide significant differences in stability. Improved stability of polysacharide protein conjugates was seen with polysorbate 20 alone or with poloxamer 188 in combination with a polyol.

The exact mechanism of how a specific detergent protects a biotherapeutic is poorly understood and cannot be predicted a priori. Possible stabilization mechanisms include preferential hydration, preferential exclusion, air/liquid interface competition between biotherapeutic and surface, surface tension, and/or direct association of the detergent with the biotherapeutic to mask hydrophobic patches which serve as seeds for aggregation.

Poloxamer may also be used in the compositions of the invention. A poloxamer is a nonionic triblock copolymer composed of a central hydrophobic chain of polyoxypropylene (poly(propylene oxide)) flanked by two hydrophilic chains of polyoxyethylene (poly(ethylene oxide)). Poloxamers are also known by the tradename Pluronic®. Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic® with a polyoxypropylene molecular mass of 1,800 g/mol and a 10% polyoxyethylene content). See U.S. Pat. No. 3,740,421.

Examples of poloxamers have the general formula: $HO(C_2H_4O)_a(C_3H_6O)_b(C_2H_4O)_aH$, wherein a and b blocks have the following values:

| Pluronic ® | Poloxamer | A | B | Molecular Weight |
|---|---|---|---|---|
| L31 | | 2 | 16 | 1100 (average) |
| L35 | | | | 1900 (average) |
| L44NF | 124 | 12 | 20 | 2090 to 2360 |
| L64 | | | | 2900 (average) |
| L81 | | | | 2800 (average) |
| L121 | | | | 4400 (average) |
| P123 | | 20 | 70 | 5750 (average) |
| F68NF | 188 | 80 | 27 | 7680 to 9510 |
| F87NF | 237 | 64 | 37 | 6840 to 8830 |
| F108NF | 338 | 141 | 44 | 12700 to 17400 |
| F127NF | 407 | 101 | 56 | 9840 to 14600 |

Molecular weight units, as used herein, are in Dalton (Da) or g/mol.

Preferably, the poloxamer generally has a molecular weight in the range from 1,100 to 17,400 Da, from 7,500 to 15,000 Da, or from 7,500 to 10,000 Da. The poloxamer can be selected from poloxamer 188 or poloxamer 407. The final concentration of the poloxamer in the formulations is from 0.001% to 5% weight/volume, or 0.025% to 1% weight/volume. In certain aspects, the polyol is propylene glycol and is at final concentration from 1% to 20% weight/volume. In certain aspects, the polyol is polyethylene glycol 400 and is at final concentration from 1% to 20% weight/volume.

Suitable polyols for the formulations of the invention are polymeric polyols, particularly polyether diols including, but are not limited to, propylene glycol and polyethylene glycol, Polyethylene glycol monomethyl ethers. Propylene glycol is available in a range of molecular weights of the monomer from ~425 to ~2,700. Polyethylene glycol and Polyethylene glycol monomethyl ether is also available in a range of molecular weights ranging from ~200 to ~35,000 including but not limited to PEG200, PEG300, PEG400, PEG1000, PEG MME 550, PEG MME 600, PEG MME 2000, PEG MME 3350 and PEG MME 4000. A preferred polyethylene glycol is polyethylene glycol 400. The final concentration of the polyol in the formulations of the invention may be 1% to 20% weight/volume or 6% to 20% weight/volume.

The formulation also contains a pH-buffered saline solution. The buffer may, for example, be selected from the group consisting of TRIS, acetate, glutamate, lactate, maleate, tartrate, phosphate, citrate, carbonate, glycinate, histidine, glycine, succinate, HEPES (4-(2-hydroxyethyl)-1-piperazineethanesulfonic acid), MOPS (3-(N-morpholino)propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspect of the invention, the buffer is selected from the group consisting of phosphate, succinate, histidine, MES, MOPS, HEPES, acetate or citrate. The buffer may furthermore, for example, be selected from USP compatible buffers for parenteral use, in particular, when the pharmaceutical formulation is for parenteral use. In one embodiment, the concentration of buffer will range from 1 mM to 100 mM. In another embodiment, the concentration of buffer will range from 10 mM to 80 mM. In another embodiment, the concentration of buffer will range from 1 mM to 50 mM, or 5 mM to 50 mM. In certain aspects, the buffer is histidine at a final concentration of 5 mM to 50 mM, or succinate at a final concentration of 1 mM to 10 mM. In certain aspects, the histidine buffer is at a final concentration of 20 mM±2 mM.

While the saline solution (e.g., a solution containing NaCl) is preferred, other salts suitable for formulation include but are not limited to, $CaCl_2$), KCl and $MgCl_2$ and combinations thereof. Non-ionic isotonic agents including but not limited to sucrose, trehalose, mannitol, sorbitol and glycerol may be used in lieu of a salt. Suitable salt ranges include, but are not limited to 20 mM to 500 mM or 40 mM to 170 mM. In one aspect, the saline is NaCl, optionally present at a concentration from 25 mM to 170 mM.

In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The amount of conjugate in each dose of the composition is selected as an amount that induces an immunoprotective response without significant, adverse effects. Such amount can vary depending upon the pneumococcal serotype. Generally, for polysaccharide-based conjugates, each dose will comprise 0.08 to 100 ☐g of each polysaccharide. In some embodiments of the invention, the dose of each polysaccharide conjugate is from 0.08 to 10 ☐g. In further embodiments, the dose of each conjugate is from 1 to 5 ☐g, from 0.4 to 4 ☐g, from 0.4 to 3 ☐g, from 0.4 to 2 ☐g, or from 0.4 to 1 ☐g. In some embodiments, the dose of one or more polysaccharide conjugates is 100, 150, 200, 250, 300, 400, 500, or 750 ng or 0.4, 0.5, 0.6, 0.7, 0.75, 0.8, 0.9, 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 ☐g.

In some embodiments of the compositions of the invention, all of the polysaccharide conjugates are present in the composition in the same amount. In further embodiments, the polysaccharide conjugates are present in the composition in different amounts (i.e., at least one polysaccharide conjugate is present in an amount that is different than one or more of the other polysaccharide conjugates of the composition).

Optimal amounts of components for a particular immunogenic composition can be ascertained by standard studies involving observation of appropriate immune responses in subjects. For example, in another embodiment, the dosage for human vaccination is determined by extrapolation from animal studies to human data. In another embodiment, the dosage is determined empirically.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761.

In certain embodiments, the compositions of the invention are administered to a subject by one or more methods known to a person skilled in the art, such as parenterally, transmucosally, transdermally, intramuscularly, intravenously, intra-dermally, intra-nasally, subcutaneously, intra-peritonealy, and formulated accordingly. In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

III. Methods of Making

Capsular polysaccharides from *Streptococcus pneumoniae* can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, each pneumococcal polysaccharide serotype is grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity in polysaccharide samples and/or to improve filterability for conjugated products using techniques such as mechanical or chemical sizing. Chemical hydrolysis may be conducted using acetic acid. Mechanical sizing may be conducted using High Pressure Homogenization Shearing.

The purified polysaccharides can be chemically activated to make the saccharides capable of reacting with the carrier protein. The purified polysaccharides can be connected to a linker. Once activated or connected to a linker, each capsular polysaccharide is separately conjugated to a carrier protein to form a glycoconjugate. The polysaccharide conjugates may be prepared by known coupling techniques.

The polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

The polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

The coupling can also take place indirectly, i.e. with an additional linker that is used to derivatise the polysaccharide prior to coupling to the linker.

The polysaccharide is coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker. The reaction results in a polysaccharide-additional linker intermediate in which the polysaccharide is coupled to the additional linker via a C—N linkage.

The polysaccharide can be coupled to the additional linker using a different group in the polysaccharide, particularly a carboxyl group. This coupling comprises two steps: (a1) reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

In one embodiment, the chemical activation of the polysaccharides and subsequent conjugation to the carrier protein by reductive amination can be achieved by means described in U.S. Pat. Nos. 4,365,170, 4,673,574 and 4,902,506, U.S. Patent Application Publication Nos. 2006/0228380, 2007/184072, 2007/0231340 and 2007/0184071, and WO2006/110381, WO2008/079653, and WO2008/143709. The chemistry may include the activation of pneumococcal polysaccharide by reaction with any oxidizing agent which oxidizes a terminal hydroxyl group to an aldehyde, such as periodate (including sodium periodate, potassium periodate, or periodic acid). The reaction leads to a random oxidative cleavage of vicinal hydroxyl groups of the carbohydrates with the formation of reactive aldehyde groups.

Coupling to the carrier protein is by reductive amination via direct amination to the lysyl groups of the protein. For example, conjugation can be carried out by reacting a mixture of the activated polysaccharide and carrier protein with a reducing agent such as sodium cyanoborohydride. The conjugation reaction may take place under aqueous solution or in the presence of DMSO. See, e.g., US2015/0231270, US2011/0195086 and EP 0471 177 B1. Unreacted aldehydes are then capped with the addition of a strong reducing agent, such as sodium borohydride.

Reductive amination involves two steps, (1) oxidation of the polysaccharide to form reactive aldehydes, (2) reduction of the imine (Schiff base) formed between activated polysaccharide and a carrier protein to form a stable amine conjugate bond. Before oxidation, the polysaccharide is optionally size reduced. Mechanical methods (e.g. homogenization) or chemical hydrolysis may be employed. Chemical hydrolysis may be conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^-$) and includes the various salts of periodate (e.g., sodium periodate and potassium periodate). In an embodiment the capsular polysaccharide is oxidized in the presence of metaperiodate, preferably in the presence of sodium periodate ($NaIO_4$). In another embodiment the capsular polysaccharide is oxidized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chlorosuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In certain aspects, the oxidizing agent is 2,2,6,6-Tetramethyl-1-piperidinyloxy (TEMPO) free radical and N-Chlorosuccinimide (NCS) as the cooxidant (as described in WO 2014/097099). Therefore in one aspect, the glycoconjugates from S. pneumoniae are obtainable by a method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent maybe selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

In certain embodiments, the instant invention provides a method for preparing a serotype 8 Streptococcus pneumoniae polysaccharide-protein conjugate utilizing a conjugation reaction in an aprotic solvent, wherein the conjugation reaction does not use cyanoborohydride. In further embodiments, the conjugation reaction is a Schiff base reduction or reductive amination. In further embodiments, the protein is tetanus toxoid, diphtheria toxoid, or CRM197. In still further embodiments the protein is CRM197. In further embodiments, the conjugation reaction is reductive amination. In further embodiments, the reductive amination is performed in dimethylsulfoxide (DMSO).

In some embodiments, the oxidized polysaccharides before conjugation have a molecular weight of between 30 kDa and 1,000 kDa. Molecular weight can be calculated by size exclusion chromatography (SEC) combined with multiangle light scattering detector (MALS) and refractive index detector (RI). In some embodiments, the polysaccharide has a molecular weight of between 50 kDa and 300 kDa. In some embodiments, the polysaccharide has a molecular weight of between 50 kDa and 1,000 kDa. In additional embodiments, the polysaccharide has a molecular weight of between 70 kDa and 900 kDa. In other embodiments, the polysaccharide has a molecular weight of between 100 kDa and 800 kDa. In other embodiments, the polysaccharide has a molecular weight of between 200 kDa and 600 kDa. In further embodiments, the polysaccharide has a molecular weight of 100 kDa to 1,000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; or 500 kDa to 600 kDa.

The second step of the conjugation process is the reduction of the imine (Schiff base) bond between activated polysaccharide and a carrier protein to form a stable conjugate bond (so-called reductive amination), using a reducing agent. Reducing agents which are suitable include the cyanoborohydrides (such as sodium cyanoborohydride or sodium borohydride). In one embodiment the reducing agent is sodium cyanoborohydride.

In certain embodiments, the reductive amination reaction is carried out in aprotic solvent (or a mixture of aprotic solvents). In one embodiment, the reduction reaction is carried out in DMSO or in DMF (dimethylformamide) solvent. The DMSO or DMF solvent may be used to reconstitute the activated polysaccharide and carrier protein, if lyophilized. In one embodiment, the aprotic solvent is DMSO.

At the end of the reduction reaction, there may be unreacted aldehyde groups remaining in the conjugates, which may be capped using a suitable capping agent. In one embodiment this capping agent is sodium borohydride ($NaBH_4$). Suitable alternatives include sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN-$BH_3$, benzylamine-$BH_3$ or 5-ethyl-2-methylpyridine borane (PEMB) or borohydride exchange resin. Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration, precipitation/elution, column chromatography (ion exchange chromatography, multimodal ion exchange chromatography, DEAE, or hydrophobic interaction chromatography), and depth filtration. In an embodiment, the glycoconjugates are purified by diafiltration or ion exchange chromatography or size exclusion chromatography.

Glycoconjugates prepared using reductive amination in an aprotic solvent are generally used in multivalent pneumococcal conjugate vaccines. Thus, in certain embodiments for multivalent compositions where not all the serotypes are prepared in an aprotic solvent, the reduction reaction for the remaining seroytpes is carried out in aqueous solvent (e.g., selected from PBS (phosphate buffered saline), MES (2-(N-morpholino)ethanesulfonic acid), HEPES (4-(2-hydroxyethyl)-1-piperazineethanesulfonic acid), Bis-tris, ADA (N-(2-Acetamido)iminodiacetic acid), PIPES (piperazine-N,N'-bis(2-ethanesulfonic acid)), MOPSO (3-Morpholino-2- hydroxypropanesulfonic acid), BES (N,N-bis(2-hydroxyethyl)-2-aminoethanesulfonic acid), MOPS (3-(N-morpholino)propanesulfonic acid), DIPSO (3-Bis(2-hydroxyethyl) amino-2-hydroxypropane-1-sulfonic acid), MOBS (4-(N-morpholino)butanesulfonic acid), HEPPSO (N-(2-Hydroxyethyl)piperazine-N'-(2-hydroxypropane-sulfonic acid)), POPSO (Piperazine-1,4-bis(2-hydroxy-3-propanesulfonic acid)), TEA (triethanolamine), EPPS (4-(2-Hydroxyethyl)piperazine-1-propanesulfonic acid), or Bicine at a pH between 6.0 and 8.5, 7.0 and 8.0, or 7.0 and 7.5).

S. pneumoniae capsular polysaccharide-protein conjugates that can be prepared using reductive amination in an aprotic solvent, include, but are not limited to, S. pneumoniae serotypes: 1, 3, 4, 5, 6A, 6B, 6C, 7F, 8, 9V, 10A, 11A, 12F, 14, 15A, 15B, 15C, 18C, 19A, 19F, 22F, 23B, 23F, 24F, 33F and 35B. The polysaccharides may be used in the form of oligosaccharides. These are conveniently formed by fragmentation of purified polysaccharide (e.g. by hydrolysis), which will usually be followed by purification of the fragments of the desired size.

In certain embodiments, pneumococcal polysaccharide-protein conjugates of one or more of the S. pneumoniae serotypes 1, 3, 4, 5, 6A, 6B, 6C, 7F, 8, 9V, 10A, 11A, 12F, 14, 15A, 15B, 15C, 18C, 19A, 19F, 22F, 23B, 23F, 24F, 33F and 35B are prepared using reductive amination in an aprotic solvent. In certain embodiments, each of the conjugates in the multivalent immunogenic composition is prepared using reductive amination in an aprotic solvent. In certain embodiments, polysaccharides of one or more serotypes in a multivalent composition of the invention are conjugated to a carrier protein using reductive amination in an aprotic solvent and polysaccharides of one or more serotypes are conjugated using reductive amination in an aqueous solvent. In certain embodiments, polysaccharides of two or more serotypes in a multivalent composition of the invention are conjugated to a carrier protein using reductive amination in an aprotic solvent. In other embodiments, polysaccharides of three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, or twenty-four or more serotypes in a multivalent composition of the invention are conjugated to a carrier protein using reductive amination in an aprotic solvent. In certain embodiments, polysaccharides from one or more serotypes in a multivalent composition of the invention are conjugated to a carrier protein using other chemistries which may be in an aprotic solvent or in an aqueous solvent.

Thus, the invention relates to a multivalent immunogenic composition comprising multiple S. pneumoniae polysaccharide protein conjugates, each comprising capsular polysaccharide from an S. pneumoniae serotype conjugated to a carrier protein, wherein the serotypes of S. pneumoniae are as described herein (i.e. in Section II, "Multivalent Immunogenic Compositions"), wherein the conjugation reaction whereby the S. pneumonia polysaccharide of one or more of the polysaccharide protein conjugates is conjugated to the carrier protein is in an aprotic solvent. In certain embodiments, at least 30%, 35%, 40%, 45%, 50%, 55%, 60%, 65%, 70%, 75%, 80%, 85%, 90%, 95%, or 100% of the pneumococcal serotypes in a multivalent immunogenic composition are conjugated in an aprotic solvent. The remainder of the serotypes are conjugated using an alternative chemistry and/or in an aqueous solvent.

It was determined that the use of DMSO as a solvent during reductive amination of polysaccharide-protein conjugates results in the unexpectedly superior stability and enhanced immunogenicity for those serotypes relative to the same conjugates prepared under aqueous conditions (See US Application Serial No's. 62/463,216 and 62/555,444).

In certain embodiments of the invention the total polysaccharide concentration in the composition is from about 0.02 to about 0.288 mg/mL. In certain embodiments of the invention the total polysaccharide concentration in the composition is from about 0.03 to about 0.192 mg/mL. In certain embodiments of the invention the total polysaccharide concentration in the composition is from about 0.04 to about 0.192 mg/mL. In other embodiments, the total polysaccharide concentration in the composition is from about 0.065 to about 0.096 mg/mL, about 0.070 to about 0.080 mg/mL, about 0.065 to about 0.080 mg/mL, about 0.070 to about 0.085 mg/mL, about 0.110 to about 0.128 mg/mL, about 0.110 to about 0.175 mg/mL, about 0.10 to about 0.175 mg/mL, about 0.110 to about 0.170 mg/mL, about 0.115 to about 0.15 mg/mL, about 0.110 to about 0.15 mg/mL, about 0.110 to about 0.125 mg/mL, about 0.150 to about 0.170 mg/mL, about 0.150 to about 0.165 mg/mL, about 0.140 to about 0.170 mg/mL, about 0.130 to about 0.170 mg/mL, about 0.150 to about 0.175 mg/mL, about 0.070 to about 0.170 mg/mL, about 0.065 to about 0.175 mg/mL, or about 0.065 to about 0.180 mg/mL.

In embodiments of the invention wherein one or more, or all, of the polysaccharide-protein conjugates in the multivalent immunogenic compositions are prepared in an aprotic solvent, the total polysaccharide concentration in the composition is stable for 4 weeks or more at 37° C., 4 weeks or more at 25° C., or 12 weeks or more at 4° C.

In certain embodiments of the invention wherein one or more, or all, of the polysaccharide-protein conjugates in the multivalent immunogenic compositions are prepared in an aprotic solvent, the average molecular weight (Mw) of all of the S. pneumoniae polysaccharide protein conjugates in the composition (average of all conjugates in the composition) is from about 2,000 to about 6,500 kDa, from about 2,500 to about 6,000 kDa, from about 3,000 to about 5,500 kDa, from about 3,500 to about 5,000 kDa, from about 3,500 to about 4,500 kDa, from about 3,500 to about 4,700 kDa, from about 3,500 to about 4,600 kDa, from about 3,500 to about 4,500 kDa, from about 3,500 to about 4,400 kDa, from about 3,500 to about 4,300 kDa, from about 3,500 to about 4,200 kDa, from about 3,600 to about 4,700 kDa, from about 3,600 to about 4,600 kDa, from about 3,600 to about 4,500 kDa, from about 3,600 to about 4,400 kDa, from about 3,600 to about 4,300 kDa, from about 3,600 to about 4,200 kDa, from about 3,700 to about 4,700 kDa, from about 3,700 to about 4,600 kDa, from about 3,700 to about 4,500 kDa, from about 3,700 to about 4,400 kDa, from about 3,700 to about 4,300 kDa, from about 3,700 to about 4,200 kDa, from about 3,800 to about 4,700 kDa, from about 3,800 to about 4,600 kDa, from about 3,800 to about 4,500 kDa, from about 3,800 to about 4,400 kDa, from about 3,800 to about 4,300 kDa, from about 3,800 to about 4,200 kDa, from about 3,900 to about 4,700 kDa, from about 3,900 to about 4,600 kDa, from about 3,900 to about 4,500 kDa, from about 3,900 to about 4,400 kDa, from about 3,900 to about 4,300 kDa, or from about 3,900 to about 4,200 kDa.

In certain embodiments of the invention wherein the polysaccharide-protein conjugates in the multivalent immunogenic compositions are prepared in an aprotic solvent, the Mw of each of the S. pneumoniae polysaccharide protein conjugates in the composition (for a single serotype) is from about 1,000 to about 10,000 kDa, from about 1,500 to about 5,500 kDa, from about 1,500 to about 5,600 kDa, from about 1,500 to about 5,700 kDa, from about 1,500 to about 5,800 kDa, from about 1,500 to about 5,900 kDa, from about 1,500 to about 6,000 kDa, from about 1,000 to about 5,500 kDa, from about 1,000 to about 5,000 kDa, from about 1,000 to about 4,000 kDa, from about 1,000 to about 4,500 kDa, from about 1,000 to about 4,000 kDa, or from about 1,000 to about 3,500 kDa. In other embodiments, the Mw of a conjugate from a single serotype within the composition is about 1,000 kDa, about 1,100 kDa, about 1,200 kDa, about 1,300 kDa, about 1,400 kDa, about 1,500 kDa, about 1,600 kDa, about 1,700 kDa, about 1,800 kDa, about 1,900 kDa, about 2,000 kDa, about 2,100 kDa, about 2,200 kDa, about 2,300 kDa, about 2,400 kDa, about 2,500 kDa, about 2,600 kDa, about 2,700 kDa, about 2,800 kDa, about 2,900 kDa, about 3,000 kDa, about 3,100 kDa, about 3,200 kDa, about 3,300 kDa, about 3,400 kDa, about 3,500 kDa, about 3,600 kDa, about 3,700 kDa, about 3,800 kDa, about 3,900 kDa, about 4,000 kDa, about 4,100 kDa, about 4,200 kDa, about 4,300 kDa, about 4,400 kDa, about 4,500 kDa, about 4,600 kDa, about 4,700 kDa, about 4,800 kDa, about 4,900 kDa, about 5,000 kDa, about 5,100 kDa, about 5,200 kDa, about 5,300 kDa, about 5,400 kDa, or about 5,500 kDa.

In certain embodiments of the invention the polysaccharide-protein conjugates in the multivalent immunogenic compositions are prepared in an aprotic solvent. In certain embodiments, the percentage (as calculated by the number of polysaccharide serotypes prepared in an aprotic solvent divided by the total number of polysaccharide serotypes, where total number includes those prepared in an aprotic solvent or a protic solvent) of *S. pneumoniae* serotype specific conjugates prepared in an aprotic solvent may be greater than 50%, or greater than 60%, or greater than 70%, or greater than 80%, or greater than 90% or are 100%.

In certain embodiments of the invention, the serotype 3 polysaccharide-protein conjugate in the composition is prepared in an aprotic solvent and the Mw of said conjugate is from about 1,000 to about 5,000 kDa, or from about 1,000 to about 4,000 kDa, or from about 1,000 to about 3,000 kDa, or from about 1,000 to about 2,500 kDa, or from about 1,000 to about 2,000 kDa.

In certain embodiments of the invention wherein one or more, or all, of the polysaccharide-protein conjugates in the multivalent immunogenic compositions are prepared in an aprotic solvent, the number average molecular weight (Mn) of the *S. pneumoniae* polysaccharide protein conjugates in the composition (average of all conjugates in the composition) is from about 900 to about 3,000 kDa, from about 1,000 to about 3,000 kDa, from about 1,000 to about 2,500 kDa, from about 1,500 to about 2,500 kDa, from about 1,800 to about 2,500 kDa, from about 1,900 to about 2,500 kDa, or from about 2,000 to about 2,500 kDa.

In certain embodiments of the invention wherein one or more, or all, of the polysaccharide-protein conjugates in the multivalent immunogenic compositions are prepared in an aprotic solvent, the Mn of each of the *S. pneumoniae* polysaccharide protein conjugates in the composition (for a single serotype) is from about 700 to about 7,000 kDa, from about 1,000 to about 6,000 kDa, from about 1,000 to about 5,000 kDa, from about 1,000 to about 4,000 kDa, from about 1,000 to about 3,000 kDa, from about 900 to about 5,500 kDa, from about 900 to about 5,000 kDa, from about 900 to about 4,500 kDa, from about 900 to about 4,000 kDa, from about 900 to about 3,500 kDa, or from about 900 to about 3,000 kDa.

In embodiments of the invention, the Mw and/or Mn of the *S. pneumoniae* polysaccharide protein conjugates in the composition is stable for 4 weeks or more at 37° C., 4 weeks or more at 25° C., and/or 12 weeks or more at 4° C.

In embodiments of the invention, the polysaccharide concentration, Mw, and/or Mn are determined using HPSEC UV/MALS/RI.

In some embodiment of the invention, wherein one or more, or all, of the polysaccharide-protein conjugates in the multivalent immunogenic compositions are prepared in an aprotic solvent, the emission maximum of the composition measured using intrinsic protein fluorescence spectroscopy with an excitation wavelength at 280 nanometers (nm) is from about 335 nm to about 342 nm. In some embodiments, the emission maximum remains from about 335 nm to about 342 nm and the fluorescence intensity is stable for at least 1 week at 37° C. In some embodiments, the emission maximum remains from about 335 nm to about 342 nm and the fluorescence intensity is stable for 1 week at 37° C.

In some embodiments, all of the pneumococcal polysaccharide conjugates in the multivalent composition are prepared using reductive amination in DMSO. In certain sub-embodiments, the multivalent composition comprising polysaccharide conjugates which were all prepared using DMSO does not comprise an adjuvant.

Without being bound by any particular theory, one possible mechanism for the enhanced immunogenicity observed with glycoconjugates prepared in DMSO include an increased number of linkages between the carbohydrate (capsular polysaccharide) and lysine residues on the surface of the carrier protein which would result in additional attachment points between the protein and polysaccharide to impart stability and counter chemical depolymerization or breakdown of the peptide carbohydrate bond. See, e.g., Hsieh, Characterization of Saccharide-CRM197 Conjugate Vaccines in Brown F, Corbel M, Griffiths E (eds): Physico-Chemical Procedures for the Characterization of Vaccines. Dev. Biol. Basel, Karger, 2000, vol 103, pp. 93-104. An additional benefit of the increased polysaccharide-protein linkages that are created during conjugation in the DMSO solvent could be additional opportunities for successful presentation of peptide-carbohydrate to T-cells. A possible mechanism of enhanced immunogenicity observed by conjugation in the DMSO solvent could be due to the denaturation of CRM197 in organic solvent, which exposes additional lysines for polysaccharide linkages giving increased chances for glycopeptide presentation at the surface of an APC for T-cell dependent response to different peptide epitopes. See Avci et al., 2011, Nature Medicine 17: 1602-1610.

Yet another benefit of conjugation in an organic solvent generating denatured CRM197 in the conjugates could be reduced immunological interference of antibodies against native CRM197 epitopes. A further benefit of the increased polysaccharide-protein linkages that are created during conjugation in the DMSO solvent could be the formation of larger sized polysaccharide protein conjugates resulting in enhanced immunogenicity. The compositions of the invention are believed to provide significant advantages in eliciting a human response.

In certain embodiments, the conjugation reaction is performed by reductive amination wherein nickel is used for greater conjugation reaction efficiency and to aid in free cyanide removal. Transition metals are known to form stable complexes with cyanide and are known to improve reductive methylation of protein amino groups and formaldehyde with sodium cyanoborohydride (S Gidley et al., *Biochem J.* 1982, 203: 331-334; Jentoft et al. *Anal Biochem.* 1980, 106: 186-190). By complexing residual, inhibitory cyanide, the addition of nickel increases the consumption of protein during the conjugation and leads to formation of larger, potentially more immunogenic conjugates.

Differences in starting cyanide levels in sodium cyanoborohydride reagent lots also lead to inconsistent conjugation performance, resulting in variable product attributes, such as conjugate size and conjugate Ps-to-CRM197 ratio. The addition of nickel reduced conjugation inconsistency by complexing cyanide, eliminating differences in sodium cyanoborohydride lots.

Suitable alternative chemistries include the activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable conjugation techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

After conjugation of the capsular polysaccharide to the carrier protein, the polysaccharide-protein conjugates are purified (enriched with respect to the amount of polysaccharide-protein conjugate) by one or more of a variety of techniques. Examples of these techniques are well known to the skilled artisan and include concentration/diafiltration operations, ultrafiltration, precipitation/elution, column chromatography, and depth filtration. See, e.g., U.S. Pat. No. 6,146,902.

After the individual glycoconjugates are purified, they are compounded to formulate the immunogenic composition of the present invention. These pneumococcal conjugates may be prepared by separate processes and bulk formulated into a single dosage formulation.

An alternative method for characterizing the glycoconjugates of the invention is by the number of lysine residues in the carrier protein (e.g., CRM197) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the extent of conjugation, as measured by lysine consumption of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate of the invention is about 2, about 3, about 4, about 5, about 6, about 7, about 8, about 9, about 10, about 11, about 12, about 13, about 14 or about 15. In another embodiment, the degree of conjugation of the glycoconjugate of the invention is between 4 and 7. In some such embodiments, the carrier protein is CRM197.

The glycoconjugates of the compositions of the invention may also be characterized by the ratio (weight/weight) of polysaccharide to carrier protein (Ps:Pr). In some embodiments, the ratio of polysaccharide to carrier protein of the glycoconjugates (w/w) in the composition is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the polysaccharide to carrier protein ratio (w/w) is between 0.5 and 2.5, between 0.5 and 1.5, between 0.8 and 2.5, between 0.5 and 1.0, between 1.0 and 1.5, between 1.0 and 2.0, between 0.8 and 2.4, between 0.8 and 2.3, between 0.8 and 2.2, between 0.8 and 2.1, between 0.8 and 2.0, between 0.8 and 1.9, between 0.8 and 1.8, between 0.8 and 1.7, between 0.8 and 1.6, between 0.8 and 1.5, between 0.8 and 1.4, between 0.8 and 1.3, between 0.9 and 2.4, between 0.9 and 2.3, between 0.9 and 2.2, between 0.9 and 2.1, between 0.9 and 2.0, between 0.9 and 1.9, between 0.9 and 1.8, between 0.9 and 1.7, between 0.9 and 1.6, between 0.9 and 1.5, between 0.9 and 1.4, between 0.9 and 1.3, between 0.9 and 1.2, between 1.0 and 2.4, between 1.0 and 2.3, between 1.0 and 2.2, between 1.0 and 2.1, between 1.0 and 2.0, between 1.0 and 1.9, between 1.0 and 1.8, between 1.0 and 1.7, between 1.0 and 1.6, between 1.0 and 1.5, between 1.0 and 1.4, between 1.0 and 1.3 or between 1.0 and 1.2. In further embodiments, the saccharide to carrier protein ratio (w/w) is between 0.8 and 1.2. In some such embodiments, the carrier protein is CRM197. The glycoconjugates and immunogenic compositions of the invention may contain free saccharide that is not covalently conjugated to the carrier protein, but is nevertheless present in the glycoconjugate composition. The free saccharide may be non-covalently associated with (e.g., non-covalently bound to, adsorbed to, or entrapped in or with) the glycoconjugate.

In specific embodiments, the saccharide to carrier protein ratio (w/w) for the serotype 15A conjugate is from about 1.0 to about 2.0, from about 1.25 to about 1.75, or from about 1.3 to about 1.7. In other embodiments, the saccharide to carrier protein ratio (w/w) for serotype 15A is about 1.1, 1.2, 1.3, 1.4, 1.5, 1.6, 1.7, or 1.8.

In specific embodiments, the saccharide to carrier protein ratio (w/w) for the serotype 15C conjugate is from about 1.0 to about 2.0, from about 1.25 to about 1.75, or from about 1.3 to about 1.7. In other embodiments, the saccharide to carrier protein ratio (w/w) for serotype 15C is about 1.1, 1.2, 1.3, 1.4, 1.5, 1.6, 1.7, or 1.8.

In specific embodiments, the saccharide to carrier protein ratio (w/w) for the serotype 33F conjugate is from about 1.0 to about 2.0, from about 1.25 to about 1.75, or from about 1.3 to about 1.7. In other embodiments, the saccharide to carrier protein ratio (w/w) for serotype 33F is about 1.1, 1.2, 1.3, 1.4, 1.5, 1.6, 1.7, or 1.8.

In specific embodiments, the saccharide to carrier protein ratio (w/w) for the serotype 35B conjugate is from about 1.25 to about 2.25, from about 1.25 to about 2.0, or from about 1.3 to about 1.8. In other embodiments, the saccharide to carrier protein ratio (w/w) for serotype 35B is about 1.2, 1.3, 1.4, 1.5, 1.6, 1.7, 1.8, 1.9, or 2.0.

In specific embodiments, the saccharide to carrier protein ratio (w/w) for the serotype 24F conjugate is from about 0.5 to about 1.5, from about 0.75 to about 1.25, or from about 0.8 to about 1.0. In other embodiments, the saccharide to carrier protein ratio (w/w) for serotype 24F is about 0.5, 0.6, 0.7, 0.8, 0.9, or 1.0.

In a preferred embodiment, the glycoconjugate composition comprises less than about 50%, 45%, 40%, 35%, 30%, 25%, 20% or 15% of free polysaccharide compared to the total amount of polysaccharide. In a preferred embodiment the glycoconjugate composition comprises less than about 25% of free polysaccharide compared to the total amount of polysaccharide. In a preferred embodiment the glycoconjugate composition comprises less than about 20% of free polysaccharide compared to the total amount of polysaccharide. In a preferred embodiment the glycoconjugate composition comprises less than about 15% of free polysaccharide compared to the total amount of polysaccharide.

IV. Methods of Use

Embodiments of the invention also include one or more of the multivalent immunogenic compositions described herein (i) for use in, (ii) for use as a medicament or composition for, or (iii) for use in the preparation of a medicament for: (a) therapy (e.g., of the human body); (b) medicine; (c) inhibition of infection with *Streptococcus pneumoniae*; (d) induction of an immune response or a protective immune response against *S. pneumoniae*; (e) prophylaxis of infection by *S. pneumoniae*; (f) prevention of recurrence of *S. pneumoniae* infection; (g) reduction of the progression, onset or severity of pathological symptoms associated with *S. pneumoniae* infection including the prevention of associated complications such as brain damage, hearing loss, and seizures, (h) reduction of the likelihood of a *S. pneumoniae* infection or, (i) treatment, prophylaxis of, or delay in the onset, severity, or progression of pneumococcal disease(s), including, but not limited to: pneumococcal pneumonia, pneumococcal bacteremia, pneumococcal meningitis, otits media and sinusitis. In these uses, the multivalent pneumococcal polysaccharide-conjugate compositions of the invention can optionally be employed in combination with one or more adjuvants, or without an adjuvant.

Accordingly, the invention provides methods for the prophylactic treatment of (i.e. protection against) *S. pneumoniae* infection or pneumococcal disease comprising administering one or more of the multivalent immunogenic pneumococcal polysaccharide-protein conjugate compositions of the invention to a patient in need of treatment.

The compositions and formulations of the present invention can be used to protect or treat a human susceptible to infection, e.g., a pneumococcal infection, by means of administering such composition or formulation via a systemic or mucosal route.

In one embodiment, the invention provides a method of inducing an immune response to *S. pneumoniae*, comprising administering to a patient an immunologically effective amount of a multivalent immunogenic composition of the invention. In another embodiment, the invention provides a method of vaccinating a human against a pneumococcal infection, comprising the step of administering to the human an immunogically effective amount of a multivalent immunogenic composition of the invention.

Thus, in one aspect, the invention provides a method for (1) inducing an immune response in a human patient, (2) inducing a protective immune response in a human patient, (3) vaccinating a human patient against an infection with *S. pneumoniae*, or (4) reducing the likelihood of a *S. pneumoniae* infection in a human patient, the method comprising administering a multivalent immunogenic composition of the invention to the patient (i.e. any multivalent immunogenic composition described herein, such as the multivalent immunogenic compositions described in Section II, entitled "Multivalent Immunogenic Compositions," supra).

In one embodiment, the invention provides a method for the prevention of pneumococcal pneumonia and/or invasive pneumococcal disease in an infant (less than 1 year of age), toddler (approximately 12 to 24 months), or young child (approximately 2 to 5 years).

In another embodiment, the invention provides a method for the prevention of pneumococcal pneumonia and/or invasive pneumococcal disease in a 6 week through 17 year old patient.

In another embodiment, the invention provides a method for the prevention of pneumococcal pneumonia and/or invasive pneumococcal disease in a 6 month through 17 year old patient.

In another embodiment, the invention provides a method for the prevention of pneumococcal pneumonia and/or invasive pneumococcal disease in adults 18 years of age and older.

In another embodiment, the invention provides a method for the prevention of pneumococcal pneumonia and/or invasive pneumococcal disease in adults 50 years of age and older.

In another embodiment, the invention provides a method for the prevention of pneumococcal pneumonia and/or invasive pneumococcal disease in adults 65 years of age and older.

In another embodiment, the invention provides a method for the prevention of pneumococcal pneumonia and/or invasive pneumococcal disease caused by one or more of the following *Streptococcus pneumoniae* strains: 1, 3, 4, 5, 6A, 6B, 6C, 7F, 8, 9V, 10A, 11A, 12F, 14, 15A, 15B, 15C, 18C, 19A, 19F, 22F, 23B, 23F, 24F, 33F and 35B.

In one embodiment of the methods above, the composition comprises multiple *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise serotypes: 1, 3, 4, 5, 6A, 6B, 6C, 7F, 8, 9V, 10A, 12F, 14, 15A, 15B, 15C, 18C, 19A, 19F, 22F, 23B, 23F, 24F, 33F and 35B or serotypes: 1, 3, 4, 5, 6A, 6B, 6C, 7F, 8, 9V, 10A, 11A, 12F, 14, 15A, 15B, 15C, 18C, 19A, 19F, 22F, 23B, 23F, 24F, 33F and 35B. In another embodiment of the methods above, the composition comprises multiple *S. pneumoniae* polysaccharide protein conjugates wherein each of the conjugates comprises a polysaccharide from an S. pneumoniae serotype conjugated to a carrier protein, wherein the serotypes of S. pneumoniae consist of serotypes: 1, 3, 4, 5, 6A, 6B, 6C, 7F, 8, 9V, 10A, 12F, 14, 15A, 15B, 15C, 18C, 19A, 19F, 22F, 23B, 23F, 24F, 33F and 35B or serotypes: 1, 3, 4, 5, 6A, 6B, 6C, 7F, 8, 9V, 10A, 11A, 12F, 14, 15A, 15B, 15C, 18C, 19A, 19F, 22F, 23B, 23F, 24F, 33F and 35B. In one embodiment of the methods above, the composition comprises multiple S. pneumoniae polysaccharide protein conjugates wherein each of the conjugates comprises a polysaccharide from an S. pneumoniae serotype conjugated to a carrier protein, wherein the serotypes of S. pneumoniae comprise serotypes: 1, 3, 4, 5, 6A, 6B, 7F, 8, 9V, 10A, 12F, 14, 15A, 15C, 18C, 19A, 19F, 22F, 23B, 23F, 24F, 33F and 35B or serotypes: 1, 3, 4, 5, 6A, 6B, 7F, 8, 9V, 10A, 11A, 12F, 14, 15A, 15C, 18C, 19A, 19F, 22F, 23B, 23F, 24F, 33F and 35B. In another embodiment of the methods above, the composition comprises multiple S. pneumoniae polysaccharide protein conjugates wherein each of the conjugates comprises a polysaccharide from an S. pneumoniae serotype conjugated to a carrier protein, wherein the serotypes of S. pneumoniae consist of serotypes: 1, 3, 4, 5, 6A, 6B, 7F, 8, 9V, 10A, 12F, 14, 15A, 15C, 18C, 19A, 19F, 22F, 23B, 23F, 24F, 33F and 35B or serotypes: 1, 3, 4, 5, 6A, 6B, 7F, 8, 9V, 10A, 11A, 12F, 14, 15A, 15C, 18C, 19A, 19F, 22F, 23B, 23F, 24F, 33F and 35B. In one embodiment of the methods above, the composition comprises multiple S. pneumoniae polysaccharide protein conjugates wherein each of the conjugates comprises a polysaccharide from an S. pneumoniae serotype conjugated to a carrier protein, wherein the serotypes of S. pneumoniae comprise serotypes: 1, 3, 4, 5, 6A, 6B, 7F, 9V, 10A, 12F, 14, 15A, 15C, 18C, 19A, 19F, 22F, 23B, 23F, 24F, 33F and 35B. In another embodiment of the methods above, the composition comprises multiple S. pneumoniae polysaccharide protein conjugates wherein each of the conjugates comprises a polysaccharide from an S. pneumoniae serotype conjugated to a carrier protein, wherein the serotypes of S. pneumoniae consist of serotypes: 1, 3, 4, 5, 6A, 6B, 7F, 9V, 10A, 12F, 14, 15A, 15C, 18C, 19A, 19F, 22F, 23B, 23F, 24F, 33F and 35B or serotypes.

It has been shown that a pneumococcal conjugate vaccine comprising serotype 6A polysaccharide may provide some cross-protection against serotype 6C (Cooper et al., *Vaccine* 29 (2011) 7207-7211). Therefore, in some embodiments of the methods above, the invention also provides use of multivalent immunogenic compositions that do not comprise serotype 6C polysaccharide conjugate, but instead comprise serotype 6A polysaccharide conjugate or serotypes 6A and 6B polysaccharide conjugates. In other embodiments, the immunogenic composition comprises pneumococcal polysaccharide conjugates of serotypes 6A, 6B, and 6C.

In particular embodiments of the methods above, the multivalent immunogenic compositions comprise pneumococcal conjugates that include polysaccharides of a group of S. pneumoniae serotypes selected from the group consisting of:

a) 1, 3, 4, 5, 6A, 6B, 7F, 9V, 10A, 12F, 14, 15A, DeOAc15B, 18C, 19A, 19F, 22F, 23B, 23F, 24F, 33F and 35B;
b) 1, 3, 4, 5, 6A, 6B, 7F, 9V, 10A, 12F, 14, 15A, 15C, 18C, 19A, 19F, 22F, 23B, 23F, 24F, 33F and 35B;
c) 1, 3, 4, 5, 6A, 6B, 7F, 8, 9V, 10A, 12F, 14, 15A, DeOAc15B, 18C, 19A, 19F, 22F, 23B, 23F, 24F, 33F and 35B;
d) 1, 3, 4, 5, 6A, 6B, 7F, 8, 9V, 10A, 12F, 14, 15A, 15C, 18C, 19A, 19F, 22F, 23B, 23F, 24F, 33F and 35B;
e) 1, 3, 4, 5, 6A, 6B, 7F, 8, 9V, 10A, 12F, 14, 15B, 18C, 19A, 19F, 22F, 23B, 23F, 24F, 33F and 35B;
f) 1, 3, 4, 5, 6A, 6B, 7F, 8, 9V, 10A, 11A, 12F, 14, 15A, DeOAc15B, 18C, 19A, 19F, 22F, 23B, 23F, 24F, 33F and 35B;
g) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B;
h) 1, 3, 4, 5, 6A, 6B, 7F, 8, 9V, 10A, 11A, 12F, 14, 15A, 15B, 18C, 19A, 19F, 22F, 23B, 23F, 24F, 33F and 35B;
i) 1, 3, 4, 5, 6A, 6B, 7F, 8, 9V, 10A, 11A, 12F, 14, 15B, 18C, 19A, 19F, 22F, 23B, 23F, 24F, 33F and 35B;
j) 1, 3, 4, 5, 6A, 7F, 9V, 10A, 12F, 14, 15A, 15C, 18C, 19A, 19F, 22F, 23B, 23F, 24F, 33F and 35B;
k) 1, 3, 4, 5, 6B, 7F, 9V, 10A, 12F, 14, 15A, 15C, 18C, 19A, 19F, 22F, 23B, 23F, 24F, 33F and 35B;
l) 1, 3, 4, 5, 6C, 7F, 9V, 10A, 12F, 14, 15A, 15C, 18C, 19A, 19F, 22F, 23B, 23F, 24F, 33F and 35B;
m) 1, 3, 4, 5, 6A, 7F, 8, 9V, 10A, 12F, 14, 15A, 15C, 18C, 19A, 19F, 22F, 23B, 23F, 24F, 33F and 35B;
n) 1, 3, 4, 5, 6B, 7F, 8, 9V, 10A, 12F, 14, 15A, 15C, 18C, 19A, 19F, 22F, 23B, 23F, 24F, 33F and 35B;
o) 1, 3, 4, 5, 6C, 7F, 8, 9V, 10A, 12F, 14, 15A, 15C, 18C, 19A, 19F, 22F, 23B, 23F, 24F, 33F and 35B;
p) 1, 3, 4, 5, 6A, 7F, 8, 9V, 10A, 11A, 12F, 14, 15A, 15C, 18C, 19A, 19F, 22F, 23B, 23F, 24F, 33F and 35B;
q) 1, 3, 4, 5, 6B, 7F, 8, 9V, 10A, 11A, 12F, 14, 15A, 15C, 18C, 19A, 19F, 22F, 23B, 23F, 24F, 33F and 35B;
r) 1, 3, 4, 5, 6C, 7F, 8, 9V, 10A, 11A, 12F, 14, 15A, 15C, 18C, 19A, 19F, 22F, 23B, 23F, 24F, 33F and 35B;
s) 1, 3, 4, 5, 6A, 7F, 9V, 10A, 12F, 14, 15A, 15B, 18C, 19A, 19F, 22F, 23B, 23F, 24F, 33F and 35B;
t) 1, 3, 4, 5, 6B, 7F, 9V, 10A, 12F, 14, 15A, 15B, 18C, 19A, 19F, 22F, 23B, 23F, 24F, 33F and 35B;
u) 1, 3, 4, 5, 6C, 7F, 9V, 10A, 12F, 14, 15A, 15B, 18C, 19A, 19F, 22F, 23B, 23F, 24F, 33F and 35B;
v) 1, 3, 4, 5, 6A, 7F, 8, 9V, 10A, 12F, 14, 15A, 15B, 18C, 19A, 19F, 22F, 23B, 23F, 24F, 33F and 35B;
w) 1, 3, 4, 5, 6B, 7F, 8, 9V, 10A, 12F, 14, 15A, 15B, 18C, 19A, 19F, 22F, 23B, 23F, 24F, 33F and 35B;
x) 1, 3, 4, 5, 6C, 7F, 8, 9V, 10A, 12F, 14, 15A, 15B, 18C, 19A, 19F, 22F, 23B, 23F, 24F, 33F and 35B;
y) 1, 3, 4, 5, 6A, 7F, 8, 9V, 10A, 11A, 12F, 14, 15A, 15B, 18C, 19A, 19F, 22F, 23B, 23F, 24F, 33F and 35B;
z) 1, 3, 4, 5, 6B, 7F, 8, 9V, 10A, 11A, 12F, 14, 15A, 15B, 18C, 19A, 19F, 22F, 23B, 23F, 24F, 33F and 35B; and
aa) 1, 3, 4, 5, 6C, 7F, 8, 9V, 10A, 11A, 12F, 14, 15A, 15B, 18C, 19A, 19F, 22F, 23B, 23F, 24F, 33F and 35B.

In further embodiments of the methods above, the composition comprises multiple S. pneumoniae polysaccharide protein conjugates wherein each of the conjugates comprises a polysaccharide from an S. pneumoniae serotype conjugated to a carrier protein, wherein the serotypes of S. pneumoniae comprise serotypes: i) 1, 3, 4, 5, 6A, 6B, 7F, 9V, 10A, 12F, 14, 15A, 15C, 18C, 19A, 19F, 22F, 23B, 23F, 24F, 33F and 35B; or ii) 1, 3, 4, 5, 6A, 6B, 7F, 8, 9V, 10A, 12F, 14, 15A, 15C, 18C, 19A, 19F, 22F, 23B, 23F, 24F, 33F and 35B; or iii) 1, 3, 4, 5, 6A, 6B, 7F, 8, 9V, 10A, 11A, 12F, 14, 15A, 15C, 18C, 19A, 19F, 22F, 23B, 23F, 24F, 33F and 35B; or iv) 1, 3, 4, 5, 6A, 6B, 7F, 8, 9V, 10A, 11A, 12F, 14, 15A, 15B, 18C, 19A, 19F, 22F, 23B, 23F, 24F, 33F and 35B.

It has also been shown that a pneumococcal conjugate vaccine comprising serotype 10A polysaccharide may provide some cross-protection against serotype 39 (see WO 2017/085586). Therefore, in some embodiments of the methods above, the invention also provides use of multivalent immunogenic compositions that do not comprise serotype 10A polysaccharide conjugate, but instead comprise serotype 39 polysaccharide conjugate. In other embodiments, the immunogenic composition comprises pneumococcal polysaccharide conjugates of serotypes 10A and 39. In particular embodiments of the methods above, the serotypes of S. pneumoniae comprise a group of serotypes selected from the group consisting of:

bb) 1, 3, 4, 5, 6A, 6B, 7F, 9V, 12F, 14, 15A, DeOAc15B, 18C, 19A, 19F, 22F, 23B, 23F, 24F, 33F, 35B and 39;
cc) 1, 3, 4, 5, 6A, 6B, 7F, 9V, 12F, 14, 15A, 15C, 18C, 19A, 19F, 22F, 23B, 23F, 24F, 33F, 35B and 39;
dd) 1, 3, 4, 5, 6A, 6B, 7F, 8, 9V, 12F, 14, 15A, DeOAc15B, 18C, 19A, 19F, 22F, 23B, 23F, 24F, 33F, 35B and 39;
ee) 1, 3, 4, 5, 6A, 6B, 7F, 8, 9V, 12F, 14, 15A, 15C, 18C, 19A, 19F, 22F, 23B, 23F, 24F, 33F, 35B and 39;
ff) 1, 3, 4, 5, 6A, 6B, 7F, 8, 9V, 12F, 14, 15B, 18C, 19A, 19F, 22F, 23B, 23F, 24F, 33F, 35B and 39;
gg) 1, 3, 4, 5, 6A, 6B, 7F, 8, 9V, 11A, 12F, 14, 15A, DeOAc15B, 18C, 19A, 19F, 22F, 23B, 23F, 24F, 33F, 35B and 39;
hh) 1, 3, 4, 5, 6A, 6B, 7F, 8, 9V, 11A, 12F, 14, 15A, 15C, 18C, 19A, 19F, 22F, 23B, 23F, 24F, 33F, 35B and 39;
ii) 1, 3, 4, 5, 6A, 6B, 7F, 8, 9V, 11A, 12F, 14, 15A, 15B, 18C, 19A, 19F, 22F, 23B, 23F, 24F, 33F, 35B and 39;
jj) 1, 3, 4, 5, 6A, 6B, 7F, 8, 9V, 11A, 12F, 14, 15B, 18C, 19A, 19F, 22F, 23B, 23F, 24F, 33F, 35B and 39;
kk) 1, 3, 4, 5, 6A, 7F, 9V, 12F, 14, 15A, 15C, 18C, 19A, 19F, 22F, 23B, 23F, 24F, 33F, 35B and 39;
ll) 1, 3, 4, 5, 6B, 7F, 9V, 12F, 14, 15A, 15C, 18C, 19A, 19F, 22F, 23B, 23F, 24F, 33F, 35B and 39;
mm) 1, 3, 4, 5, 6C, 7F, 9V, 12F, 14, 15A, 15C, 18C, 19A, 19F, 22F, 23B, 23F, 24F, 33F, 35B and 39;
nn) 1, 3, 4, 5, 6A, 7F, 8, 9V, 12F, 14, 15A, 15C, 18C, 19A, 19F, 22F, 23B, 23F, 24F, 33F, 35B and 39;
oo) 1, 3, 4, 5, 6B, 7F, 8, 9V, 12F, 14, 15A, 15C, 18C, 19A, 19F, 22F, 23B, 23F, 24F, 33F, 35B and 39;
pp) 1, 3, 4, 5, 6C, 7F, 8, 9V, 12F, 14, 15A, 15C, 18C, 19A, 19F, 22F, 23B, 23F, 24F, 33F, 35B and 39;
qq) 1, 3, 4, 5, 6A, 7F, 8, 9V, 11A, 12F, 14, 15A, 15C, 18C, 19A, 19F, 22F, 23B, 23F, 24F, 33F, 35B and 39;
rr) 1, 3, 4, 5, 6B, 7F, 8, 9V, 11A, 12F, 14, 15A, 15C, 18C, 19A, 19F, 22F, 23B, 23F, 24F, 33F, 35B and 39;
ss) 1, 3, 4, 5, 6C, 7F, 8, 9V, 11A, 12F, 14, 15A, 15C, 18C, 19A, 19F, 22F, 23B, 23F, 24F, 33F, 35B and 39;
tt) 1, 3, 4, 5, 6A, 7F, 9V, 12F, 14, 15A, 15B, 18C, 19A, 19F, 22F, 23B, 23F, 24F, 33F, 35B and 39;
uu) 1, 3, 4, 5, 6B, 7F, 9V, 12F, 14, 15A, 15B, 18C, 19A, 19F, 22F, 23B, 23F, 24F, 33F, 35B and 39;
vv) 1, 3, 4, 5, 6C, 7F, 9V, 12F, 14, 15A, 15B, 18C, 19A, 19F, 22F, 23B, 23F, 24F, 33F, 35B and 39;
ww) 1, 3, 4, 5, 6A, 7F, 8, 9V, 12F, 14, 15A, 15B, 18C, 19A, 19F, 22F, 23B, 23F, 24F, 33F, 35B and 39;
xx) 1, 3, 4, 5, 6B, 7F, 8, 9V, 12F, 14, 15A, 15B, 18C, 19A, 19F, 22F, 23B, 23F, 24F, 33F, 35B and 39;
yy) 1, 3, 4, 5, 6C, 7F, 8, 9V, 12F, 14, 15A, 15B, 18C, 19A, 19F, 22F, 23B, 23F, 24F, 33F, 35B and 39;
zz) 1, 3, 4, 5, 6A, 7F, 8, 9V, 11A, 12F, 14, 15A, 15B, 18C, 19A, 19F, 22F, 23B, 23F, 24F, 33F, 35B and 39;
aaa) 1, 3, 4, 5, 6B, 7F, 8, 9V, 11A, 12F, 14, 15A, 15B, 18C, 19A, 19F, 22F, 23B, 23F, 24F, 33F, 35B and 39; and
bbb) 1, 3, 4, 5, 6C, 7F, 8, 9V, 11A, 12F, 14, 15A, 15B, 18C, 19A, 19F, 22F, 23B, 23F, 24F, 33F, 35B and 39.

It has also been shown that immunogenic conjugates comprising S. pneumoniae serotype 15B capsular polysaccharide covalently linked to a carrier protein may provide some cross-protection against serotype 15C and/or serotype 15A (see WO 2015/110942). Therefore, in some embodiments of the methods above, the invention also provides use of multivalent immunogenic compositions that do not comprise serotype 15C (or de-O-acetylated 15B) polysaccharide conjugate, but instead comprise serotype 15B polysaccharide conjugate (i.e. the serotype 15B polysaccharide is not substantially de-O-acetylated). In other embodiments, the immunogenic composition comprises pneumococcal polysaccharide conjugates of serotypes 15B and 15C (or de-O-acetylated 15B).

The compositions of the invention are useful in methods for providing complementary protection against S. pneumoniae in patients who had previously received a multivalent pneumococcal vaccine. In this use, the compositions of the invention can provide protection against particular S. pneumoniae serotypes that a patient had not been previously vaccinated against, can provide additional protection against S. pneumoniae serotypes that a patient had been previously vaccinated against, or can provide protection against both S. pneumoniae serotypes that a patient had not been previously vaccinated against and S. pneumoniae serotypes that a patient had been previously vaccinated against.

Thus, the invention provides a method of inducing an immune response, vaccinating, or inducing a protective immune response against S. pneumoniae in a patient, comprising administering a multivalent immunogenic composition to the patient, the composition comprising multiple S. pneumoniae polysaccharide protein conjugates, wherein the polysaccharide protein conjugates comprise capsular polysaccharide from a S. pneumoniae serotype conjugated to a carrier protein, wherein the patient had previously been vaccinated against S. pneumoniae. In embodiments of this aspect of the invention, the multivalent immunogenic composition can be any multivalent immunogenic composition described herein. In particular embodiments of the methods of the invention, the multivalent immunogenic composition is administered to a patient who was previously treated with a multivalent pneumococcal vaccine. The multivalent immunogenic vaccine may be any vaccine that is indicated for the prevention of pneumococcal disease caused by more than one serotype of S. pneumoniae.

In specific embodiments of the method above, the patient was previously treated with a multivalent pneumococcal vaccine that is indicated for the prevention of pneumococcal disease caused by one or more S. pneumoniae serotypes within a group of serotypes selected from the group consisting of:

i. 4, 6B, 9V, 14, 18C, 19F and 23F;
ii. 4, 6B, 9V, 14, 18C, 19F, 23F, 1, 3, 5, 6A, 7F, and 19A;
iii. 1, 4, 5, 6B, 7F, 9V, 14, 18C, 19F and 23F;
iv. 4, 6B, 9V, 14, 18C, 19F, 23F, 1, 3, 5, 6A, 7F, 19A, 22F, and 33F;
v. 4, 6B, 9V, 14, 18C, 19F, 23F, 1, 3, 5, 7F, 19A, 22F, 33F, 2, 8, 9N, 10A, 11A, 12F, 15B, 17F, and 20; and
vi. 4, 6B, 9V, 14, 18C, 19F, 23F, 1, 3, 5, 6A, 7F, 19A, 22F, 33F, 8, 10A, 11A, 12F and 15B.

In specific embodiments of the method above, the multivalent pneumococcal vaccine comprises multiple polysaccharide protein conjugates, wherein the polysaccharide protein conjugates comprise polysaccharide from a S. pneumoniae serotype conjugated to a carrier protein. In other embodiments, the multivalent pneumococcal vaccine comprises multiple S. pneumoniae capsular polysaccharides that are not conjugated to a carrier protein.

In additional embodiments of the method above, the patient was previously treated with PREVNAR® 13 (Pneumococcal 13-valent Conjugate Vaccine [Diphtheria CRM197 Protein], Pfizer, Inc., Philadelphia, PA, USA).

In further embodiments of the method above, the patient was previously treated with PNEUMOVAX® 23 (Pneumococcol Vaccine Polyvalent, Merck & Co., Inc., Kenilworth, NJ, USA).

In still further embodiments of the method above, the patient was previously treated with SYNFLORIX™ (Pneumococcal polysaccharide conjugate vaccine (adsorbed), GlaxoSmithKline Biologicals s.a., Rixensart, Belgium).

In embodiments of the method above, the multivalent immunogenic composition of the invention is administered to a patient at any time after the patient has received a multivalent pneumococcal vaccine, according to the treatment regimen provided by the medical professional, e.g. a physician. In particular embodiments, the multivalent immunogenic composition of the invention is administered to a patient from about 1 month to about 5 years after the patient has received the multivalent pneumococcal vaccine, alternatively, from 1 month to 1 year, from 1 month to 2 years, from 1 month to 3 years, from 1 month to 4 years, from 1 month to 6 months, from 2 months to 6 months, from 2 months to 1 year, from 1 year to 5 years, from 6 months to 5 years, from 6 months to 4 years, from 6 months to 3 years, from 6 months to 2 years, from 6 months to 1 year, from 1 year to 4 years, from 1 year to 3 years, or from 1 year to 2 years, after the patient has received the multivalent pneumococcal vaccine. In further embodiments, the multivalent immunogenic composition is administered to the patient about 1 month, about 2 months, about 3 months, about 4 months, about 5 months, about 6 months, about 7 months, about 8 months, about 9 months, about 10 months, about 11 months, about 1 year, about 1.25 years, about 1.5 years, about 1.75 years, about 2 years, about 2.25 years, about 2.5 years, about 2.75 years, about 3 years, about 3.25 years, about 3.5 years, about 3.75 years, about 4 years, about 4.25 years, about 4.5 years, about 4.75 years, or about 5 years after the patient has received the multivalent pneumococcal vaccine.

In further embodiments, the invention provides a method for (1) inducing an immune response in a human patient, (2) inducing a protective immune response in a human patient, (3) vaccinating a human patient against an infection with *S. pneumoniae*, or (4) reducing the likelihood of a *S. pneumoniae* infection in a human patient, the method comprising administering a multivalent immunogenic composition of the invention and administering a multivalent pneumococcal vaccine to the patient, in any order. For example, the patient is administered a multivalent pneumococcal vaccine first, and the patient is administered a multivalent immunogenic composition of the invention second. Alternatively, the patient is administered a multivalent immunogenic composition of the invention first and is administered a multivalent pneumococcal vaccine second. The multivalent pneumococcal vaccine may be any vaccine indicated for the prevention of pneumococcal disease caused by more than one serotype of *S. pneumoniae*.

In specific embodiments of the method above, the patient is treated with a multivalent immunogenic composition of the invention and a multivalent pneumococcal vaccine that is indicated for the prevention of pneumococcal disease caused by one or more *S. pneumoniae* serotypes of a group of serotypes selected from the group consisting of:
 i. 4, 6B, 9V, 14, 18C, 19F and 23F;
 ii. 4, 6B, 9V, 14, 18C, 19F, 23F, 1, 3, 5, 6A, 7F, and 19A;
 iii. 1, 4, 5, 6B, 7F, 9V, 14, 18C, 19F and 23F;
 iv. 4, 6B, 9V, 14, 18C, 19F, 23F, 1, 3, 5, 6A, 7F, 19A, 22F, and 33F;
 v. 4, 6B, 9V, 14, 18C, 19F, 23F, 1, 3, 5, 7F, 19A, 22F, 33F, 2, 8, 9N, 10A, 11A, 12F, 15B, 17F, and 20; and
 vi. 4, 6B, 9V, 14, 18C, 19F, 23F, 1, 3, 5, 6A, 7F, 19A, 22F, 33F, 8, 10A, 11A, 12F and 15B.

In specific embodiments of the method above, the multivalent pneumococcal vaccine comprises capsular polysaccharides of *S. pneumoniae* serotypes 4, 6B, 9V, 14, 18C, 19F, 23F, 1, 3, 5, 7F, 19A, 22F, 33F, 2, 8, 9N, 10A, 11A, 12F, 15B, 17F, and 20A.

In specific embodiments of the method above, the multivalent pneumococcal vaccine comprises multiple polysaccharide protein conjugates, wherein the polysaccharide protein conjugates comprise polysaccharide from a *S. pneumoniae* serotype conjugated to a carrier protein. In other embodiments, the multivalent pneumococcal vaccine comprises multiple *S. pneumoniae* capsular polysaccharides that are not conjugated to a carrier protein.

In additional embodiments of the method above, the patient is treated with a multivalent immunogenic composition of the invention and is treated with PREVNAR® 13 (Pneumococcal 13-valent Conjugate Vaccine [Diphtheria CRM197 Protein], Pfizer, Inc., Philadelphia, PA, USA), in any order. In one embodiment, the patient is administered PREVNAR® 13 first, and the patient is administered a multivalent immunogenic composition of the invention second. In alternative embodiments, the patient is administered a multivalent immunogenic composition of the invention first and is administered PREVNAR® 13 second.

In further embodiments of the method above, the patient is treated with a multivalent immunogenic composition of the invention and is treated with PNEUMOVAX® 23 (pneumococcal vaccine polyvalent, Merck & Co., Inc., Kenilworth, NJ, USA), in any order. In one embodiment, the patient is administered PNEUMOVAX® 23 first, and the patient is administered a multivalent immunogenic composition of the invention second. In alternative embodiments, the patient is administered a multivalent immunogenic composition of the invention first and is administered PNEUMOVAX® 23 second.

In still further embodiments of the method above, the patient is treated with a multivalent immunogenic composition of the invention and is treated with SYNFLORIX™ (Pneumococcal polysaccharide conjugate vaccine (adsorbed), GlaxoSmithKline Biologicals s.a., Rixensart, Belgium), in any order. In one embodiment, the patient is administered SYNFLORIX™ first, and the patient is administered a multivalent immunogenic composition of the invention second. In an alternative embodiment, the patient is administered a multivalent immunogenic composition of the invention first and is administered SYNFLORIX™ second.

In some embodiments of the method above, the multivalent immunogenic composition and the multivalent pneumococcal vaccine are administered concurrently. As used herein, "concurrent administration" is not limited to dosing of two compositions at the same time, but includes administration one right after the other in any order. In some embodiments, the multivalent immunogenic composition and the multivalent pneumococcal vaccine are administered via intramuscular or subcutaneous administration into separate anatomical sites, e.g. two different arms.

In some embodiments of the method above, the amount of time between administration of the multivalent immunogenic composition of the invention and the multivalent pneumococcal vaccine is from about 4 weeks to about 1 year. In alternative embodiments, the amount of time is from about 1 month to about 5 years.

In one embodiment, the patient is administered the multivalent pneumococcal vaccine first and the multivalent immunogenic composition of the invention second. In alternative embodiments, the patient is administered a multivalent immunogenic composition of the invention first and is administered the multivalent pneumococcal vaccine second.

Also provided is a method of inducing an immune response, vaccinating or inducing a protective immune response against *S. pneumoniae* in a patient, comprising:

(1) administering a multivalent immunogenic composition of the invention to the patient,
(2) waiting for a pre-determined amount of time to pass, and
(3) administering a multivalent pneumococcal vaccine to the patient.

In this method, the multivalent immunogenic composition can comprise any combination of *S. pneumoniae* polysaccharide protein conjugates set forth herein and the multivalent pneumococcal vaccine can be any vaccine indicated for the prevention of disease caused by more than one serotype of *S. pneumoniae*.

Also provided by the invention is a method of inducing an immune response, vaccinating or inducing a protective immune response against *S. pneumoniae* in a patient, comprising:

(1) administering a multivalent pneumococcal vaccine to the patient,
(2) waiting for a pre-determined amount of time to pass, and
(3) administering a multivalent immunogenic composition of the invention to the patient.

In this method, the multivalent immunogenic composition can comprise any combination of *S. pneumoniae* polysaccharide protein conjugates set forth herein and the multivalent pneumococcal vaccine can be any vaccine indicated for the prevention of disease caused by more than one serotype of *S. pneumoniae*.

In some embodiments of the methods above, the multivalent pneumococcal vaccine comprises multiple *S. pneumoniae* polysaccharide protein conjugates, wherein the polysaccharide protein conjugates comprise capsular polysaccharide from a *S. pneumoniae* serotype conjugated to a carrier protein. In alternative embodiments, the multivalent pneumococcal vaccine comprises *S. pneumoniae* capsular polysaccharides that are not conjugated to a carrier protein.

In any embodiments of the methods of the invention (i.e. any of the methods described herein), the method may further comprise administering one or more additional doses of a multivalent immunogenic composition of the invention to the patient. In such methods, the patient may have already received a multivalent pneumococcal vaccine prior to receiving a first dose of a multivalent immunogenic composition of the invention, supra, or may not have been vaccinated against *S. pneumoniae* prior to receiving a multivalent immunogenic composition of the invention. Thus, in one embodiment, a patient who had received a multivalent pneumococcal vaccine indicated for the prevention of pneumococcal disease caused by *S. pneumoniae* is administered two or more doses of a multivalent immunogenic composition of the invention. In alternative embodiments, a patient who had not been previously treated with any vaccine indicated for the prevention of pneumococcal disease, is administered two or more doses of a multivalent immunogenic composition of the invention.

In embodiments of the method above, the two or more doses are of the same multivalent immunogenic composition of the invention. In alternative embodiments, the two or more doses are of different multivalent immunogenic compositions of the invention.

In specific embodiments of any of these methods, the patient is administered two, three, or four doses of a multivalent immunogenic composition of the invention. In particular embodiments, the patient is immunocompromised (e.g., on an immunosuppressive regimen following a stem cell transplant).

In some embodiments, the amount of time between administration of each dose of multivalent immunogenic composition of the invention is from about 4 weeks to about 1 year. In alternative embodiment, the amount of time between administration of each dose of multivalent immunogenic composition of the invention is from about 1 month to about 5 years.

In embodiments of any of the methods of the invention, the patient to be treated with the composition(s) of the invention is a human. In certain embodiments, the human patient is an infant (approximately 6 weeks to 12 months). In certain embodiments, the human patient is a toddler (approximately 12 to 24 months), or young child (approximately 2 to 5 years). The compositions of this invention are also suitable for use with older children, adolescents and adults (e.g., aged 18 to 45 years, aged 18 to 50 years, aged 18 to 55 years, aged 18 to 60 years or 18 to 65 years). In other embodiments of any of the methods of the invention, the patient is from about 2 to about 18 years of age. In further embodiments of any of the methods of the invention, the patient is 18 years of age or older.

In further embodiments of the methods of the invention, the patient is an infant and the infant is administered 1, 2, or 3 doses of a multivalent immunogenic composition of the instant invention. The amount of time between administration of each dose can vary, but an example of a dosing schedule includes administration of a dose at 2 months of age, then another administration of a dose at 4 months of age, and finally a final administration of a dose at 6 months of age. Another example of an administration schedule in infants is administration of a dose at 2 months of age and then another administration of a dose at 3 months of age. Another example of an administration schedule in infants is administration of a dose at 2 months of age and then another administration of a dose at 3 months of age, and finally a final administration of a dose at 6 months of age. In further embodiments, an infant patient can receive an additional "booster" dose of a multivalent immunogenic composition of the instant invention when the infant becomes a toddler. For example, an infant is dosed at 2 months of age, then another administration of a dose at 4 months of age, and finally a final administration of a dose at 6 months of age, then, when the infant reaches the age of a toddler, an additional "booster" dose of a multivalent immunogenic composition of the instant invention is administered between 11 to 15 months of age.

In an embodiment, an infant is administered 2 doses of a multivalent immunogenic composition of the instant invention.

In an embodiment, an infant is administered 3 doses of a multivalent immunogenic composition of the instant invention.

In an embodiment, a patient is administered 3 doses of a multivalent immunogenic composition of the instant invention, wherein the first and second doses are administered between 2 and 10 months of age and the third dose is administered between 11 to 15 months of age.

In an embodiment, a patient is administered 4 doses of a multivalent immunogenic composition of the instant invention, wherein the first dose is administered at 2 months of age, the second dose is administered at 4 months of age, the third dose is administered at 6 months of age and the fourth dose is administered between 11 to 15 months of age.

In further embodiments of the methods of the invention, the human patient is elderly. In some embodiments of any of the methods of the invention, the patient is 50 years of age or older. In some embodiments of any of the methods of the invention, the patient is 55 years of age or older. In some embodiments of any of the methods of the invention, the patient is 60 years of age or older. In still further embodiments of any of the methods of the invention, the patient is 65 years of age or older. In additional embodiments of any of the methods of the invention, the patient is 70 years of age or older.

In some embodiments of any of the methods of the invention, the patient to be treated with an immunogenic composition of the invention is immunocompromised.

In some embodiments of any of the methods of the invention, the multivalent immunogenic composition of the invention is administered concomitantly with a vaccine against influenza. In certain embodiments, the influenza vaccine is a "senior flu vaccine," a high dose flu vaccine indicated for the elderly, e.g. persons aged 65 and older.

The invention provides a method for inducing a protective immune response in a patient against a pneumococcal infection comprising the step of administering to the patient an immunologically effective amount of any of the multivalent immunogenic pneumococcal polysaccharide-protein conjugate compositions described herein. Optimal amounts of components for a particular vaccine (e.g. a multivalent immunogenic composition of the invention) can be ascertained by standard studies involving observation of appropriate immune responses in subjects. For example, in another embodiment, the dosage for human vaccination is determined by extrapolation from animal studies to human data. In another embodiment, the dosage is determined empirically.

The methods of the invention can be used for the prevention and/or reduction of primary clinical syndromes caused by microbes, e.g., *S. pneumoniae*, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage). In specific embodiments, the compositions of the invention are administered to the patient via intramuscular or subcutaneous administration.

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

Example 1

Preparation of *S. pneumoniae* Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP 0 497 524 B 1. The process described below generally follows the method described in European Patent No. EP 0 497 524 B1 and is generally applicable to all pneumococcal serotypes.

Isolates of pneumococcal strains for serotypes 1, 3, 4, 5, 6A, 6B, 7F, 8, 9V, 10A, 11A, 12F, 14, 15A, 15B, 18C, 19A, 19F, 22F, 23F, 33F, and 35B were obtained from Merck Culture Collection. Strains for serotypes 23B were obtained from Centers of Disease Control and Prevention and University of Alabama Birmingham. Strains for serotype 24F were obtained from Merck Culture Collection and University of Alabama Birmingham. Where needed, subtypes were differentiated on the basis of Quellung reaction using specific antisera. See, e.g., U.S. Pat. No. 5,847,112. The obtained isolates were further clonally isolated by plating serially in two stages on agar plates consisting of an animal-component free medium containing soy peptone, yeast extract, and glucose without hemin. For serotype 7F, the agar plates used also contained hemin. Clonal isolates for each serotype were further expanded in liquid culture using animal-component free media containing soy peptone, yeast extract, HEPES, sodium chloride, sodium bicarbonate, potassium phosphate, glucose, and glycerol to prepare the pre-master cell banks.

The production of each serotype of pneumococcal polysaccharide consisted of a cell expansion and batch production fermentation followed by chemical inactivation prior to downstream purification. A thawed cell bank vial from each serotype was expanded using a shake flask or culture bottle containing a pre-sterilized animal-component free growth media containing soy peptone or soy peptone ultrafiltrate, yeast extract or yeast extract ultrafiltrate, HEPES, sodium chloride, sodium bicarbonate, potassium phosphate, and glucose. The cell expansion culture was grown in a sealed shake flask or bottle to minimize gas exchange with temperature and agitation control. During the cell expansion of these serotypes, temperature, pH, pressure, and agitation were controlled. Airflow overlay was also controlled as sparging was not used. After achieving a specified culture density, as measured by optical density at 600 nm, a portion of the cell expansion culture was transferred to a production fermentor containing pre-sterilized animal-component free growth media containing soy peptone or soy peptone ultrafiltrate, yeast extract or yeast extract ultrafiltrate, sodium chloride, potassium phosphate, and glucose. Temperature, pH, pressure, and agitation were controlled. Airflow overlay was also controlled as sparging was not used.

The batch fermentation was terminated via the addition of a chemical inactivating agent, phenol, when glucose was nearly exhausted. Pure phenol was added to a final concentration of 0.8-1.2% to inactivate the cells and liberate the capsular polysaccharide from the cell wall. Primary inactivation occurs for a specified time within the fermentor where temperature and agitation continue to be controlled. After primary inactivation, the batch was transferred to another vessel where it was held for an additional specified time at controlled temperature and agitation for complete inactivation. This was confirmed by either microbial plating techniques or by verification of the phenol concentration and specified time. The inactivated broth was then purified.

Example 2

Purification of Pneumococcal Polysaccharides

The purification process for the pneumococcal polysaccharides consisted of several centrifugation, depth filtration, concentration/diafiltration operations, and precipitation steps. All procedures were performed at room temperature unless otherwise specified.

Inactivated broth from the fermentor cultures of *S. pneumoniae* were flocculated with a cationic polymer (such as BPA-1000, TRETOLITE® (Baker Hughes Inc., Houston, TX), Spectrum 8160, poly(ethyleneimine), and Millipore pDADMAC). The cationic polymers binded to the impurity proteins, nucleic acids and cell debris. Following the flocculation step and an aging period, flocculated solids were removed via centrifugation and multiple depth filtration steps. Clarified broth was concentrated and diafiltered using a 100 kDa to 500 kDa MWCO (molecular weight cutoff) filter. Diafiltration was accomplished using Tris, $MgCl_2$ buffer and sodium phosphate buffer. Diafiltration removed residual nucleic acid and protein.

Removal of further impurities was accomplished by reprecipitation of the polysaccharide in sodium acetate and phenol with denatured alcohol and/or isopropanol. During the phenol precipitation step, sodium acetate in sodium phosphate saline buffer and phenol (liquefied phenols or solid phenols) were charged to the diafiltered retentate. Alcohol fractionation of the polysaccharide was then conducted in two stages. In the first stage a low percent alcohol was added to the preparation to precipitate cellular debris and other unwanted impurities, while the crude polysaccharide remained in solution. The impurities were removed via centrifugation followed by a depth filtration step. The polysaccharide was then recovered from the solution by adding additional isopropanol or denatured alcohol to the batch. The precipitated polysaccharide pellet was recovered by centrifugation, triturated and dried as a powder and stored frozen at −70° C.

Example 3

Preparation of Serotype 1 Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in dimethylsulfoxide (DMSO). Redissolved polysaccharide and CRM197 solutions were then combined and conjugated as described below. The resulting conjugate was purified by dialysis prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 250 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 15 hours at 22° C.

The activated product was diafiltered against 10 mM potassium phosphate, pH 6.4 using a 10 kDa NMWCO tangential flow ultrafiltration membrane followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 2.5 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was dialyzed at approximately 4° C. for 3 days against 150 mM sodium chloride, 0.05% (w/v) polysorbate 20, using a 300 kDa NMWCO dialysis cassette.

Final Filtration and Product Storage

The batch was 0.2 micron filtered (with 0.5 micron prefilter), dispensed into aliquots and frozen at ≤−60° C.

Example 4

Preparation of Serotype 1 Conjugate for PCV23 (DMSO+ Aq) Polyvalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 250 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 15 hours at 22° C.

The activated product was diafiltered against 10 mM potassium phosphate, pH 6.4 using a kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was combined with the buffered polysaccharide solution at a polysaccharide to CRM197 mass ratio of 0.5. The mass ratio was selected to control the polysaccharide to CRM197 ratio in the resulting conjugate. The polysaccharide and phosphate concentrations were 6.9 g/L and 100 mM respectively. The polysaccharide concentration was selected to control the size of the resulting conjugate. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered.

The batch was adjusted to a polysaccharide concentration of 1.0 g/L with additional 10 mM L-histidine in 150 mM sodium chloride, pH 7.0 buffer with 0.015% (w/v) polysorbate 20. The batch was dispensed into aliquots and frozen at ≤−60° C.

Example 5

Preparation of Serotype 1 Conjugate for PCV22 Polyvalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 250 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 15 hours at 22° C.

The activated product was diafiltered against 10 mM potassium phosphate, pH 6.4 using a kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was combined with the buffered polysaccharide solution at a polysaccharide to CRM197 mass ratio of 0.5. The mass ratio was selected to control the polysaccharide to CRM197 ratio in the resulting conjugate. The polysaccharide and phosphate concentrations were 6.9 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered.

The batch was adjusted to a polysaccharide concentration of 1.0 g/L with additional 10 mM L-histidine in 150 mM sodium chloride, pH 7.0 buffer with 0.015% (w/v) polysorbate 20. The batch was dispensed into aliquots and frozen at ≤−60° C.

Example 6

Preparation of Serotype 3 Conjugate for PCV 23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in dimethylsulfoxide (DMSO). Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 810 bar/6 passes followed by 900 bar/3 passes.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 12 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 2.5 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.25 g Ps/L and a polysaccharide to CRM197 mass ratio of 1.35. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 7

Preparation of Serotype 3 Conjugate for PCV22 and PCV23 (DMSO+Aq) Polyvalent Studies Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 380 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 12 hours at 22° C.

The activated product was diafiltered against 10 mM potassium phosphate, pH 6.4 using a kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 6.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.6. The mass ratio was selected to control the polysaccharide to CRM197 ratio in the resulting conjugate. The polysaccharide and phosphate concentrations were 4.1 g/L and 150 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours at 10° C. to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. The batch was 0.2 micron filtered.

The batch was adjusted to a polysaccharide concentration of 1.0 g/L with additional 10 mM L-histidine in 150 mM sodium chloride, pH 7.0 buffer. The batch was dispensed into aliquots and frozen at ≤−60° C.

Example 8

Preparation of Serotype 4 Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by dialysis prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes.

Size-reduced polysaccharide was concentrated and diafiltered against water using a 10 kDa NMWCO tangential flow ultrafiltration membrane.

The polysaccharide solution was then adjusted to 50° C. and pH 4.1 with a sodium acetate buffer to partially deketalize the polysaccharide. The polysaccharide solution was then cooled to 22° C. prior to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 using a 10 kDa NMWCO tangential flow ultrafiltration membrane followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 5.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was dialyzed at approximately 4° C. for 3 days against 150 mM sodium chloride, 0.05% (w/v) polysorbate 20, using a 300 kDa NMWCO dialysis cassette.

Final Filtration and Product Storage

The batch was 0.2 micron filtered (with 0.5 micron prefilter), dispensed into aliquots and frozen at ≤−60° C.

Example 9

Preparation of Serotype 4 Conjugate for PCV23 (DMSO+Aq) and PCV22 Polyvalent Studies Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 300 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 50° C. and pH 4.1 with a sodium acetate buffer to partially deketalize the polysaccharide. The polysaccharide solution was then cooled to 22° C. prior to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 using a kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.5. The mass ratio was selected to control the polysaccharide to CRM197 ratio in the resulting conjugate. The polysaccharide and phosphate concentrations were 8.3 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Then the batch was 0.2 micron filtered.

The batch was adjusted to a polysaccharide concentration of 1.0 g/L with additional 10 mM L-histidine in 150 mM sodium chloride, pH 7.0 buffer. The batch was dispensed into aliquots and frozen at ≤−60° C.

Example 10

Preparation of Serotype 5 Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by dialysis prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/5 passes.

Size-reduced polysaccharide was concentrated and diafiltered against water using a 10 kDa NMWCO tangential flow ultrafiltration membrane.

The polysaccharide solution was then adjusted to 4° C. and pH 4.1 with a sodium acetate buffer to minimize polysaccharide size reduction due to activation. Polysaccharide activation was initiated with the addition of a 100 mM sodium metaperiodate solution. The oxidation reaction proceeded for 4 hours at 4° C.

The activated product was diafiltered against 10 mM Sodium Acetate, pH 4.1 using a 10 kDa NMWCO tangential flow ultrafiltration membrane followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 20 mM. The polysaccharide and CRM197 solutions were blended to achieve a polysaccharide concentration of 2.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Dilution and Neutralization

The batch was diluted into 150 mM sodium chloride, with approximately 0.025% (w/v) polysorbate 20, at approximately 4° C. Potassium phosphate buffer was then added to neutralize the pH. The batch was dialyzed at approximately 4° C. for 3 days against 150 mM sodium chloride, 0.05% (w/v) polysorbate 20, using a 300 kDa NMWCO dialysis cassette.

Final Filtration and Product Storage

The retentate batch was 0.2 micron filtered (with 0.5 micron prefilter), dispensed into aliquots and frozen at ≤−60° C.

Example 11

Preparation of Serotype 5 Conjugate for PCV22 and PCV23 (DMSO+Aq) Polyvalent Studies Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass.

Homogenization pressure and number of passes through the homogenizer were controlled to 600 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 4° C. and pH 4.1 with a sodium acetate buffer to minimize polysaccharide size reduction due to activation. Polysaccharide activation was initiated with the addition of a 100 mM sodium metaperiodate solution. The oxidation reaction proceeded for 4 hours at 4° C.

The activated product was diafiltered against 10 mM sodium acetate, pH 4.1 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 6.0. The buffer pH selected was to improve the stability of activated polysaccharide during the conjugation reaction. Purified CRM197, obtained through expression in *Pseudomonas fluorescens* as previously described (WO 2012/173876 A1), was combined with the buffered polysaccharide solution at a polysaccharide to CRM197 mass ratio of 0.4. The mass ratio was selected to control the polysaccharide to CRM197 ratio in the resulting conjugate. The polysaccharide and phosphate concentrations were 3.8 g/L and 150 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 96 hours to maximize consumption of polysaccharide and protein.

Purification and Neutralization

Following the conjugation reaction, the batch was diluted to a polysaccharide concentration of approximately 3.5 g/L, cooled to 2-8° C., and 1.2-micron filtered. The batch was diafiltered against 300 mM sodium bicarbonate pH 9.3 at 2-8° C. using a 100 kDa NMWCO tangential flow ultrafiltration membrane. The batch, recovered in the retentate, was then neutralized with 1.5 M potassium phosphate, pH 6.0.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) and then the batch was 0.2 micron filtered.

The batch was adjusted to a polysaccharide concentration of 1.0 g/L with additional 10 mM L-histidine in 150 mM sodium chloride, pH 7.0 buffer with 0.015% (w/v) polysorbate 20. The batch was dispensed into aliquots and frozen at ≤−60° C.

Example 12

Preparation of Serotype 6A Conjugate for PCV23 (DMSO) and PCV23 (DMSO+Aq) and PCV 22 Polyvalent Studies Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes. Size-reduced polysaccharide was concentrated and diafiltered against water using a kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.5 g Ps/L and a polysaccharide to CRM197 mass ratio of 1.4. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 13

Preparation of Serotype 6B Conjugate for PCV 23 (DMSO) and PCV 23 (DMSO/Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.85 g Ps/L and a polysaccharide to CRM197 mass ratio of 1.35. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 14

Preparation of Serotype 6B Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes. Size-reduced polysaccharide was concentrated and diafiltered against water using a kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.75 g Ps/L and a polysaccharide to CRM197 mass ratio of 1.35. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane. The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 15

Preparation of Serotype 7F Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 150 bar/7 passes. Size-reduced polysaccharide was concentrated and diafiltered against water using a kDa NMWCO tangential flow ultrafiltration membrane.

The polysaccharide solution was then adjusted to 4° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 4° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.6 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 16

Preparation of Serotype 7F Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 150 bar/7 passes. Size-reduced polysaccharide was concentrated and diafiltered against water using a kDa NMWCO tangential flow ultrafiltration membrane.

The polysaccharide solution was then adjusted to 4° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 4° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.04 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 17

Preparation of Serotype 8 Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/6 passes. Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 4.5 g Ps/L and a polysaccharide to CRM197 mass ratio of 1.5. The mass ratio was selected to control the polysaccharide to CRM197 ratio in the resulting conjugate. After the blend, the conjugation reaction proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 18

Preparation of Serotype 9V Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 230 bar/5.5 passes. Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 6 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 1.3. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with a 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 19

Preparation of Serotype 9V Conjugate for PCV22 Polyvalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 100 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 6 hours at 22° C.

The activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.7. The mass ratio was selected to control the polysaccharide to CRM197 ratio in the resulting conjugate. The polysaccharide and phosphate concentrations were 10.0 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diaftiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered.

The batch was adjusted to a polysaccharide concentration of 1.0 g/L with additional 10 mM L-histidine in 150 mM sodium chloride, pH 7.0 buffer with 0.015% (w/v) polysorbate 20. The batch was dispensed into aliquots and frozen at ≤−60° C.

Example 20

Preparation of Serotype 9V Conjugate for PCV23 (DMSO+Aq) Polyvalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 100 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 6 hours at 22° C.

The activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.7. The mass ratio was selected to control the polysaccharide to CRM197 ratio in the resulting conjugate. The polysaccharide and phosphate concentrations were 10.0 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered.

The batch was adjusted to a polysaccharide concentration of 1.0 g/L with additional 10 mM L-histidine in 150 mM sodium chloride, pH 7.0 buffer with 0.015% (w/v) polysorbate 20. The batch was dispensed into aliquots and frozen at ≤−60° C.

Example 21

Preparation of Serotype 10A Conjugate for PCV23 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 615 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.5 g Ps/L and a polysaccharide to CRM197 mass ratio of 1.6. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 22

Preparation of Serotype 10A Conjugate for PCV23 (DMSO+Aq) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/5 passes. Size-reduced polysaccharide was concentrated and diafiltered against water using a kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.4 g Ps/L and a polysaccharide to CRM197 mass ratio of 1.6. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 150 mM sodium chloride, 25 mM potassium phosphate, pH 7 followed by diafiltration against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 23

Preparation of Serotype 10A Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/5 passes. Size-reduced polysaccharide was concentrated and diafiltered against water using a kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.8 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example X

Preparation of Serotype 11A Conjugate for PCV24 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 800 bar/8 passes. Size-reduced polysaccharide was concentrated and diafiltered against water using a kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.3 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 24

Preparation of Serotype 12F Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 80° C. for 155 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.7 g Ps/L and a polysaccharide to CRM197 mass ratio of 1.8. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 25

Preparation of Serotype 12F Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 60 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7.0, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 26

Preparation of Serotype 14 Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by dialysis prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/6 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.8 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was dialyzed at approximately 4° C. for 22.5 hours against 150 mM sodium chloride, 0.05% polysorbate 20, using a 300 kDa MWCO dialysis cassette.

Final Filtration and Product Storage

The retentate batch was 0.2 micron filtered (with 0.5 micron prefilter), dispensed into aliquots and frozen at ≤−60° C.

Example 27

Preparation of Serotype 14 Conjugate for PCV22 and PCV23 (DMSO+Aq) Polyvalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 200 bar/6 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 using a kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 1.0. The mass ratio was selected to control the polysaccharide to CRM197 ratio in the resulting conjugate. The polysaccharide and phosphate concentrations were 3.8 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 72 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. The batch was then 0.2 micron filtered.

The batch was adjusted to a polysaccharide concentration of 1.0 g/L with additional 10 mM L-histidine in 150 mM

Example 28

Preparation of Serotype 15A Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 210 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO which was preheated to 34° C. The polysaccharide solution was spiked with sodium chloride to a concentration of 25 mM. The polysaccharide and CRM197 solutions were blended to achieve a polysaccharide concentration of 5.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded at 34° C.

Reduction with Sodium Borohydride

Sodium borohydride (2 moles per mole of polysaccharide repeating unit) was added following the conjugation reaction and incubated for 1 hour at 34° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 29

Preparation of Serotype 15A Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO which was preheated to 34° C. The polysaccharide solution was spiked with sodium chloride to a concentration of 25 mM. The polysaccharide and CRM197 solutions were blended to achieve a polysaccharide concentration of 5.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded at 34° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 30

Preparation of Serotype 15C Conjugate for PCV23 (DMSO) and PCV23 (DMSO+Aq) Polyvalent Studies Using DMSO Conjugation Polysaccharide derived from *Streptococcus pneumoniae* serotype 15B was dissolved, sized to a target molecular mass, subjected to mild base hydrolysis to release O-acetyl groups, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction, Base Hydrolysis and Oxidation

Purified serotype 15B pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes.

Size-reduced polysaccharide was concentrated and diafiltered against water using a 10 kDa NMWCO tangential flow ultrafiltration membrane.

The polysaccharide solution was heated to 60° C. and sodium bicarbonate pH 9 buffer was added to a final concentration of 50 mM. The batch was incubated with mixing for 13 hours at 60° C. to release O-acetyl groups. Potassium phosphate pH 6 buffer was added to a final concentration of 136 mM to neutralize pH and the solution was cooled to ambient temperature. The solution was then concentrated and diafiltered against water using a 10 kDa NMWCO tangential flow ultrafiltration membrane.

The polysaccharide solution was adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 31

Preparation of Serotype 15C Conjugate for PCV22 Polyvalent Study Using DMSO Conjugation Polysaccharide derived from *Streptococcus pneumoniae* serotype 15B was dissolved, sized to a target molecular mass, subjected to mild base hydrolysis to release O-acetyl groups, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction, Base Hydrolysis and Oxidation

Purified serotype 15B pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes. The size-reduced polysaccharide solution was heated to 60° C. and sodium bicarbonate pH 9.4 buffer was added to a final concentration of 50 mM. The batch was incubated with mixing for 12 hours at 60° C. to release O-acetyl groups. Potassium phosphate pH 6 buffer was added to a final concentration of 150 mM to neutralize pH and the solution was cooled to ambient temperature. The solution was then concentrated and diafiltered against water using a 10 kDa NMWCO tangential flow ultrafiltration membrane.

The polysaccharide solution was adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.2 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 32

Preparation of Serotype 18C Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 160 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.49 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 33

Preparation of Serotype 18C Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 160 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered. Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.49 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 34

Preparation of Serotype 19A Conjugate for PCV23 (DMSO) and PCV23 (DMSO+Aq) Polyvalent Studies Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.22-micron filtered. The polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v.

CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.8 g Ps/L and a polysaccharide to CRM197 mass ratio of 1.33. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 35

Preparation of Serotype 19A Conjugate for PCV22 Polyvalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.22-micron filtered. The polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.8 g Ps/L and a polysaccharide to CRM197 mass ratio of 1.33. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 36

Preparation of Serotype 19F Conjugate for PCV23 (DMSO), PCV23 (DMSO+Aq) and PCV22 Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 150 bar/5 passes.

Size-reduced polysaccharide was concentrated and diafiltered against water using a 10 kDa NMWCO tangential flow ultrafiltration membrane.

The polysaccharide solution was then adjusted to 4° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 4° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.0 g Ps/L and a polysaccharide to CRM197 mass ratio of 1.2. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane. The retentate batch was 0.2 micron filtered then incubated at 22° C. for 4.5 days.

Final Filtration and Product Storage

The batch was then concentrated and diafiltered against 10 mM histidine in 150 mM sodium chloride, pH 7.0 at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 37

Preparation of Serotype 22F Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 810 bar/5 passes.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.3 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered with 0.5 micron prefilter then diluted with additional 10 mM histidine in 150 mM sodium chloride, pH 7.0 with 0.015% (w/v) polysorbate 20, dispensed into aliquots and frozen at ≤−60° C.

Example 38

Preparation of Serotype 22F Conjugate for PCV22 and PCV23 (DMSO+Aq) Polyvalent Studies Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 350 bar/5 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.6. The mass ratio was selected to control the polysaccharide to CRM197 ratio in the resulting conjugate. The polysaccharide and phosphate concentrations were 7.5 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 120 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diaftiltered against 10 mM L-histidine in 150 mM sodium chloride, pH 7.0 at 4° C. using a 300 kDa NMWCO tangential flow ultrafiltration membrane.

The batch was 0.2 micron filtered and was adjusted to a polysaccharide concentration of 1.0 g/L with additional 10 mM L-histidine in 150 mM sodium chloride, pH 7.0 buffer. The batch was dispensed into aliquots and frozen at ≤−60° C.

Example 39

Preparation of Serotype 23B Conjugate for PCV23 (DMSO), PCV23 (DMSO+Aq) and PCV22 Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 5.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 40

Preparation of Serotype 23F Conjugate for PCV23 (DMSO) and PCV23 (DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 5 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.1 g Ps/L and a polysaccharide to CRM197 mass ratio of 1.25. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 41

Preparation of Serotype 23F Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 4 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.1 g Ps/L and a polysaccharide to CRM197 mass ratio of 1.25. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Example 42

Preparation of Serotype 24F Conjugate for PCV23 (DMSO) and PCV23(DMSO+Aq) Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 80° C. for 150 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 2 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 10 mM. The polysaccharide and CRM197 solutions were blended to achieve a polysaccharide concentration of 1.4 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 43

Preparation of Serotype 24F Conjugate for PCV22 Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 80° C. for 150 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 2 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 25 mM. The polysaccharide and CRM197 solutions were blended to achieve a polysaccharide concentration of 1.4 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 44

Preparation of Serotype 33F Conjugate for PCV23 (DMSO) Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 510 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.5 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 45

Preparation of Serotype 33F Conjugate for PCV22 and PCV23 (DMSO+Aq) Polyvalent Studies Using Aqueous Conjugation Polysaccharide was dissolved, size reduced, chemically activated and buffer-exchanged by ultrafiltration. Purified CRM197 was then conjugated to the activated polysaccharide utilizing nickel chloride in the reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 350 bar/4 passes to size-reduce to a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.7. The mass ratio was selected to control the polysaccharide to CRM197 ratio in the resulting conjugate. The polysaccharide and phosphate concentrations were 6.5 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 96 hours to maximize consumption of polysaccharide and protein.

Reduction with Sodium Borohydride

Following the conjugation reaction, the batch was diluted to a polysaccharide concentration of approximately 3.5 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. The batch was 0.2 micron filtered and was adjusted to a polysaccharide concentration of 1.0 g/L with additional 10 mM L-histidine in 150 mM sodium chloride, pH 7.0 buffer. The batch was dispensed into aliquots and frozen at ≤−60° C.

Example 46

Preparation of Serotype 35B Conjugate for PCV23 (DMSO) and PCV23 (DMSO+Aq) Polyvalent Studies Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and $CRM_{197}$ materials were redissolved individually in equal volumes of DMSO. The polysaccharide solution was spiked with sodium chloride to a final concentration of 20 mM. The polysaccharide and CRM197 solutions were blended to achieve a polysaccharide concentration of 6.0 g Ps/L and a polysaccharide to CRM197 mass ratio of 3.0. The mass ratio was selected to control the polysaccharide to CRM197 ratio in the resulting conjugate. Conjugation proceeded at 34° C.

Reduction with Sodium Borohydride

Sodium borohydride (2 moles per mole of polysaccharide repeating unit) was added following the conjugation reaction and incubated for 1 hour at 34° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example 47

Preparation of Serotype 35B Conjugate for PCV22 Polyvalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharide was formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and $CRM_{197}$ materials were redissolved individually in equal volumes of DMSO. The polysaccharide solution was spiked with sodium chloride to a final concentration of 20 mM. The polysaccharide and CRM197 solutions were blended to achieve a polysaccharide concentration of 6.0 g Ps/L and a polysaccharide to CRM197 mass ratio of 3.0. The mass ratio was selected to control the polysaccharide to CRM197 ratio in the resulting conjugate. Conjugation proceeded at 34° C.

Reduction with Sodium Borohydride

Sodium borohydride (2 moles per mole of polysaccharide repeating unit) was added following the conjugation reaction and incubated for 1 hour at 34° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

Example Y

Preparation of Serotypes for PCV24 Polyvalent Study Using DMSO Conjugation

Conjugates were prepared for the PCV24 study using methods similar to those described in prior Examples. For each serotype, polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration.

Several process parameters within each step, such as pH, temperature, concentration, and time were controlled to yield conjugates with desired attributes. Differences from prior Examples may include: homogenization pressure and number of passes, oxidation time, polysaccharide and sucrose concentration for lyophilization, polysaccharide concentration during conjugation, polysaccharide to CRM197 mass ratio and salt concentration in the conjugation reaction.

Example 48

Formulation of Pneumococcal Conjugate Vaccines

Individual pneumococcal polysaccharide-protein conjugates prepared utilizing different chemistries as described in the Examples, supra, were used for the formulation of an 8-, 15-, 22-, 23- & 24-valent pneumococcal conjugate vaccines.

The PCV8/APA vaccine drug product is prepared by individually conjugating the CRM197 protein to Pneumococcal polysaccharide (PnPs) Types (-8, -10A, -12F, -15A, -15C, -23B, -24F and -35B) using reductive amination in an aprotic solvent (also referred to as DMSO chemistry) and formulated in 20 mM L-Histidine pH 5.8 and 150 mM NaCl 0.1% w/v Polysorbate-20 (PS-20) and 250 μg [Al]/mL in the form of Aluminum Phosphate Adjuvant as the adjuvant at 4 μg/mL each serotype for a total polysaccharide concentration of 32 μg/mL.

The PCV15/APA vaccine drug product is prepared by individually conjugating the CRM197 protein to Pneumococcal polysaccharide (PnPs) Types (-6A, -6B, -7F, -9V, -18C, -19A, -19F, -23F) using reductive amination in an aprotic solvent (also referred to as DMSO chemistry) or for Types-1, -3, -4, -5, -14, -22F and -33F using reductive amination in a protic solvent (also referred to as aqueous chemistry) and formulated in 20 mM L-Histidine pH 5.8 and 150 mM NaCl 0.2% w/v Polysorbate-20 (PS-20) and 250 µg [Al]/mL in the form of Aluminum Phosphate as the adjuvant at 4 µg/mL each serotype (except 6B at 8 µg/mL) for a total polysaccharide concentration of 64 µg/mL.

The PCV22 vaccine drug product used to immunize mice and rabbits was prepared by individually conjugating the CRM197 protein to Pneumococcal polysaccharide (PnPs) Types (-1, -3, -4, -5, -6A, -6B, -7F, -9V, -10A, -12F, -14, -15A, -15C, -18C, -19A, -19F, -22F, -23B, -23F, -24F, -33F, and -35B) using reductive amination in a protic and aprotic solutions (DMSO/Aqueous "Aq") and formulated in 20 mM L-Histidine pH 5.8 and 150 mM NaCl and 0.2% w/v Polysorbate-20 (PS-20) at 0.8 µg/mL each serotype (except 6B at 1.6 µg/mL) for a total polysaccharide concentration of 18.4 µg/mL referred to as PCV22 unadjuvanted or unadj. In another specific embodiment, the formulation is prepared with 50 µg [Al]/mL in the form of Aluminum Phosphate as the adjuvant referred to as PCV22/APA.

The PCV23 vaccine drug product is prepared by individually conjugating the CRM197 protein to Pneumococcal polysaccharide (PnPs) Types (-1, -3, -4, -5, -6A, -6B, -7F, -8, -9V, -10A, -12F, -14, -15A, -15C, -18C, -19A, -19F, -22F, -23B, -23F, -24F, -33F, and -35B) using reductive amination in an aprotic solvent (also referred to as DMSO chemistry) and formulated in 20 mM L-Histidine pH 5.8 and 150 mM NaCl and 0.2% w/v Polysorbate-20 (PS-20) at 4 µg/mL each—serotype for a total polysaccharide concentration of 92 µg/mL referred to as PCV23 unadjuv. In another specific embodiment, the formulation is prepared with 250 µg [Al]/mL in the form of Aluminum Phosphate Adjuvant as the adjuvant referred to as PCV23/APA. In another embodiment, the PCV23 vaccine drug product is prepared by individually conjugating the CRM197 protein to Pneumococcal polysaccharide (PnPs) Types (-1, -3, -4, -5, -9V, -14, 22F, and -33F) using reductive amination in an protic solvent (also referred to as aqueous chemistry) and conjugating the CRM197 protein to Pneumococcal polysaccharide (PnPs) Types (-6A, -6B, -7F, -8, -10A, -12F, -15A, -15C, -18C, -19A, -19F, -23B, -23F, -24F, and -35B) using reductive amination in an aprotic solvent (also referred to as DMSO chemistry). The vaccine drug product is formulated in 20 mM L-Histidine pH 5.8 and 150 mM NaCl and 0.1% w/v Polysorbate-20 (PS-20) with 0.01% CarboxyMethyl Cellulose (CMC) at 4 µg/mL each serotype (except 6B at 8 µg/mL) for a total polysaccharide concentration of 96 µg/mL and prepared with 250 µg [Al]/mL in the form of Aluminum Phosphate Adjuvant as the adjuvant and referred to as PCV23 (DMSO+Aq)/APA.

The multivalent immunogenic composition PCV24 is prepared by individually conjugating the CRM197 protein to S. pneumoniae polysaccharide (PnPs) serotypes-1, -3, -4, -5, -6A, -6B, -7F, -8, -9V, -10A, -11A, -12F, -14, -15A, -15C, -18C, -19A, -19F, -22F, -23B, -23F, -24F, -33F, and -35B using reductive amination in an aprotic solvent (also referred to as DMSO chemistry) and formulated in 20 mM L-Histidine pH 5.8, 150 mM NaCl and 0.1% w/v Polysorbate-20 (PS-20) at 4 µg/mL or 8 µg/mL of each polysaccharide serotype for a total polysaccharide concentration of 96 µg/mL or 192 µg/mL, respectively, and referred to as "PCV24 unadj". In another specific embodiment, the multivalent immunogenic composition PCV24 is prepared in 20 mM L-Histidine pH 5.8, 150 mM NaCl and 0.2% w/v Polysorbate-20 (PS-20) at 4 µg/mL of each polysaccharide serotype for a total polysaccharide concentration of 96 µg/mL further comprising 250 [Al]/mL in the form of Aluminum Phosphate Adjuvant. This is referred to as "PCV24/APA".

The required volume of bulk conjugates needed to obtain the target concentration of individual serotypes were calculated based on batch volume and concentration of individual bulk polysaccharide concentrations. The individual conjugates were added to a solution of histidine, sodium chloride and Polysorbate-20 (PS-20) to produce a 2×-4× conjugate blend. The formulation vessel containing the conjugate blend is mixed using a magnetic stir bar, sterile filtered into another vessel. The sterile filtered 2×-4× blend is either added to another vessel containing Aluminum Phosphate Adjuvant or diluted with saline to achieve the desired target total polysaccharide, excipient and APA adjuvant (if required) concentrations. The formulations are then filled into glass vials or syringes and stored at 2-8° C.

Example 49

PCV22 Immunogenicity and Functional Antibody in Mice

Young female Balb/c mice (6-8 weeks old, n=10/group) were immunized with 0.1 mL of a 22-valent pneumococcal conjugate vaccine (PCV22/APA or PCV22 unadjuvanted) on day 0, day 14 and day 28. PCV22 was dosed at 0.08 µg of each pneumococcal polysaccharide (1, 3, 4, 5, 6A, 7F, 9V, 10A, 12F, 14, 15A, 15C, 18C, 19A, 19F, 22F, 23B, 23F, 24F, 33F, 35B) and 6B at 0.16 µg and all conjugated to CRM197 unadjuvanted or with 5 µg aluminum phosphate adjuvant (APA) per immunization. Mice were observed at least daily by trained animal care staff for any signs of illness or distress. The vaccine formulations in mice were deemed to be safe and well tolerated, as no vaccine-related adverse events were noted. On day 52 the mice were intratracheally challenged with Streptococcus pneumoniae serotype 24F. Exponential phase cultures of S. pneumoniae were centrifuged, washed, and suspended in sterile PBS. Mice were anesthetized with isoflurane prior to challenge. 105 cfu of S. pneumoniae in 0.1 mL of PBS was placed in the throat of mice hung upright by their incisors. Aspiration of the bacteria was induced by gently pulling the tongue outward and covering the nostrils. Mice were weighed daily and euthanized if weight loss exceeded 20% of starting weight. Blood was collected at 24 hours, 48 hours and 72 hours to assess for bacteremia. Mice were observed at least twice daily by trained animal care staff for any signs of illness or distress. All animal experiments were performed in strict accordance with the recommendations in the Guide for Care and Use of Laboratory Animals of the National Institutes of Health. The mouse experimental protocol was approved by the Institutional Animal Care and Use Committee at Merck & Co., Inc.

Mouse sera were evaluated for IgG immunogenicity using a multiplexed electrochemiluminescence (ECL) assay. This assay was developed for use with mouse serum based on the human assay described by Marchese et al.[3] using technology developed by MesoScale Discovery (a division of MesoScale Diagnostics, LLC, Gaithersburg, MD) which utilizes a SULFO-TAG™ label that emits light upon electrochemical stimulation. SULFOTAG™-labeled anti-mouse IgG was used as the secondary antibody for testing mouse serum samples. Functional antibody was determined through multiplexed opsonophagocytic assays (MOPA) based on previously described protocols at www.vaccine.uab.edu and Opsotiter® 3 software owned by and licensed from University of Alabama (UAB) Research Foundation[1,2].

Figure 2:
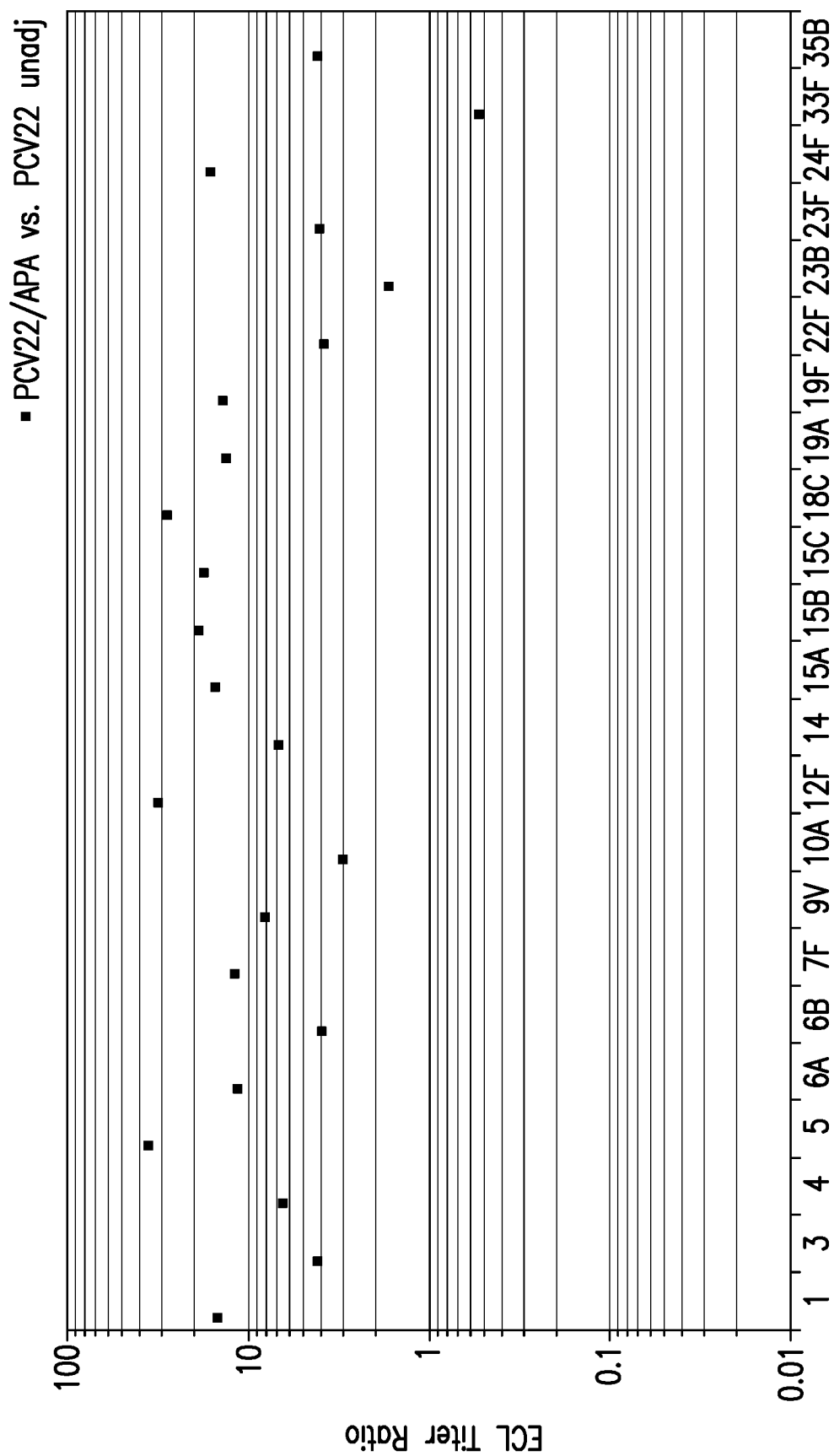
FIG. 2. ECL dilution titer ratio of PCV22/APA compared to PCV22 unadjuvanted (PCV22 unadj) at PD3.

Mouse sera were pooled for each group and tested in multiplexed electrochemiluminescent assays to determine antibody titers. PCV22 generated antibody titers in mice for all serotypes following 1, 2 and 3 immunizations with the vaccine (FIG. 1). PCV22 showed cross-reactivity to serotype 15B, as evidenced by IgG titers (FIG. 1). PCV22 formulated with APA trended toward higher immunogenicity compared to unadjuvanted PCV22 in mice at PD2 (data not shown) and PD3 (FIG. 2).

Figure 3:
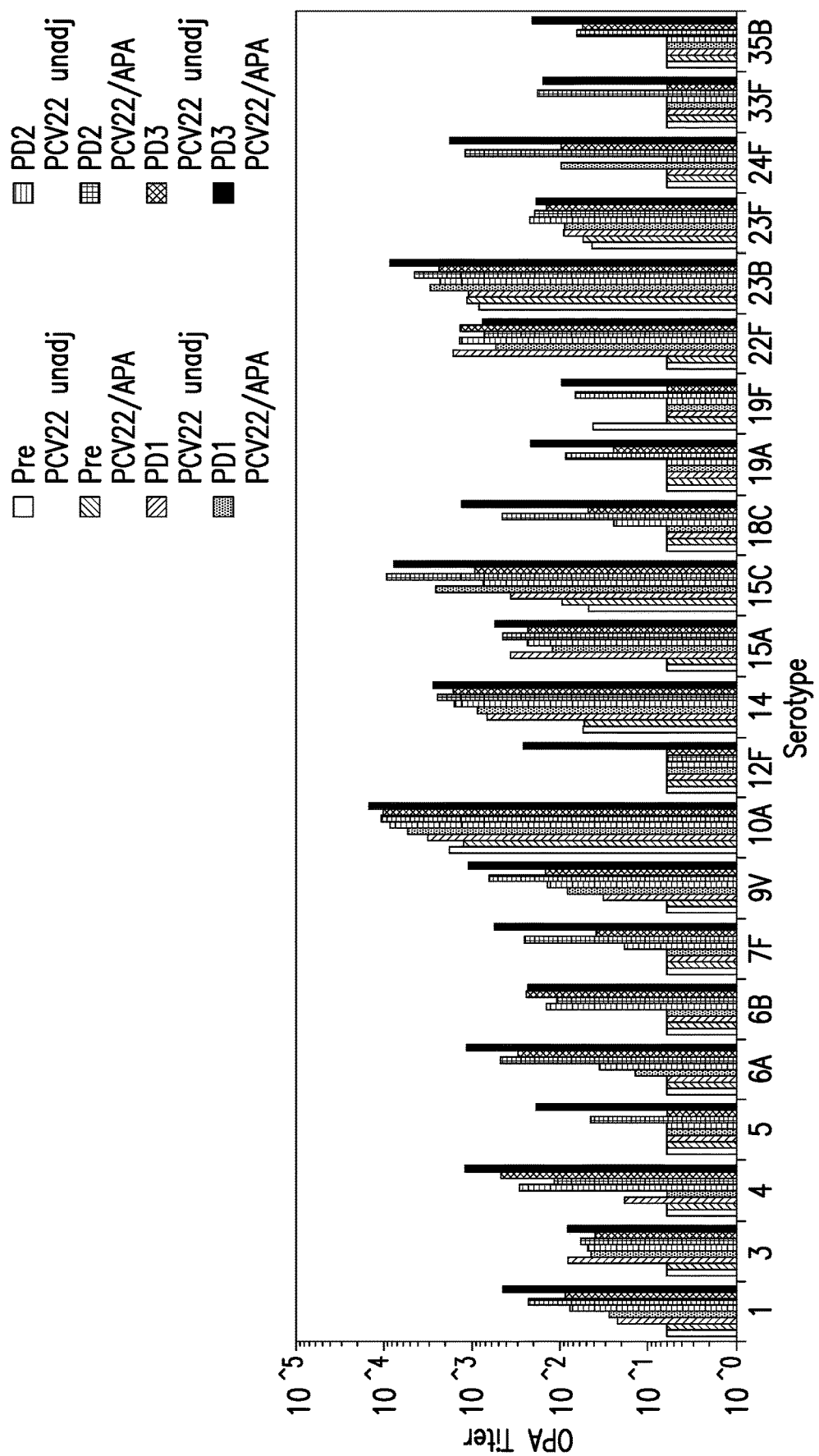
FIG. 3. Serotype specific OPA dilution titers (pre-immune, PD1, PD2, PD3) for mice immunized with PCV22 unadjuvanted (PCV22 unadj) or formulated with APA (PCV22/APA). Reading from left to right; Pre PCV22 unadj, Pre PCV22/APA, PD1 PCV22 unadj, PD1 PCV22/APA, PD2 PCV22 unadj, PD2 PCV22/APA, PD3 PCV22 unadj, and PD3 PCV22/APA.
Figure 4:
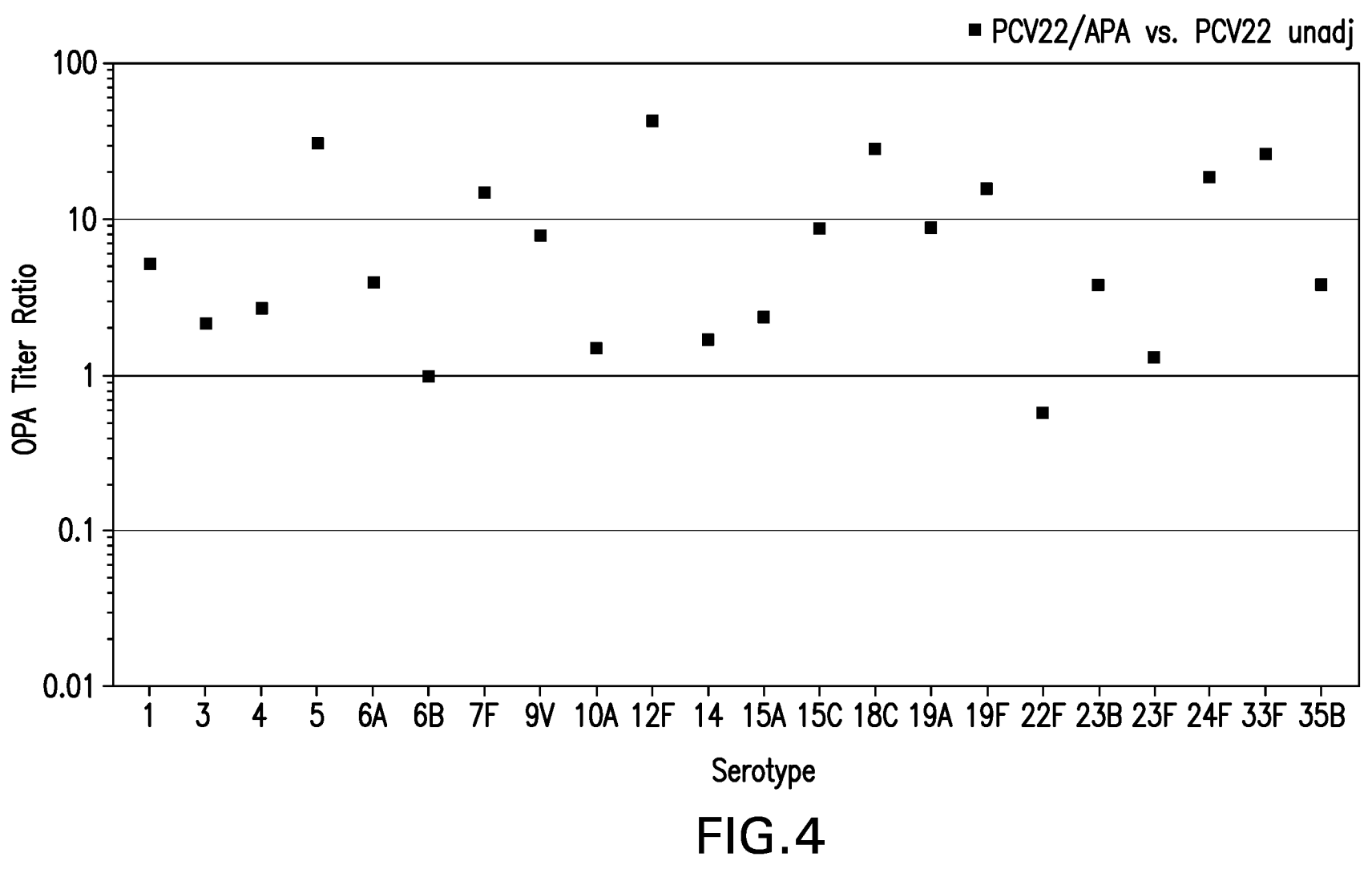

Mouse sera were pooled for each group and tested in multiplexed opsonophagocytic assays (MOPA) to determine functional antibody titers. PCV22 generated functional antibody titers in mice which killed vaccine-type bacterial serotypes following 3 immunizations with the vaccine (FIG. 3). PCV22 formulated with APA trended toward higher functional antibody titers compared to PCV22 unadjuvanted at PD2 (data not shown) and PD3 (FIG. 4), similar to IgG titers (FIG. 2).

Figure 5:
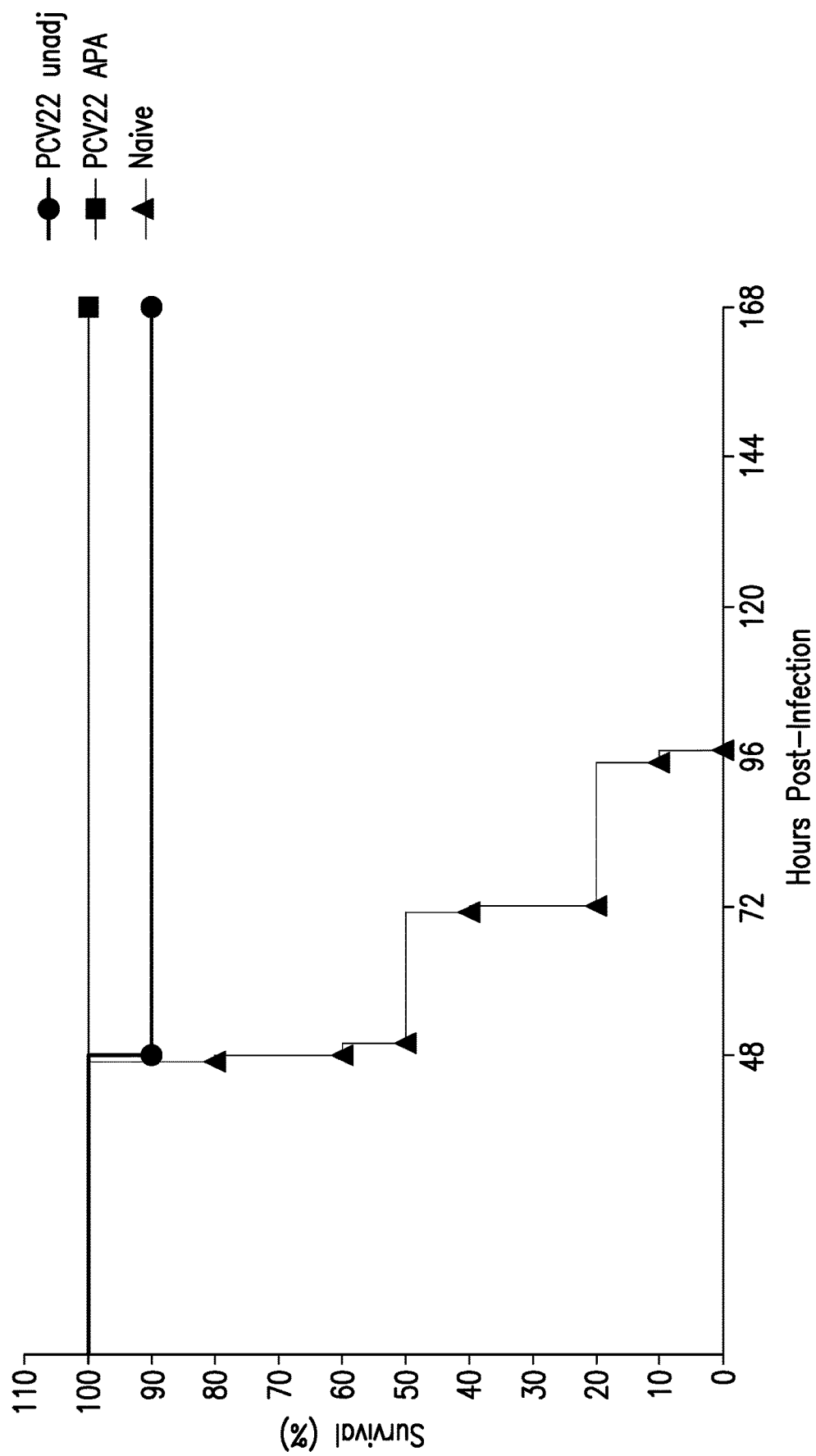
FIG. 5. PCV22 immunized mice are protected from S. pneumoniae 24F intra tracheal challenge.

PCV22 immunized mice were protected from intratracheal challenge with *S. pneumoniae* 24F (FIG. 5). Mantel Cox log-rank test indicated that both the PCV22 unadjuvanted (PCV22 unadj) and PCV22/APA groups were significantly protected from challenge when compared to the naïve group (P<0.0001). Likewise, both PCV22 immunized mouse groups had little to no bacteremia, which was significantly less when compared to the naïve group (data not shown).

Example 50

PCV22 Immunogenicity and Functional Antibody in Rabbits

Adult New Zealand white rabbits (NZWR, n=5/group) were intramuscularly (IM) immunized with 0.1 mL of a 22-valent pneumococcal conjugate vaccine (PCV22/APA or PCV22 unadjuvanted) on day 0 and day 14 (alternating sides). PCV22 was dosed at 0.08 µg of each pneumococcal polysaccharide (1, 3, 4, 5, 6A, 7F, 9V, 10A, 12F, 14, 15A, 15C, 18C, 19A, 19F, 22F, 23B, 23F, 24F, 33F, 35B) and 6B at 0.16 µg and all conjugated to CRM197 and either unadjuvanted or formulated with 5 µg APA per immunization. Sera were collected prior to study start (pre-immune) and on days 14 (PD1) and 28 (PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

Rabbit sera were evaluated for IgG immunogenicity using a multiplexed electrochemiluminescence (ECL) assay. This assay was developed for use with rabbit serum based on the human assay described by Marchese et al.[3] using technology developed by MesoScale Discovery (a division of MesoScale Diagnostics, LLC, Gaithersburg, MD) which utilizes a SULFO-TAG™ label that emits light upon electrochemical stimulation. SULFOTAG™-labeled anti-rabbit IgG was used as the secondary antibody for testing NZWR serum samples. Functional antibody was determined through multiplexed opsonophagocytic assays (MOPA) based on previously described protocols at www.vaccine.uab.edu and Opsotiter® 3 software owned by and licensed from University of Alabama (UAB) Research Foundation[1, 2].

Figure 6:
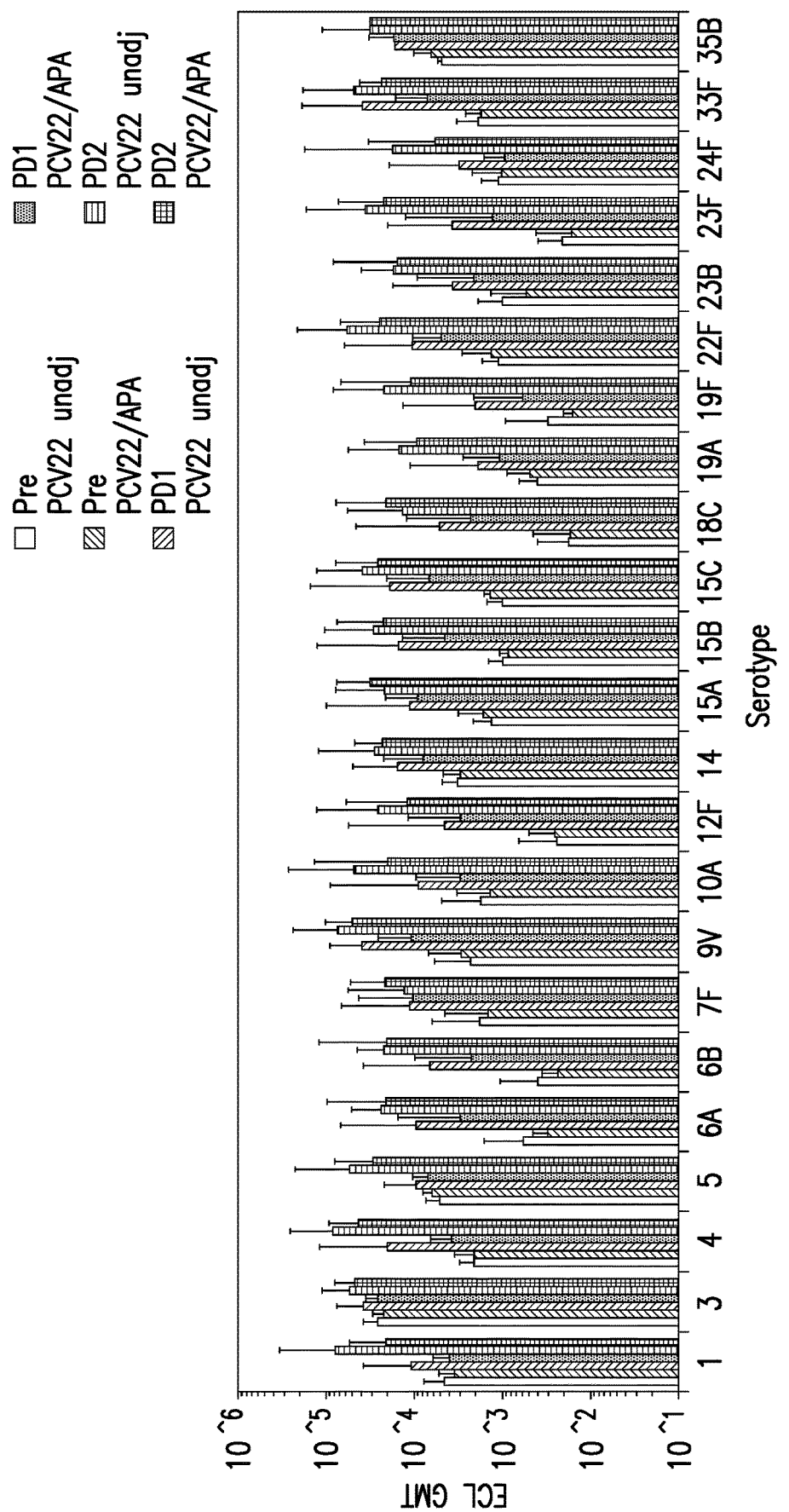
FIG. 6. Pre-immune (Pre), PD1 and PD2 IgG antibody dilution titers as determined by ECL for rabbits immunized with PCV22 unadjuvanted or PCV22/APA. Error bars represent the 95% confidence intervals (CI) of the geometric mean titer (GMT). Reading from left to right; Pre PCV22 unadj, Pre PCV22/APA, PD1 PCV22 unadj, PD1 PCV22/APA, PD2 PCV22 unadj, and PD2 PCV22/APA.
Figure 7:
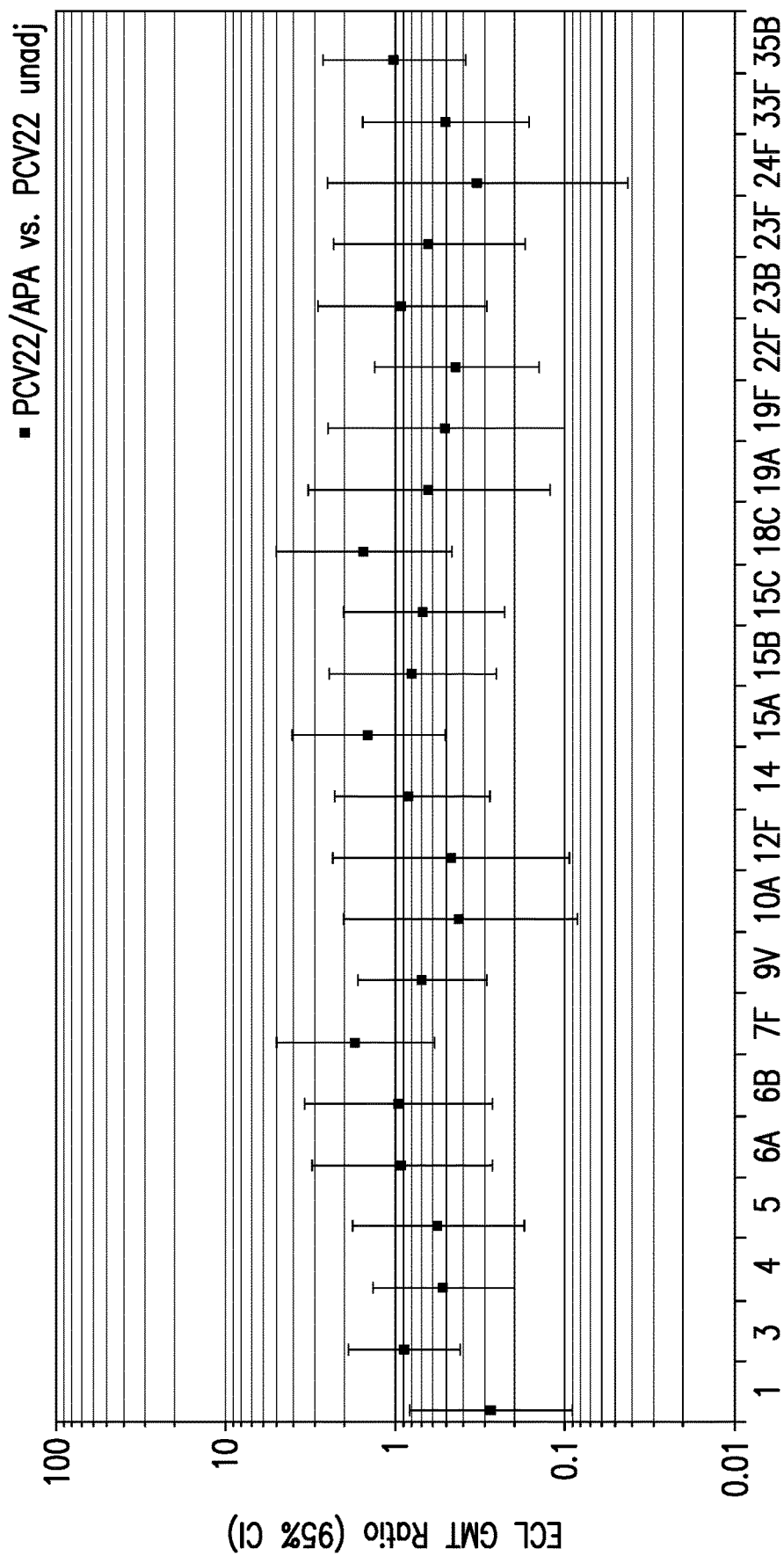
FIG. 7. ECL GMT ratio of PCV22/APA compared to PCV22 unadjuvanted at PD2. Error bars represent the 95% confidence intervals (CI).

Rabbit sera were tested individually in multiplexed electrochemiluminescent assays to determine antibody titers. PCV22 generated antibody titers in rabbits for all serotypes following immunizations with the vaccine (FIG. 6). Immunization of rabbits with PCV22 also generates antibodies that bind to serotype 15B polysaccharide (FIG. 6). There was no benefit to including APA with PCV22 in rabbits, as the immunogenicity was comparable to or lower than (serotype 1) PCV22 unadjuvanted at PD2 (FIG. 7).

Figure 8:
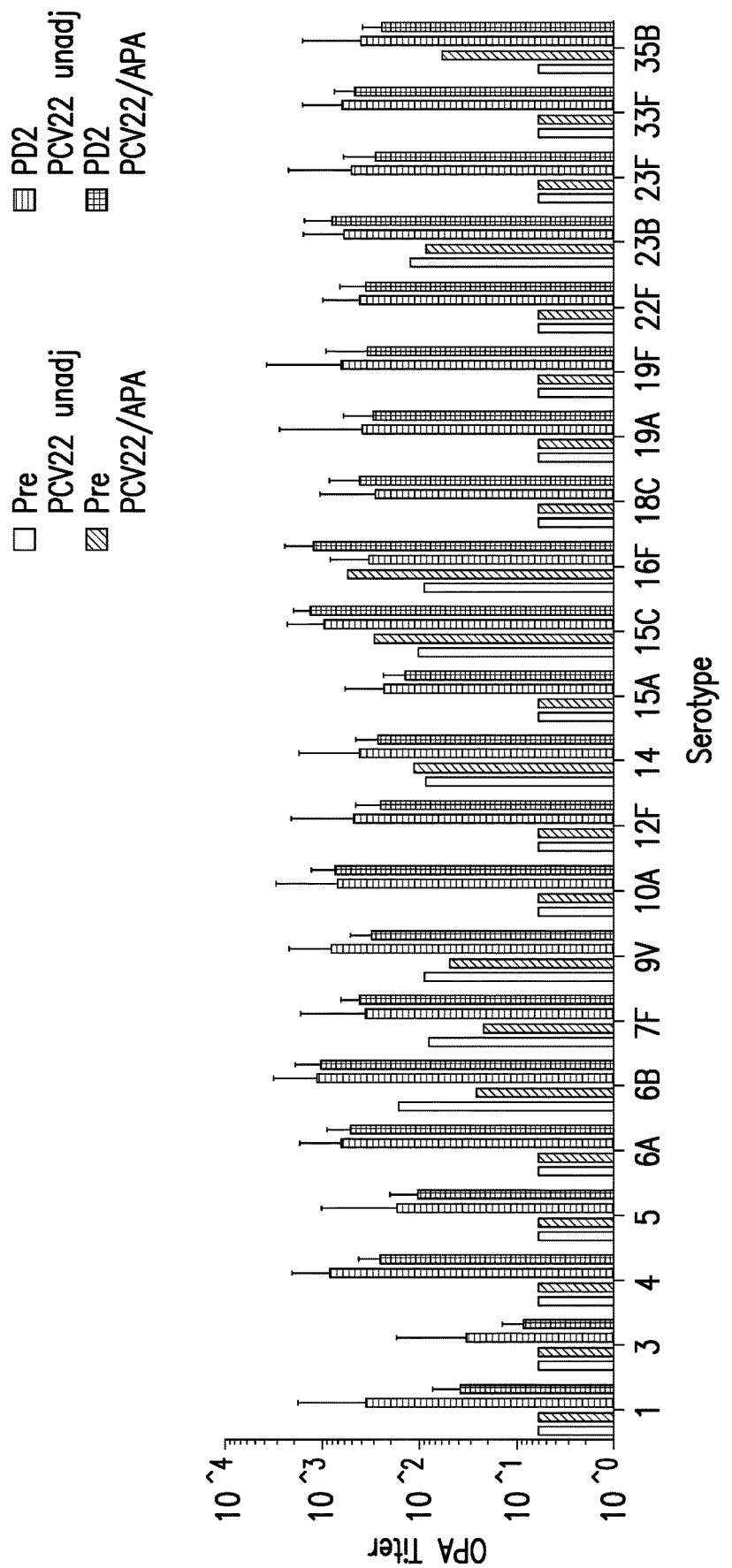
FIG. 8. Serotype specific OPA dilution titers (pre-immune "Pre" and PD2) for rabbits immunized with PCV22 unadjuvanted or PCV22/APA. Error bars represent the variation in functional antibody titers for five rabbits.
Figure 9A:
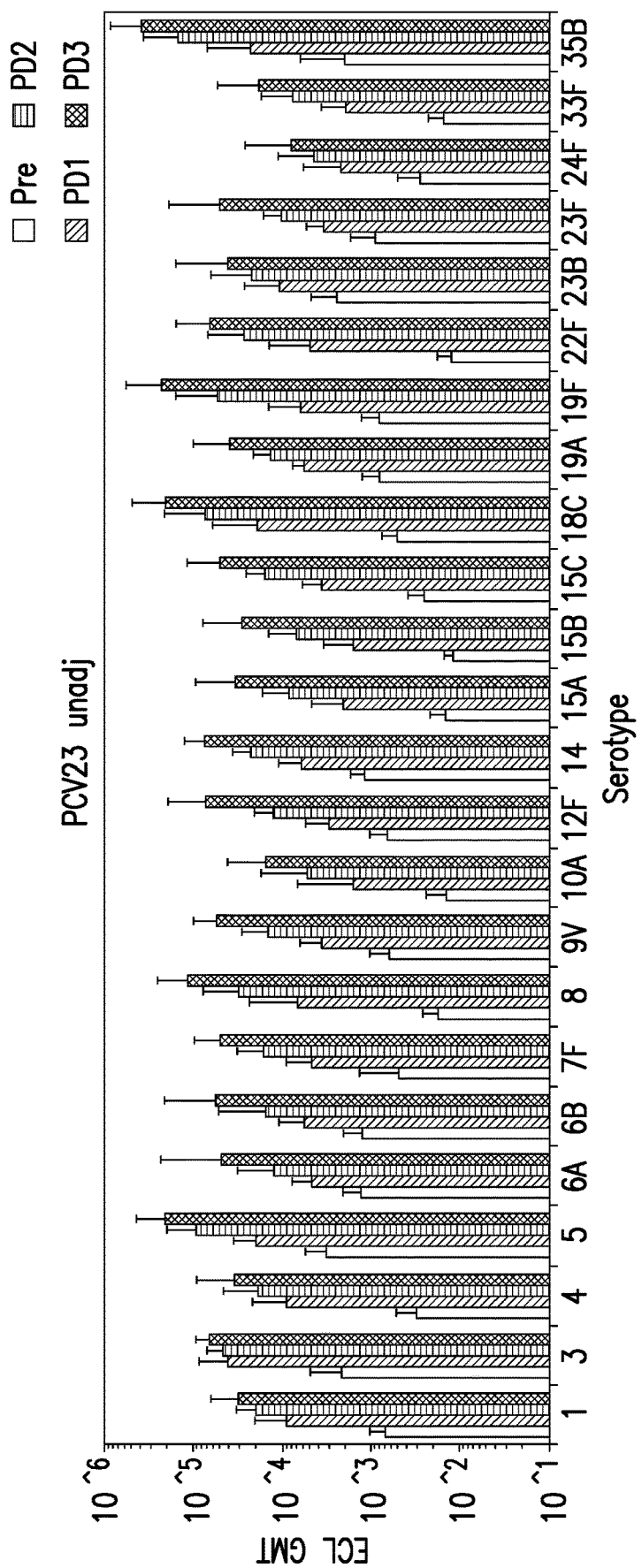
FIG. 9. Pre-immune (Pre), PD1, PD2, and PD3 IgG antibody dilution titers as determined by ECL for IRMs immunized with A) PCV23 unadjuvanted, B) PCV23 (DMSO)/APA, C) PCV23(DMSO+Aq)/APA, and D) PCV15/APA+PCV8/APA. Error bars represent the 95% confidence intervals (CI) of the geometric mean titer (GMT).
Figure 9B:
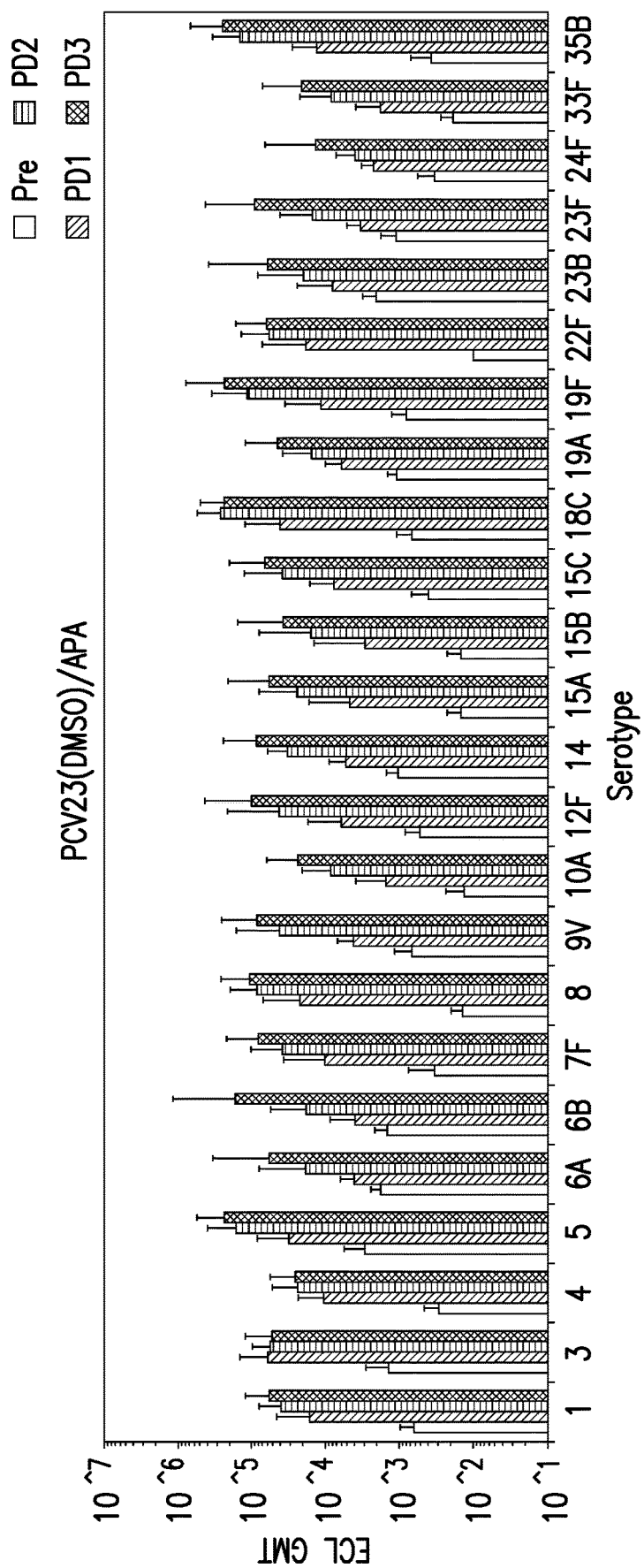
Figure 9C:
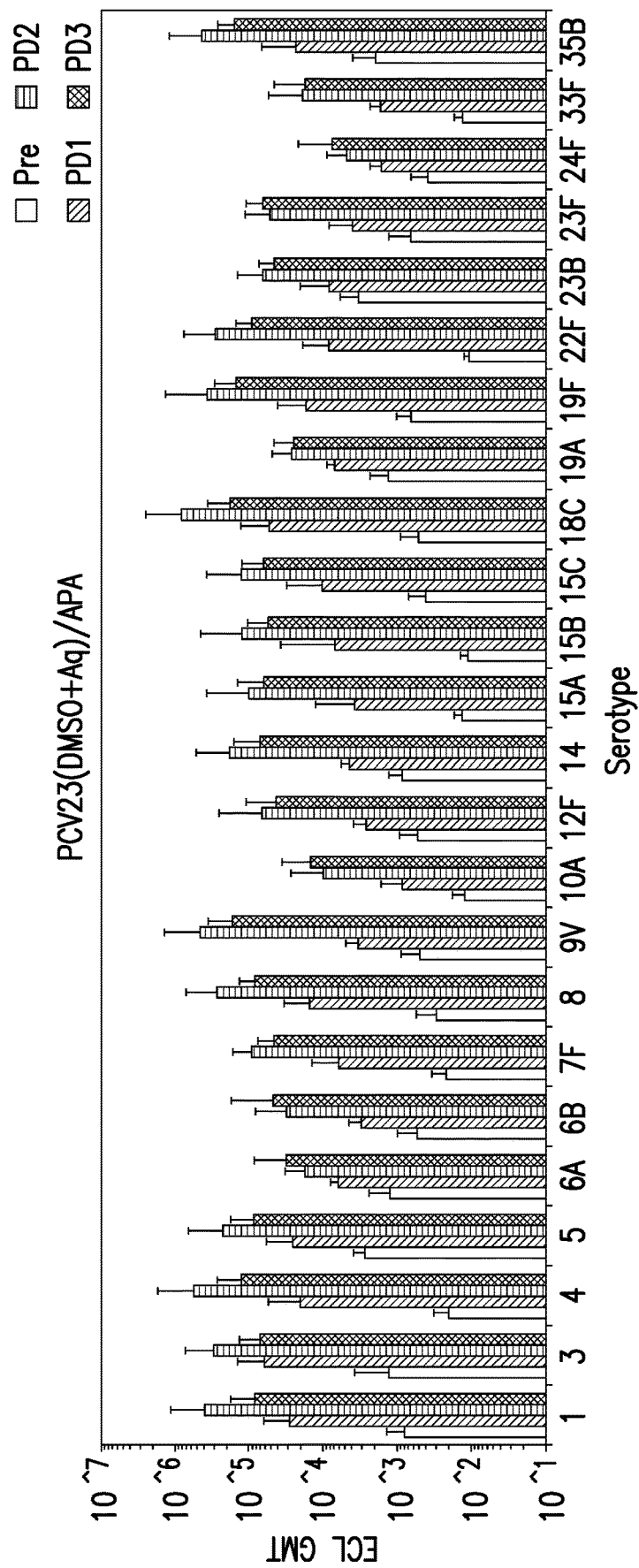
Figure 9D:
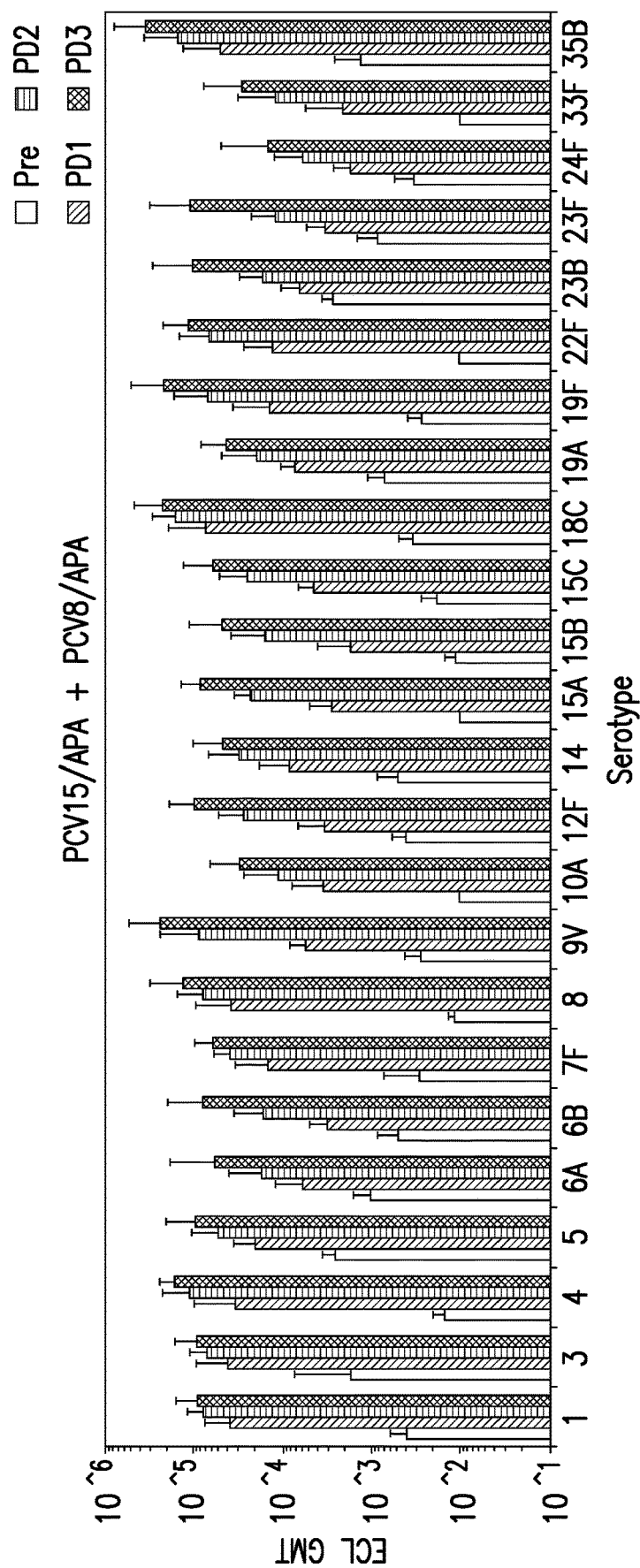

Rabbit sera were tested individually in multiplexed opsonophagocytic assays (MOPA) to determine functional antibody titers. PCV22 generated functional antibody titers in rabbits which killed vaccine-type bacterial serotypes following 2 immunizations with the vaccine (FIG. 8). PCV22 unadjuvanted had higher functional antibody titers at PD1 for serotype 4 (data not shown) and at PD2 for serotypes 1, 3 and 4 compared to PCV22 formulated with APA. PCV22 formulated with APA did not have higher functional antibody titers at PD1 (data not shown) and PD2 for most of the serotypes compared to PCV22 unadjuvanted (FIG. 8).

Example 51

PCV23 Immunogenicity in Infant Rhesus Macaques

Infant Rhesus macaques (IRM, 2-3 months old, n=8-9/group) were intramuscularly immunized with 0.1 mL of a 23-valent pneumococcal conjugate vaccine (PCV23) on days 0, 28 and 56. PCV23 was dosed at 9.6 µg of total pneumococcal polysaccharide (1, 3, 4, 5, 6A, 7F, 8, 9V, 10A, 12F, 14, 15A, 15C, 18C, 19A, 19F, 22F, 23B, 23F, 24F, 33F and 35B at 0.4 µg, 6B at 0.8 µg and all conjugated to CRM197) unadjuvanted or formulated with 25 µg aluminum phosphate adjuvant (APA) per immunization. An additional group of IRMs were intramuscularly immunized with a 0.1 mL of PCV15. PCV15 was dosed at 6.4 µg of total pneumococcal polysaccharide (1, 3, 4, 5, 6A, 7F, 9V, 14, 18C, 19A, 19F, 22F, 23F and 33F at 0.4 µg, 6B at 0.8 µg and all conjugated to CRM197 with 25 µg APA per immunization) in one quadricep and 0.1 mL of PCV8 (8, 10A, 12F, 15A, 15C, 23B, 24F and 35B at 0.4 µg and all conjugated to CRM197 with 25 µg APA per immunization) in a separate quadricep following the same schedule as described above. Sera were collected prior to study start (pre-immune, day 0) and on days 14 (PD1), 28, 42 (PD2), 56, and 70 (PD3). IRMs were observed at least daily by trained animal care staff for any signs of illness or distress. All animal experiments were performed in strict accordance with the recommendations in the Guide for Care and Use of Laboratory Animals of the National Institutes of Health. The experimental protocol was approved by the Institutional Animal Care and Use Committee at Merck & Co., Inc and New Iberia Research Center.

Rhesus sera were evaluated for IgG immunogenicity using a multiplexed electrochemiluminescence (ECL) assay. This assay was developed for use with Rhesus serum based on the human assay described by Marchese et al. and Skinner et al [3,4] using technology developed by MesoScale Discovery (a division of MesoScale Diagnostics, LLC, Gaithersburg, MD) which utilizes a SULFO-TAG™ label that emits light upon electrochemical stimulation. SULFO-TAG™-labeled anti-human IgG was used as the secondary antibody for testing Rhesus serum samples.

IRM immunization with PCV23 generated antibody titers for all serotypes for all of the PCV23 vaccine formulations evaluated (FIGS. 9A-9D). It is also of note that PCV23, which contains polysaccharide conjugates 15A-CRM197 and 15C-CRM197, also provides cross-reactivity to 15B, as evidenced in ECL (FIGS. 9A-9D). PCV23 was immunogenic with one dose of vaccine in the IRMs (FIGS. 9A-9D).

Figure 10A:
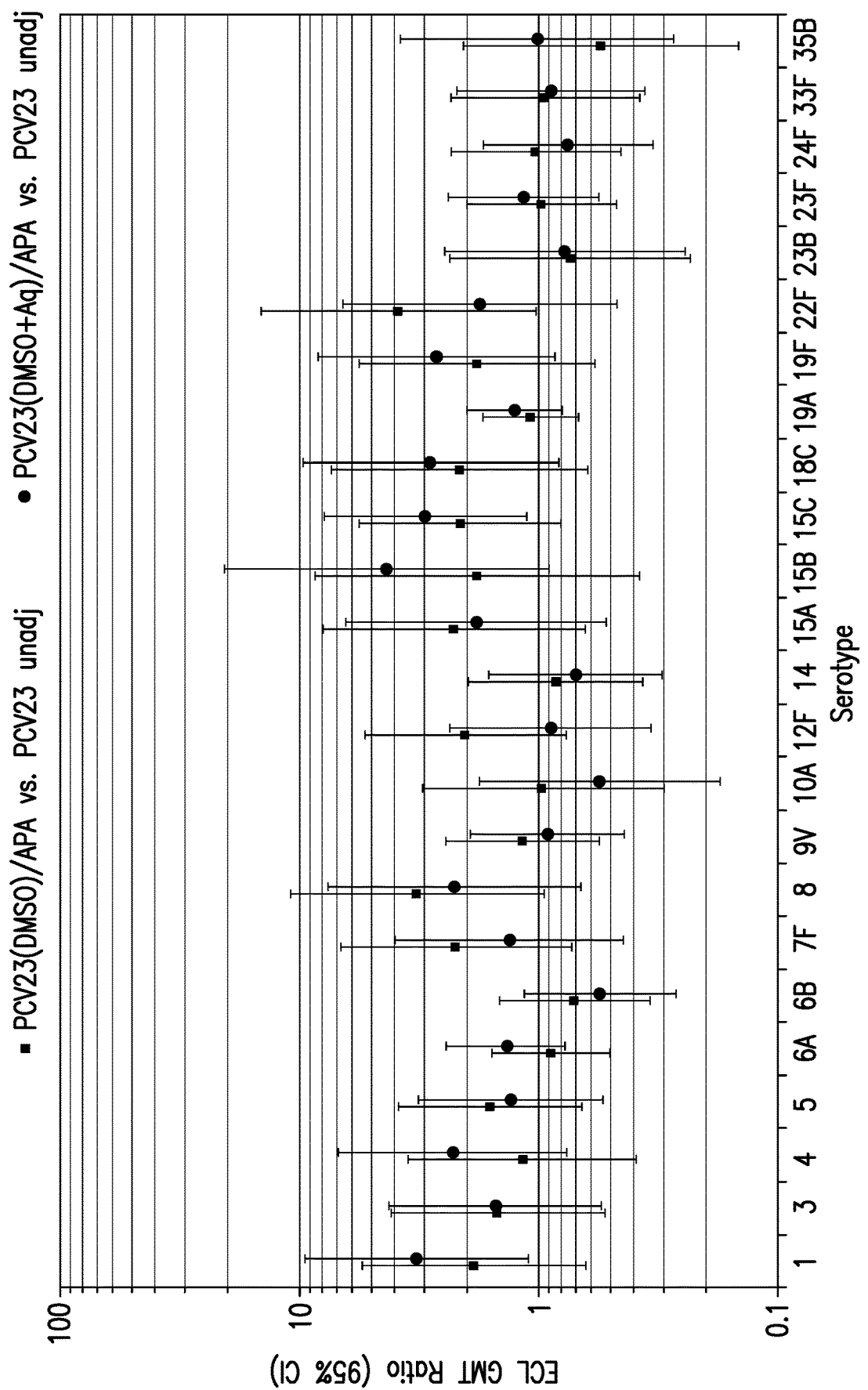
FIG. 10. Comparison of ECL antibody responses in IRMs (8-9 per group) following vaccination with PCV23 with or without APA. Symbols indicate ratios at A) PD1, B) PD2, or C) PD3. GMT ratios with error bars representing the 95% CIs.
Figure 10B:
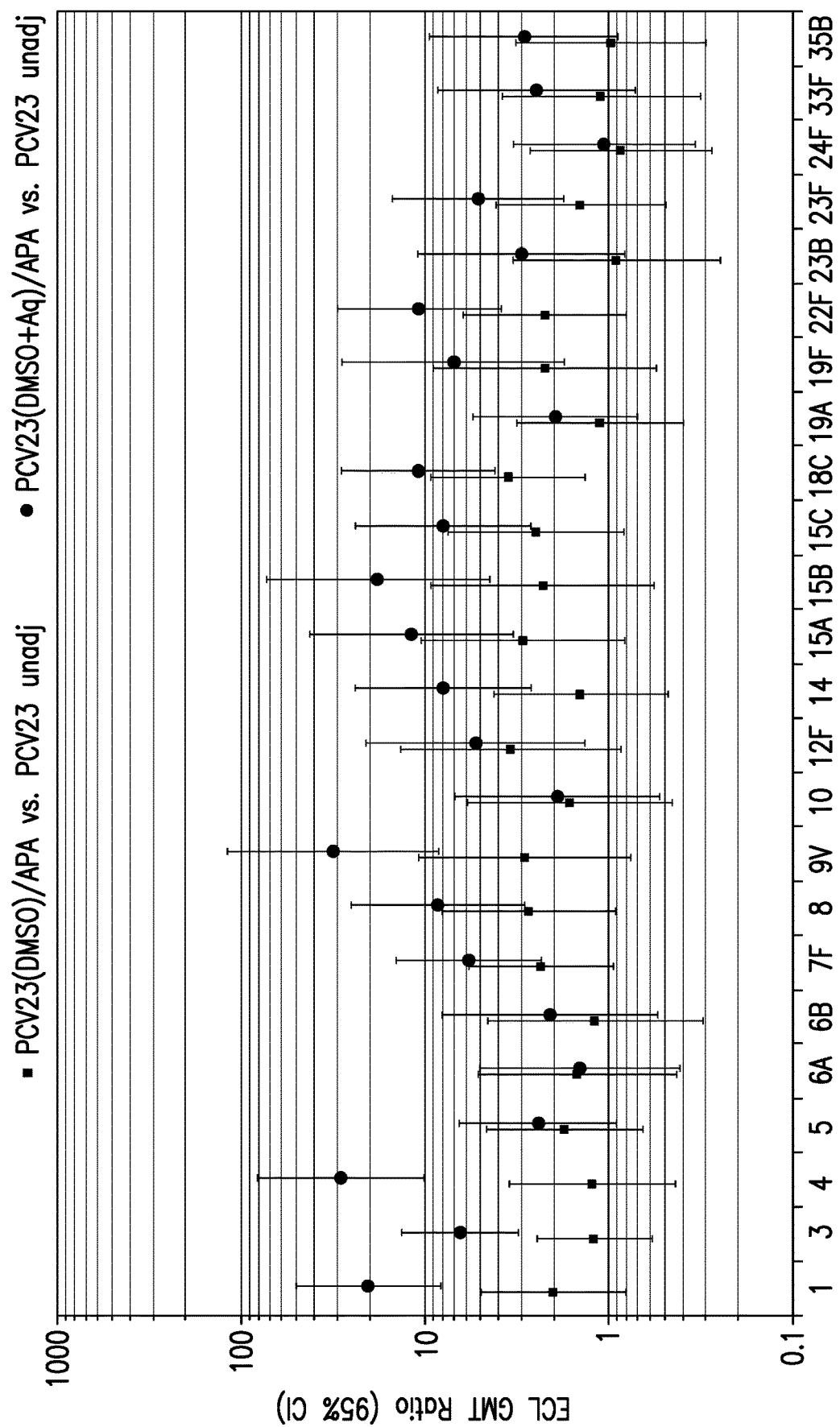
Figure 10C:
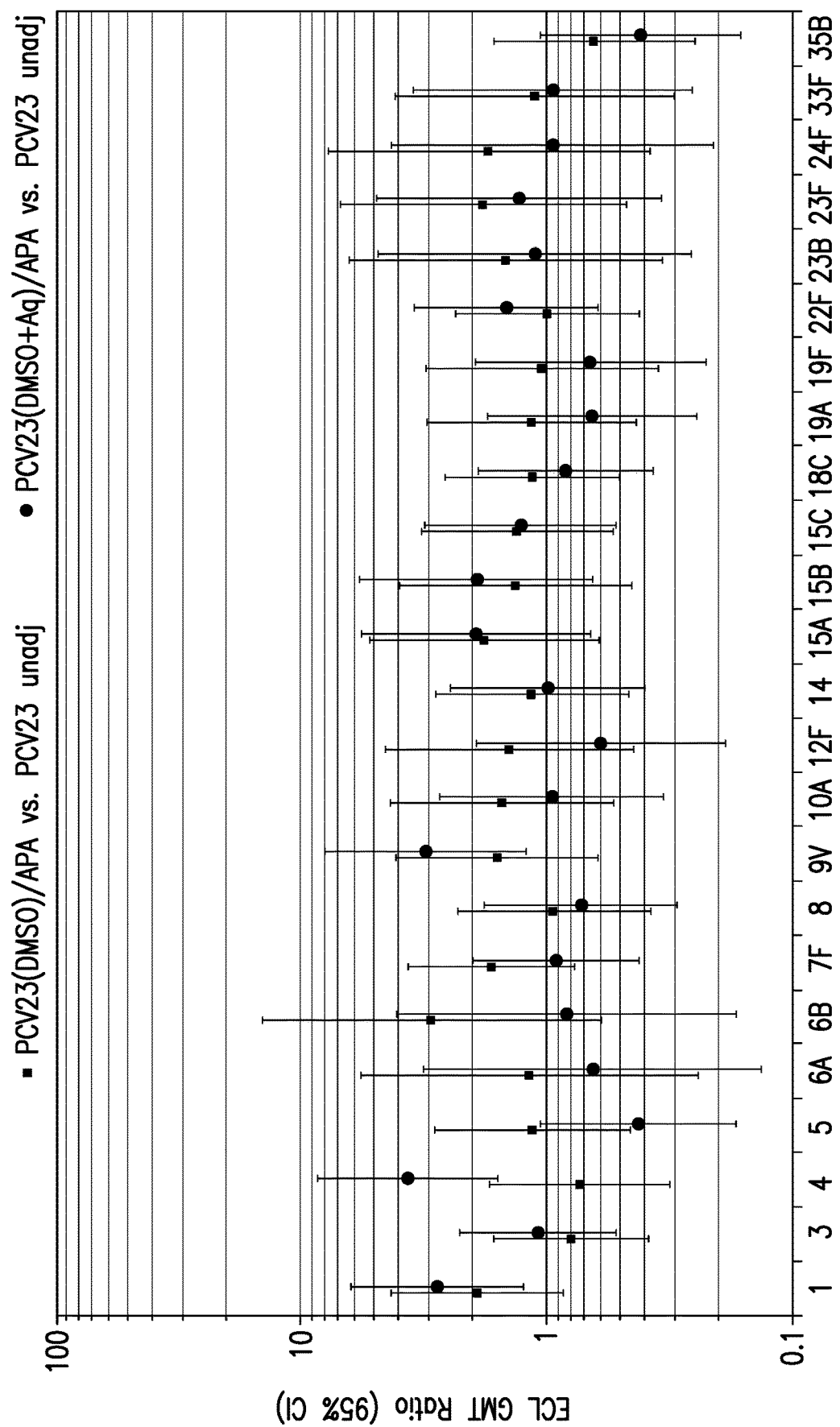

The PCV23 (DMSO)/APA formulation had higher immunogenicity for serotype 22F compared to PCV23 unadjuvanted at PD1 while PCV23 (DMSO+Aq)/APA had higher immunogenicity for serotype 1 and serotype 15C compared to PCV23 unadjuvanted at PD1 (FIG. 10A). The PCV23 (DMSO)/APA formulation had higher immunogenicity for serotype 18C compared to PCV23 unadjuvanted at PD2 (FIG. 10B). The PCV23 (DMSO+Aq)/APA had higher immunogenicity for the majority of serotypes (1, 3, 4, 7F, 8, 9V, 12F, 14, 15A, 15B, 15C, 18C, 19F, 22F and 23F) compared to PCV23 unadjuvanted at PD2 (FIG. 10B). The PCV23 (DMSO+Aq)/APA had higher immunogenicity for serotypes 1, 4 and 9V compared to PCV23 unadjuvanted at PD3 (FIG. 10C).

Figure 11A:
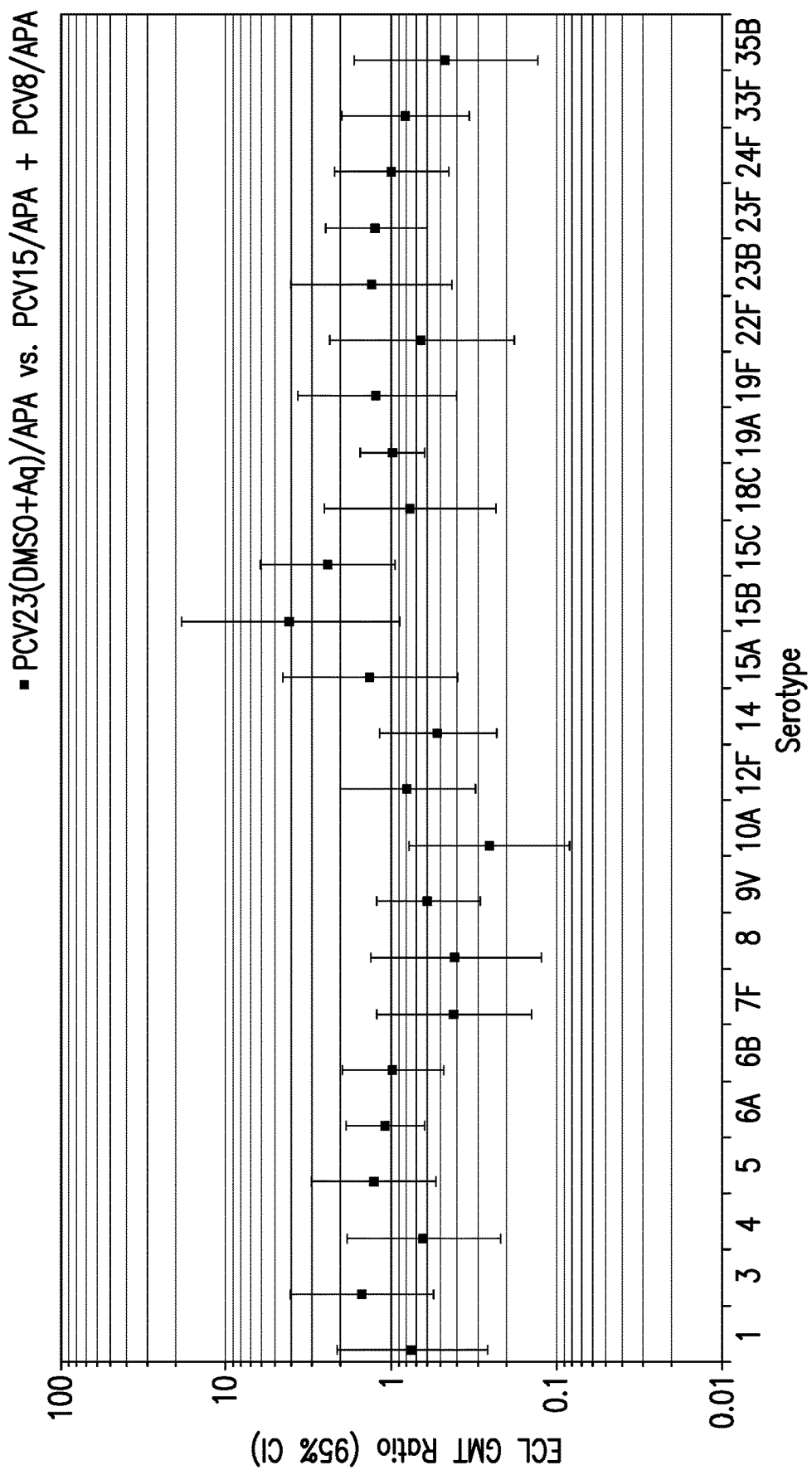
FIG. 11. Comparison of ECL antibody responses in IRMs (9 per group) following vaccination with PCV23 (DMSO+Aq)/APA or co-administrated with PCV15/APA+PCV8/APA. Symbols indicate ratios at A) PD1, B) PD2, and C) PD3. GMT ratios with error bars representing the 95% CIs.
Figure 11B:
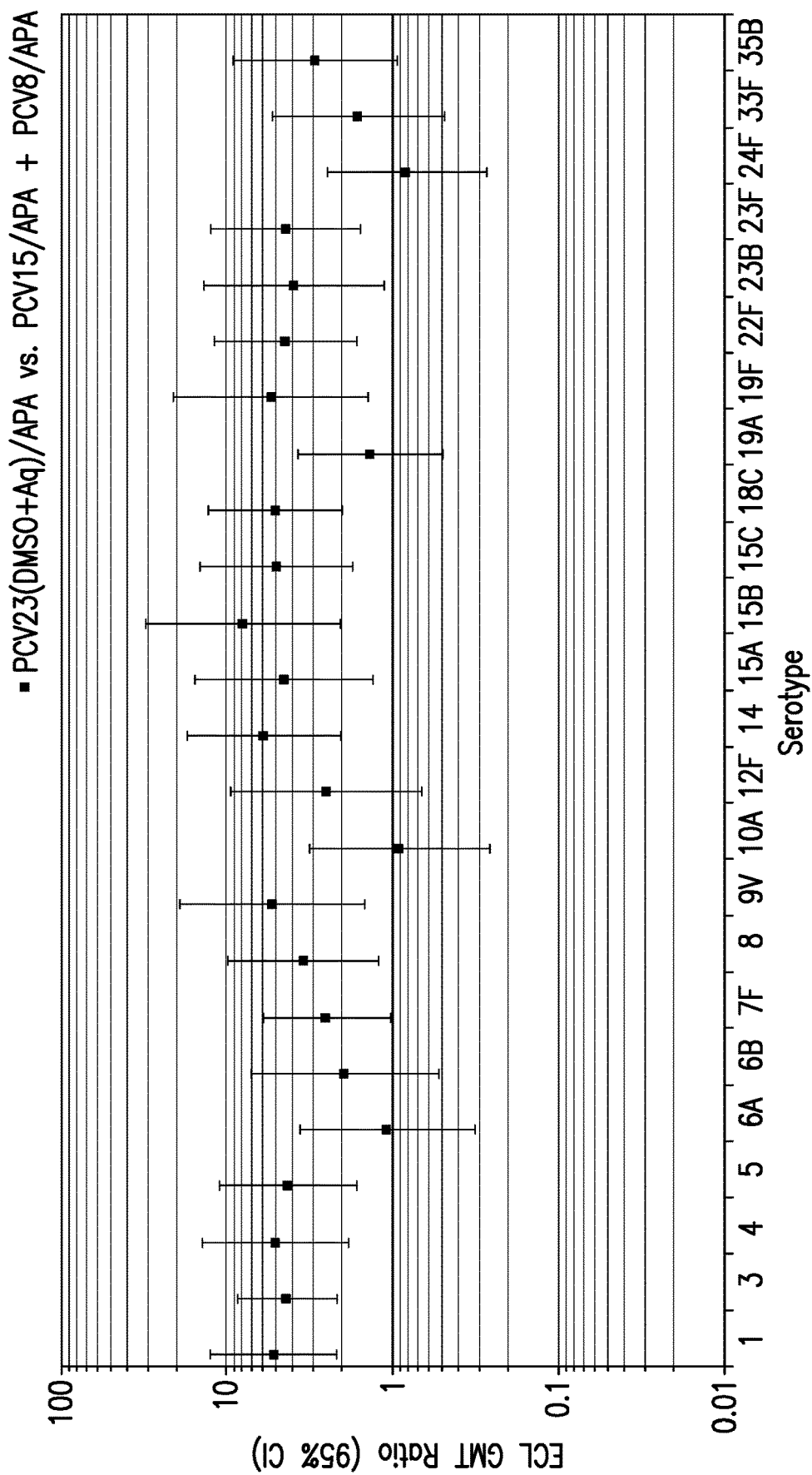
Figure 11C:
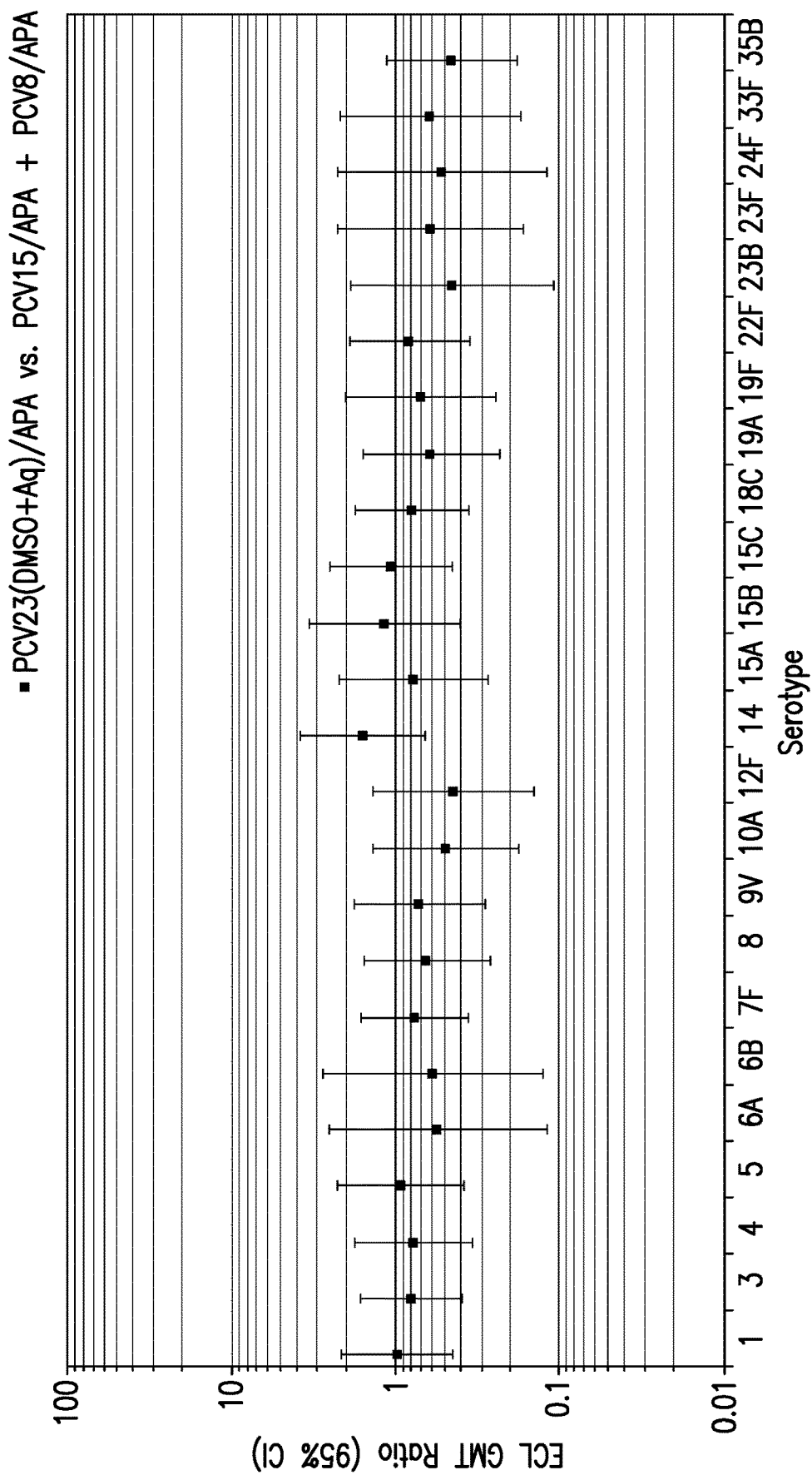

IRMs vaccinated with PCV23 (DMSO+Aq)/APA or with a co-administration of PCV15/APA+PCV8/APA in separate limbs did not show many immunogenicity differences at PD1, with the exception of serotype 10A which had higher immunogenicity in the coadministration group (FIG. 11A). However, IRMs vaccinated with PCV23 (DMSO+Aq)/APA had higher PD2 immunogenicity for the majority of serotypes 1, 3, 4, 5, 7F, 8, 9V, 14, 15A, 15B, 15C, 18C, 19F, 22F, 23B and 23F compared to co-administration of PCV15/APA+PCV8/APA (FIG. 11B). There were no differences in immunogenicity between the two vaccines at PD3 (FIG. 11C).

Figure 12A:
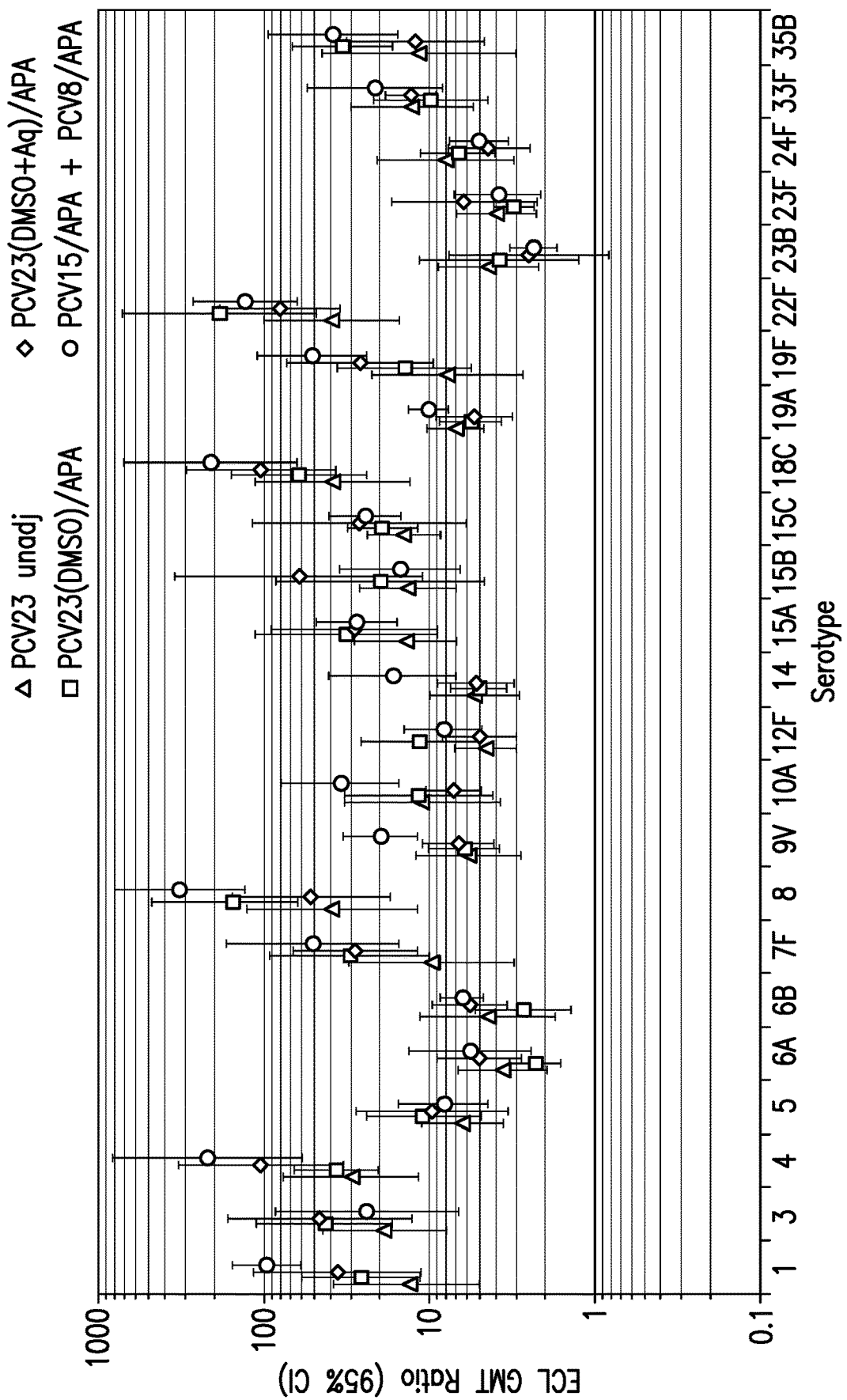
FIG. 12. Comparison of boosted ECL antibody responses in IRMs (8-9 per group) following vaccination with PCV23 unadjuvanted, PCV23(DMSO)/APA, PCV23(DMSO+Aq)/APA or PCV15/APA+PCV8/APA. A) PD1/Pre, B) PD2/Pre, C) PD3/Pre, D) PD2/PD1 and E) PD3/PD2. Symbols are GMT ratios with error bars representing the 95% CIs.
Figure 12B:
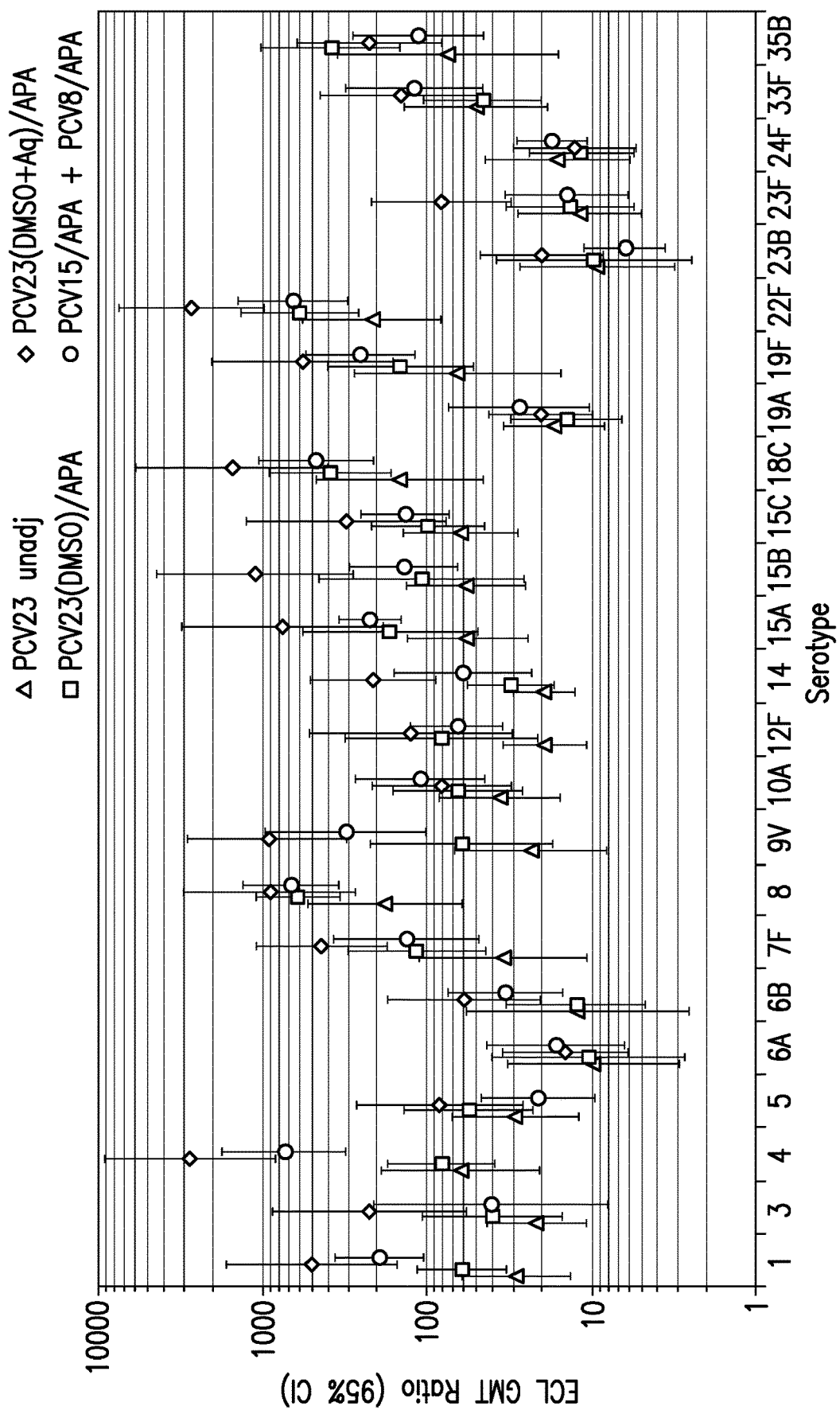
Figure 12C:
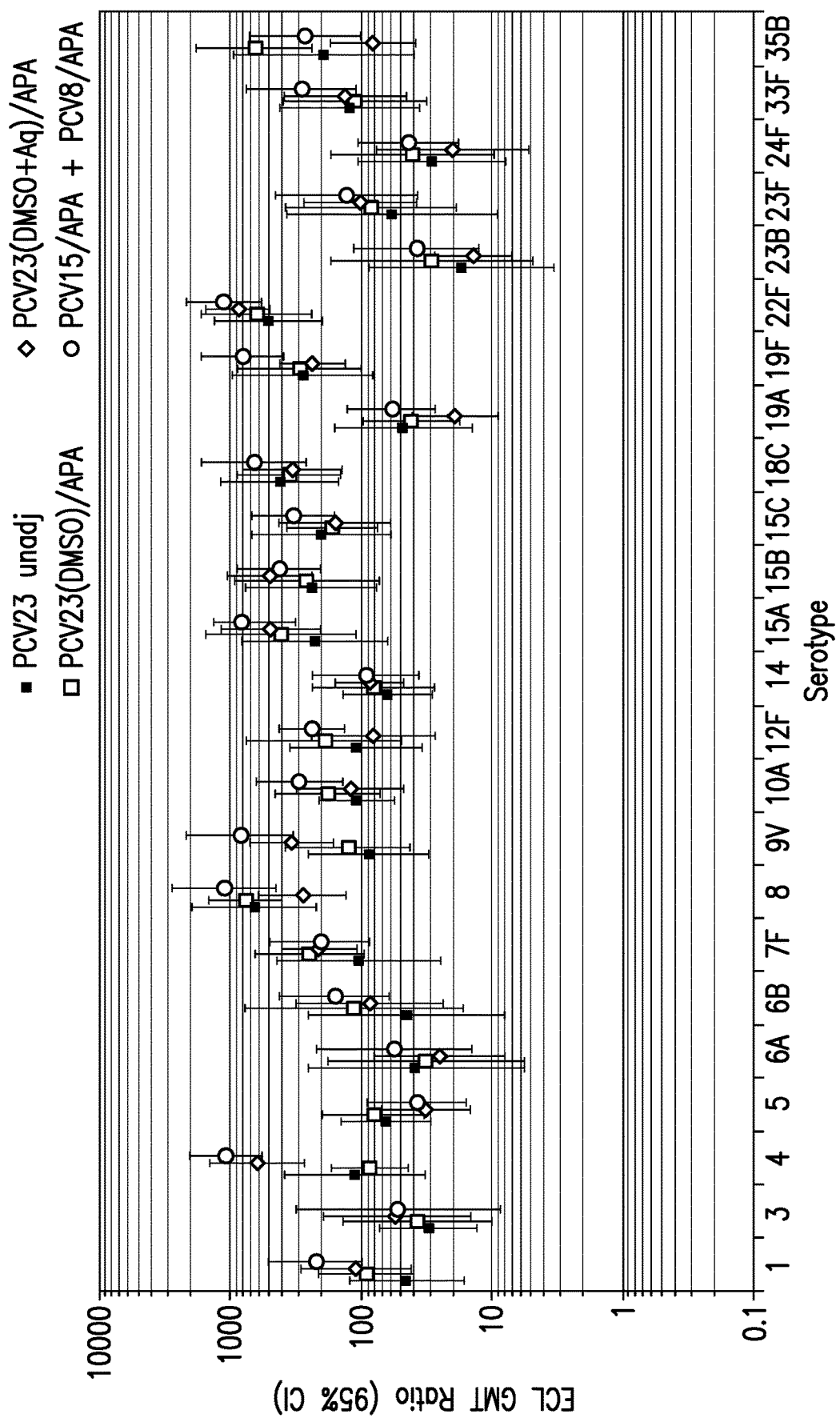
Figure 12D:
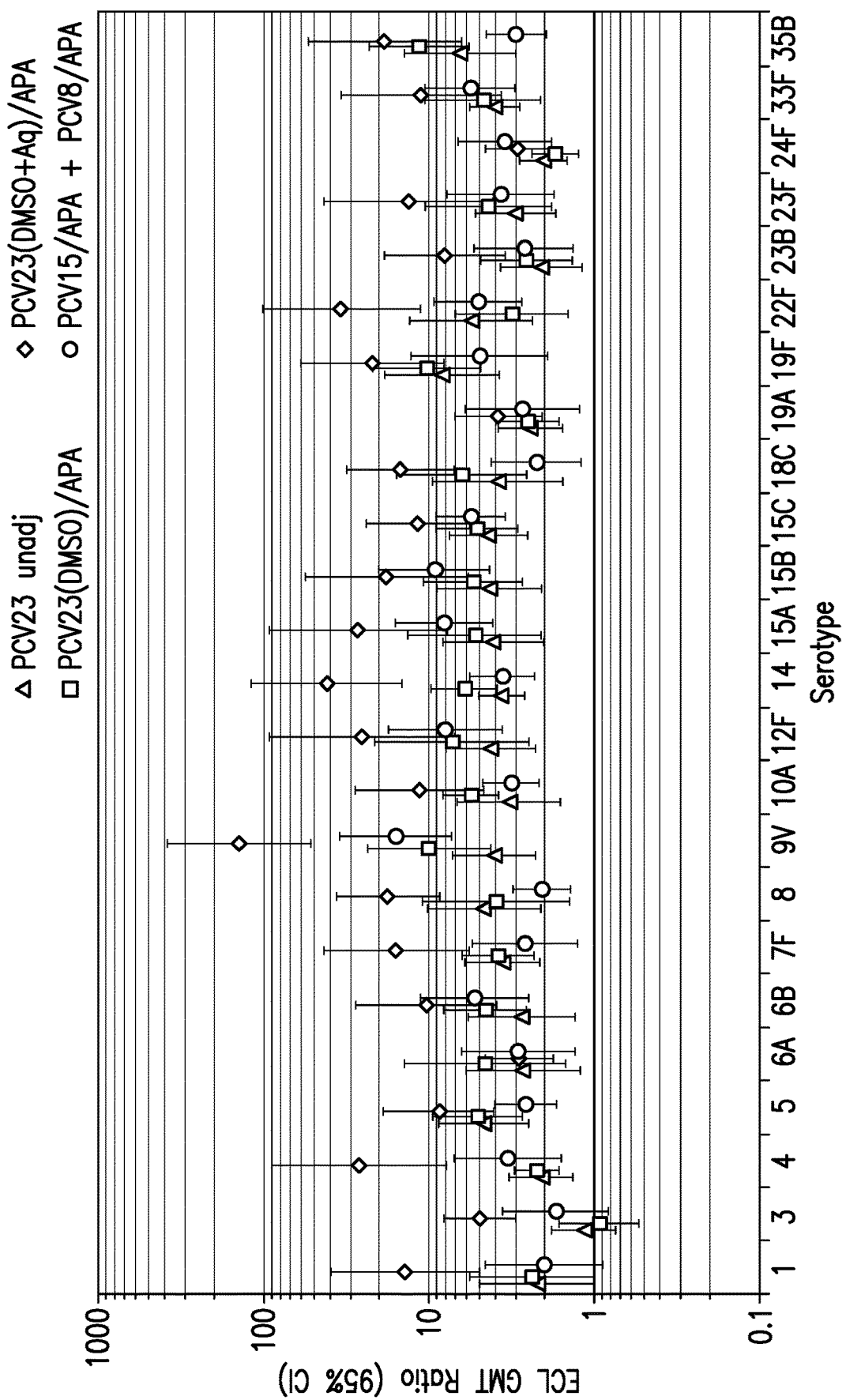
Figure 12E:
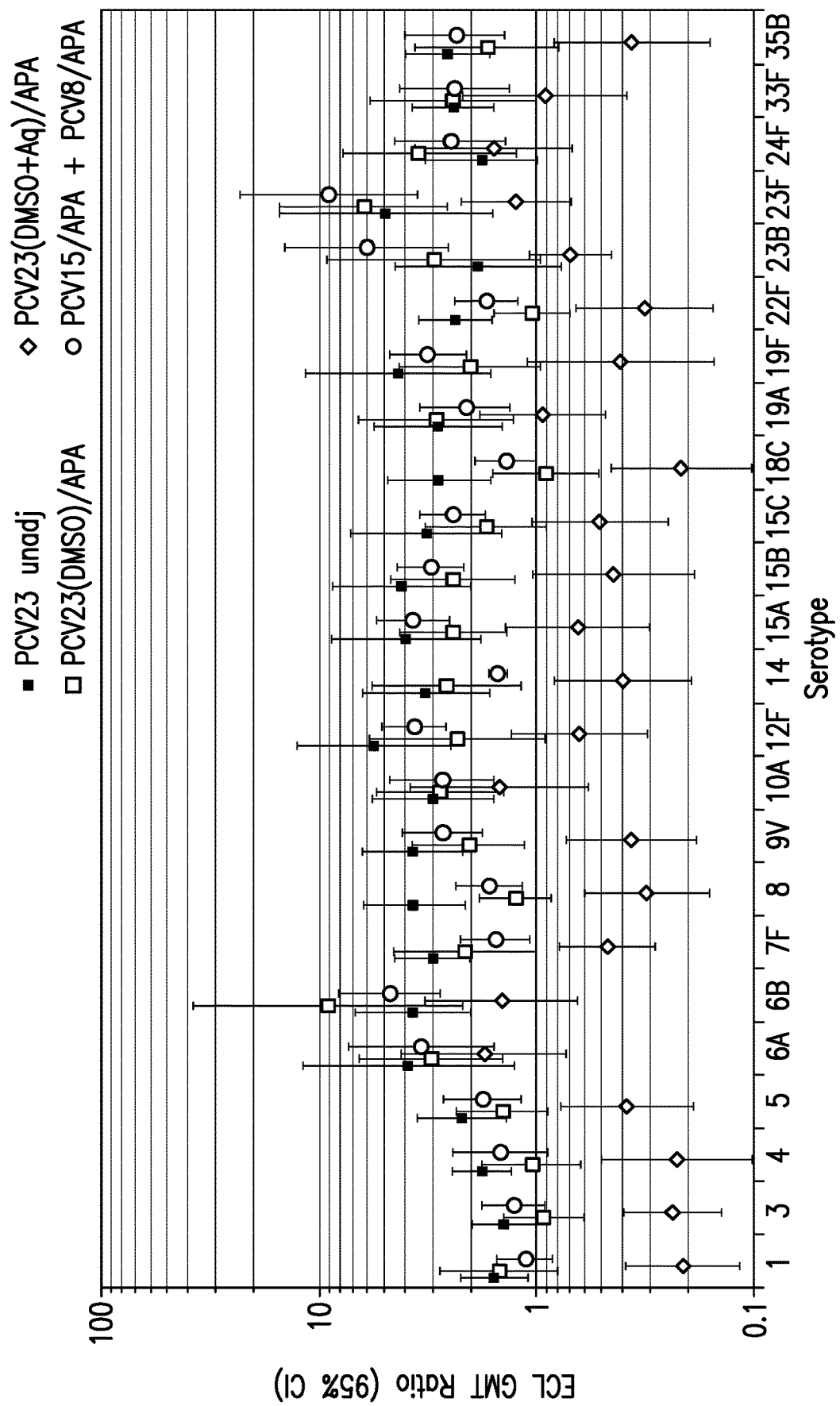

When evaluating the antibody boosting effects, all of the PCVs generated primary immune responses at PD1 compared to pre-immune sera for all serotypes with the exception of serotype 23B in IRMs immunized with PCV23 (DMSO+Aq)/APA (FIG. 12A). All PCVs evaluated generated significantly higher antibody titers at PD2 and PD3 when compared to pre-immune sera for all serotypes (FIGS. 12B and 12C). A second dose of PCV results in increased antibody titers from PD2 compared to PD1 for all serotypes except for serotype 3 and serotype 1 in IRMs immunized with PCV23 unadjuvanted, PCV23 (DMSO)/APA and PCV15/APA+PCV8/APA (FIG. 12D). A third dose of PCV results a boost in antibody titers for the majority of serotypes, with the exception of IRMs immunized with PCV23 (DMSO+Aq)/APA where there is a decrease at PD3 compared to PD2, suggesting that PCV23 (DMSO+Aq)/APA immunized IRMs reached the maximum antibody response at PD2 (FIG. 12E).

Example Z

PCV24 Immunogenicity in New Zealand White Rabbits and Infant Rhesus Macaques

New Zealand white rabbits (NZWR, n=8/group) were intramuscularly immunized with 0.1 mL of a 24-valent pneumococcal conjugate vaccine (PCV24) on days 0 and 14. PCV24 was dosed at 9.6 µg of total pneumococcal polysaccharide (1, 3, 4, 5, 6A, 6B, 7F, 8, 9V, 10A, 11A, 12F, 14, 15A, deOAc15B, 18C, 19A, 19F, 22F, 23B, 23F, 24F, 33F and 35B at 0.4 µg and all conjugated to CRM197) and formulated with aluminum phosphate adjuvant (APA, 25 µg) per immunization. Sera were collected prior to study start (pre-immune, day 0) and on days 14 (PD1) and 28 (PD2). NZWRs were observed at least daily by trained animal care staff for any signs of illness or distress.

Infant Rhesus macaques (IRM, 2-3 months old, n=5/group) were intramuscularly immunized with 0.1 mL of a 24-valent pneumococcal conjugate vaccine (PCV24) on days 0, 28 and 56. PCV24 was dosed at 9.6 µg of total pneumococcal polysaccharide (1, 3, 4, 5, 6A, 6B, 7F, 8, 9V, 10A, 11A, 12F, 14, 15A, deOAc15B, 18C, 19A, 19F, 22F, 23B, 23F, 24F, 33F and 35B at 0.4 µg and all conjugated to CRM197) and formulated with aluminum phosphate adjuvant (APA, 25 µg) per immunization. Sera were collected prior to study start (pre-immune, day 0) and on days 14 (PD1), 28, 42 (PD2), 56, and 70 (PD3). IRMs were observed at least daily by trained animal care staff for any signs of illness or distress. All animal experiments were performed in strict accordance with the recommendations in the Guide for Care and Use of Laboratory Animals of the National Institutes of Health. The experimental protocol was approved by the Institutional Animal Care and Use Committee at Merck & Co., Inc and New Iberia Research Center.

Rhesus sera were evaluated for IgG immunogenicity using a multiplexed electrochemiluminescence (ECL) assay. This assay was developed for use with Rhesus serum based on the human assay described by Marchese et al. and Skinner et al [3, 4] using technology developed by MesoScale Discovery (a division of MesoScale Diagnostics, LLC, Gaithersburg, MD) which utilizes a SULFO-TAG™ label that emits light upon electrochemical stimulation. SULFO-TAG™-labeled anti-human IgG was used as the secondary antibody for testing Rhesus serum samples and a SULFO-TAG™-labeled anti-rabbit IgG for the New Zealand white rabbit samples.

Functional antibody was determined through multiplexed opsonophagocytic assays (MOPA) based on previously described protocols at www.vaccine.uab.edu and Opsotiter® 3 software owned by and licensed from University of Alabama (UAB) Research Foundation [1, 2].

Figure 13A:
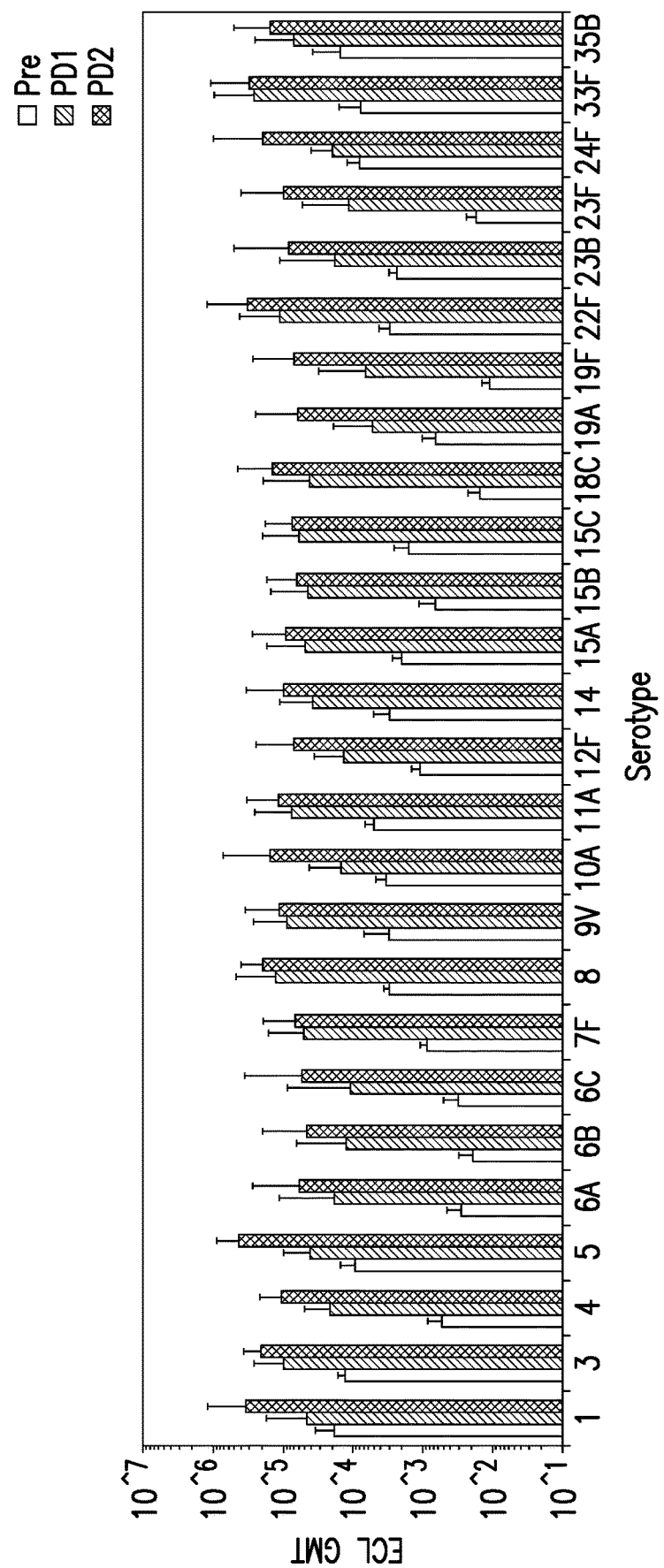
FIG. 13. (A) Pre-immune (Pre), post-dose 1 (PD1) and 2 (PD2) IgG antibody dilution titers as determined by ECL for New Zealand white rabbits immunized with PCV24 formulated with aluminum phosphate adjuvant (PCV24/APA). Error bars represent the 95% confidence intervals (CI) of the geometric mean titer (GMT). (B) Serotype specific OPA dilution titers (pre-immune and PD2) for NZWRs immunized with PCV24/APA. Error bars represent the variation in functional antibody titers for eight NZWRs.

NZWR immunization with PCV24 generated antibody titers for all serotypes in the vaccine (FIG. 13A). It is also of note that PCV24, which contains polysaccharide conjugates 15A-CRM197, deOAc15B-CRM197, 6A-CRM197, 6B-CRM197 also provides cross-reactivity to 15B and 6C, as evidenced in ECL (FIG. 13A).

Figure 13B:
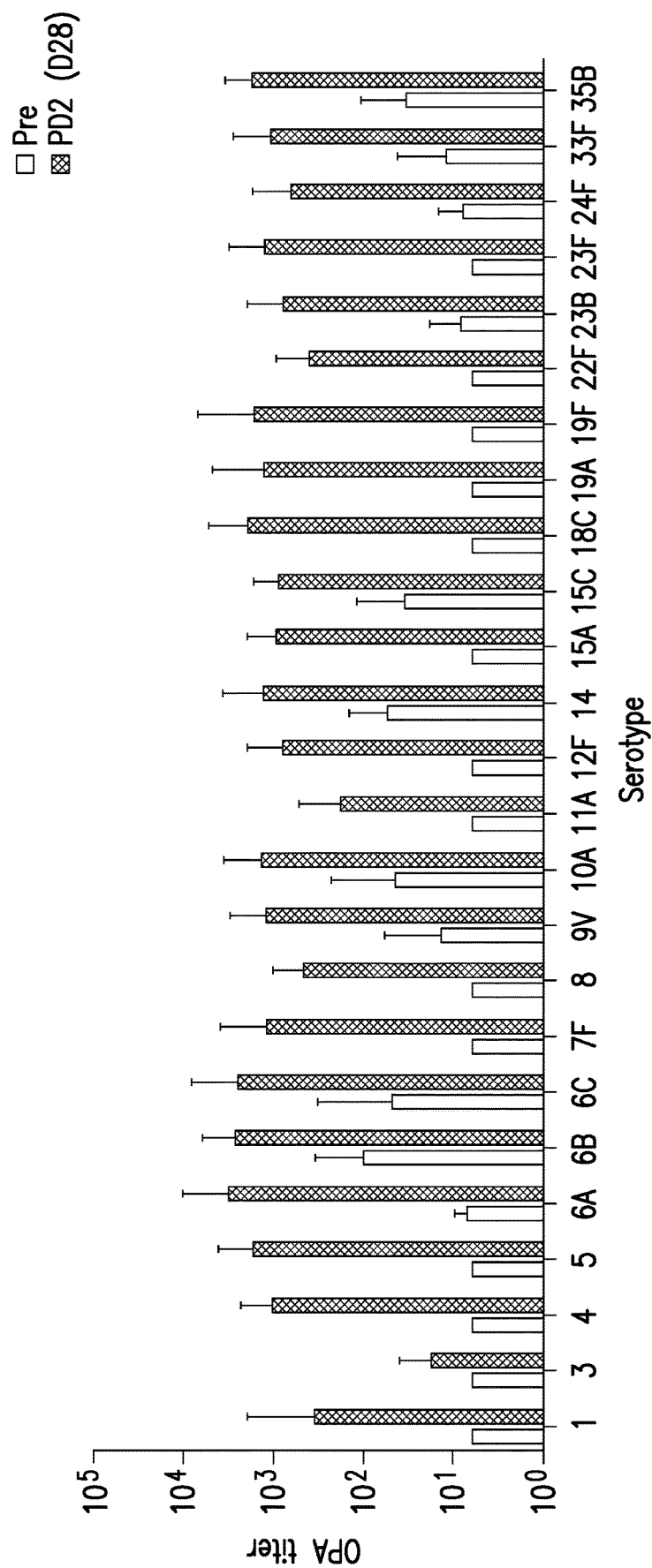

NZWR sera were tested individually in multiplexed opsonophagocytic assays (MOPA) to determine functional antibody titers. PCV24 generated functional antibody titers in NZWRs which killed all vaccine-type bacterial serotypes (FIG. 13B).

Figure 14A:
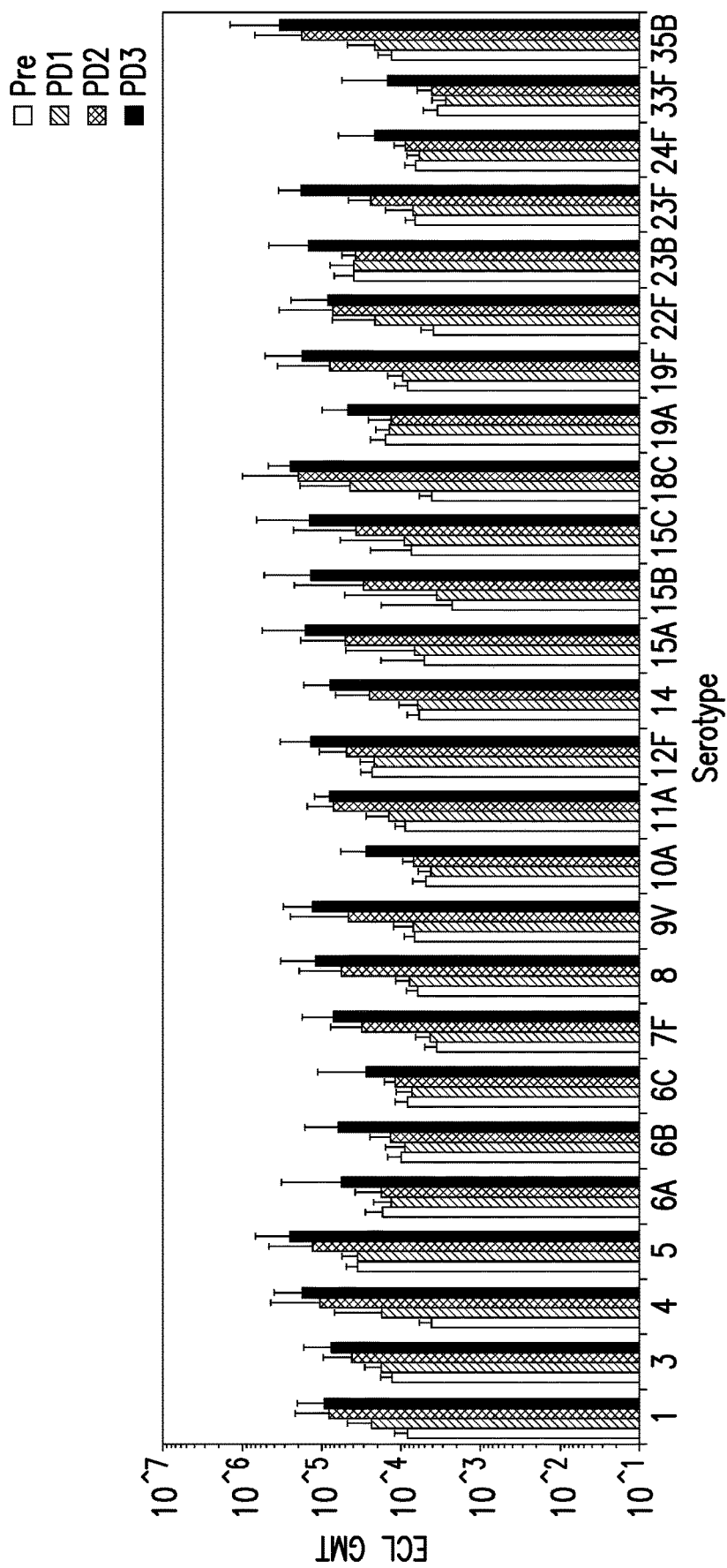
FIG. 14. (A) Pre-immune (Pre), post-dose 1 (PD1), 2 (PD2) and 3 (PD3) IgG antibody dilution titers as determined by ECL for infant Rhesus monkeys (IRMs) immunized with PCV24 formulated with aluminum phosphate adjuvant (PCV24/APA). Error bars represent the 95% confidence intervals (CI) of the geometric mean titer (GMT). (B) Serotype specific OPA dilution titers (pre-immune and PD3) for IRMs immunized with PCV24/APA. Error bars represent the variation in functional antibody titers for five IRMs.

IRM immunization with PCV24 generated antibody titers for all serotypes in the vaccine (FIG. 14A). It is also of note that PCV24, which contains polysaccharide conjugates 15A-$CRM_{197}$, deOAc15B-$CRM_{197}$, 6A-CRM197, 6B-$CRM_{197}$ also provides cross-reactivity to 15B and 6C, as evidenced in ECL (FIG. 14A).

Figure 14B:
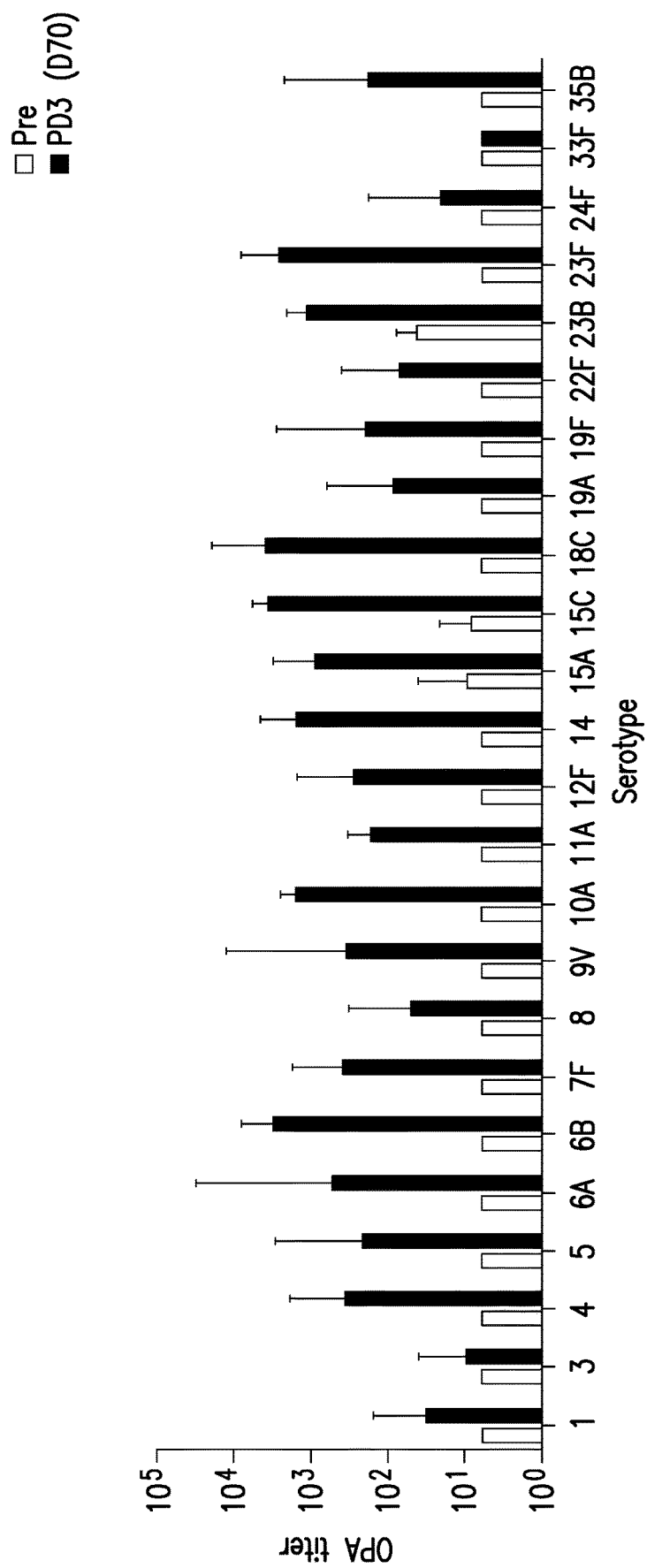

IRM sera were tested individually in multiplexed opsonophagocytic assays (MOPA) to determine functional antibody titers. PCV24 generated functional antibody titers in IRMs which killed vaccine-type bacterial serotypes (FIG. 14B), with the exception of 33F, which also had lower PD3/Pre binding antibody titers in ECL. However, when PCV24/APA was evaluated in New Zealand white rabbits, PD2 33F OPA titers were over 58-fold higher than pre-immune titers (FIG. 13B).

REFERENCES

1. Caro-Aguilar I, Indrawati L, Kaufhold R M, Gaunt C, Zhang Y, Nawrocki D K, et al. Immunogenicity differences of a 15-valent pneumococcal polysaccharide conjugate vaccine (PCV15) based on vaccine dose, route of immunization and mouse strain. Vaccine 2017 Feb. 7; 35(6):865-72.

2. Burton R L, Nahm M H. Development and validation of a fourfold multiplexed opsonization assay (MOPA4) for pneumococcal antibodies. Clin Vaccine Immunol 2006 September; 13(9):1004-9.
3. Marchese R D, Puchalski D, Miller P, Antonello J, Hammond O, Green T, Rubinstein L J, Caulfield M J, Sikkema D. Optimization and validation of a multiplex, electrochemiluminescence-based detection assay for the quantitation of immunoglobulin G serotype-specific anti-pneumococcal antibodies in human serum. Clin Vaccine Immunol. 2009 March; 16(3):387-96.
4. Skinner, J. M., et al., Pre-clinical evaluation of a 15-valent pneumococcal conjugate vaccine (PCV15-CRM197) in an infant-rhesus monkey immunogenicity model. Vaccine, 2011. 29(48): p. 8870-8876.

Example 52

Materials and Methods
Free Polysaccharide Testing

Free polysaccharide (polysaccharide that is not conjugated with CRM197) in conjugate sample is measured by first precipitating free protein and conjugates with deoxycholate (DOC) and hydrochloric acid. Precipitates are then filtered out and the filtrates are analyzed for free polysaccharide concentration by HPSEC/UV/MALS/RI. Free polysaccharide is calculated as a percentage of total polysaccharide measured by HPSEC/UV/MALS/RI.

Free Protein Testing

Free polysaccharide, polysaccharide-CRM197 conjugate, and free CRM197 in conjugate samples are separated by capillary electrophoresis in micellar electrokinetic chromatography (MEKC) mode. Briefly, samples are mixed with MEKC running buffer containing 25 mM borate, 100 mM SDS, pH 9.3, and are separated in a preconditioned bare-fused silica capillary. Separation is monitored at 200 nm and free CRM197 is quantified with a CRM197 standard curve. Free protein results are reported as a percentage of total protein content determined by the HPSEC/UV/MALS/RI procedure.

Molecular Weight and Concentration Analysis of Conjugates Using HPSEC/UV/MALS/RI Assay Conjugate samples were injected and separated by high performance size-exclusion chromatography (HPSEC). Detection was accomplished with ultraviolet (UV), multi-angle light scattering (MALS) and refractive index (RI) detectors in series. Protein concentration was calculated from UV280 using an extinction coefficient. Polysaccharide concentration was deconvoluted from the RI signal (contributed by both protein and polysaccharide) using the do/dc factors which are the change in a solution's refractive index with a change in the solute concentration reported in mL/g. Average molecular weight of the samples were calculated by Astra software (Wyatt Technology Corporation, Santa Barbara, CA) using the measured concentration and light scattering information across the entire sample peak. There are multiple form of average values of molecular weight for polydispersed molecules. For example number-average molecular weight Mn, weight-average molecular weight Mw, and z-average molecular weight Mz (Molecules, 2015, 20, 10313-10341). Unless specified, the molecular weights are weight-average molecular weight.

Determination of Lysine Consumption in Conjugated Protein as a Measure of the Number of Covalent Attachments Between Polysaccharide and Carrier Protein The Waters AccQ-Tag amino acid analysis (AAA) was used to measure the extent of conjugation in conjugate samples. Samples were hydrolyzed using vapor phase acid hydrolysis in the Eldex workstation, to break the carrier proteins down into their component amino acids. The free amino acids were derivatized using 6-aminoquinolyl-N-hydroxysuccinimidyl carbamate (AQC). The derivatized samples were then analyzed using UPLC with UV detection on a C18 column. The average protein concentration was obtained using representative amino acids other than lysine. Lysine consumption during conjugation (i.e., lysine loss) was determined by the difference between the average measured amount of lysine in the conjugate and the expected amount of lysine in the starting protein.

What is claimed is:

1. A method for the prevention of invasive pneumococcal disease (IPD) and pneumococcal pneumonia (PP) in patients comprising administering a multivalent immunogenic composition to the patient, wherein the multivalent immunogenic composition comprises S. pneumoniae polysaccharide carrier protein conjugates, wherein each of the conjugates comprises a polysaccharide of a particular S. pneumoniae serotype conjugated to a carrier protein, wherein the S. pneumoniae serotypes consist of 1, 3, 4, 5, 6A, 6B, 7F, 8, 9V, 10A, 11A, 12F, 14, 15A, 15B, 18C, 19A, 19F, 22F, 23B, 23F, 24F, 33F and 35B, and the carrier protein is CRM197.

2. A method for the prevention of invasive pneumococcal disease (IPD) and pneumococcal pneumonia (PP) in patients comprising administering a multivalent immunogenic composition to the patient, wherein the multivalent immunogenic composition comprises S. pneumoniae polysaccharide carrier protein conjugates, wherein each of the conjugates comprises a polysaccharide of a particular S. pneumoniae serotype conjugated to a carrier protein, wherein the S. pneumoniae serotypes consist of 1, 3, 4, 5, 6A, 6B, 7F, 8, 9V, 10A, 11A, 12F, 14, 15A, de-O-acetylated 15B, 18C, 19A, 19F, 22F, 23B, 23F, 24F, 33F and 35B, and the carrier protein is CRM197.

3. The method of claim 2, wherein the de-O-acetylated S. pneumoniae serotype 15B polysaccharide has an O-acetyl content per repeating unit of less than 5%.

4. The method of claim 2, wherein the de-O-acetylated S. pneumoniae serotype 15B polysaccharide has an O-acetyl content per repeating unit in the range of 0-5%.

5. The method of claim 2, wherein the de-O-acetylated S. pneumoniae serotype 15B polysaccharide has an O-acetyl content per repeating unit in the range of 0-4%.

6. The method of claim 2, wherein the de-O-acetylated S. pneumoniae serotype 15B polysaccharide has an O-acetyl content per repeating unit in the range of 0-3%.

7. The method of claim 2, wherein the de-O-acetylated S. pneumoniae serotype 15B polysaccharide has an O-acetyl content per repeating unit in the range of 0-2%.

8. The method of claim 2, wherein the de-O-acetylated S. pneumoniae serotype 15B polysaccharide has an O-acetyl content per repeating unit in the range of 0-1%.

9. The method of claim 2, wherein the de-O-acetylated S. pneumoniae serotype 15B polysaccharide has an O-acetyl content per repeating unit in the range of 0-0.5%.

10. The method of claim 2, wherein the de-O-acetylated S. pneumoniae serotype 15B polysaccharide has an O-acetyl content per repeating unit in the range of 0-0.1%.

11. The method of claim 2, wherein the de-O-acetylated S. pneumoniae serotype 15B polysaccharide has no O-acetyl content.

* * * * *

SEQUENCE LISTING

```
Sequence total quantity: 1
SEQ ID NO: 1            moltype = AA  length = 535
FEATURE                 Location/Qualifiers
REGION                  1..535
                        note = CRM197 variant of diphtheria toxin
source                  1..535
                        mol_type = protein
                        organism = synthetic construct
SEQUENCE: 1
GADDVVDSSK SFVMENFSSY HGTKPGYVDS IQKGIQKPKS GTQGNYDDDW KEFYSTDNKY   60
DAAGYSVDNE NPLSGKAGGV VKVTYPGLTK VLALKVDNAE TIKKELGLSL TEPLMEQVGT  120
EEFIKRFGDG ASRVVLSLPF AEGSSSVEYI NNWEQAKALS VELEINFETR GKRGQDAMYE  180
YMAQACAGNR VRRSVGSSLS CINLDWDVIR DKTKTKIESL KEHGPIKNKM SESPNKTVSE  240
EKAKQYLEEF HQTALEHPEL SELKTVTGTN PVFAGANYAA WAVNVAQVID SETADNLEKT  300
TAALSILPGI GSVMGIADGA VHHNTEEIVA QSIALSSLMV AQAIPLVGEL VDIGFAAYNF  360
VESIINLFQV VHNSYNRPAY SPGHKTQPFL HDGYAVSWNT VEDSIIRTGF QGESGHDIKI  420
TAENTPLPIA GVLLPTIPGK LDVNKSKTHI SVNGRKIRMR CRAIDGDVTF CRPKSPVYVG  480
NGVHANLHVA FHRSSSEKIH SNEISSDSIG VLGYQKTVDH TKVNSKLSLF FEIKS       535
```